United States Patent [19]

Grove et al.

[11] Patent Number: 5,707,403
[45] Date of Patent: *Jan. 13, 1998

[54] METHOD FOR THE LASER TREATMENT OF SUBSURFACE BLOOD VESSELS

[75] Inventors: Robert E. Grove, Pleasanton; James Z. Holtz, Livermore, both of Calif.

[73] Assignee: Star Medical Technologies, Inc., Pleasanton, Calif.

[ * ] Notice: The term of this patent shall not extend beyond the expiration date of Pat. No. 5,527,350.

[21] Appl. No.: 636,286

[22] Filed: Apr. 23, 1996

Related U.S. Application Data

[63] Continuation-in-part of Ser. No. 22,978, Feb. 24, 1993, Pat. No. 5,527,350.

[51] Int. Cl.$^6$ ............................................. A61N 5/006
[52] U.S. Cl. ............................ 607/89; 606/3; 606/9
[58] Field of Search ........................ 606/3, 9, 13, 17; 607/88, 89

[56] References Cited

U.S. PATENT DOCUMENTS

| | | | |
|---|---|---|---|
| 4,122,853 | 10/1978 | Smith | 128/303.1 |
| 4,733,660 | 3/1988 | Itzkan | 128/303.1 |
| 4,829,262 | 5/1989 | Furomoto | 330/4.3 |
| 4,917,084 | 4/1990 | Sinofsky | 606/7 |
| 4,917,486 | 4/1990 | Raven et al. | 351/221 |
| 4,930,504 | 6/1990 | Diamantopoulos et al. | 607/88 |
| 4,996,046 | 2/1991 | Warshaw et al. | 424/78 |
| 5,217,455 | 6/1993 | Tan | 606/9 |
| 5,344,418 | 9/1994 | Ghaffari | 607/89 |
| 5,558,667 | 9/1996 | Yarborough et al. | 606/9 |

OTHER PUBLICATIONS

S.M. Hacker et al., "The Effect of Flash Lamp–Pulsed Dye Laser on Psoriasis", Archives of Dermatology, vol. 128, Jun. 1992, pp. 853–855.

J.E. Rasmussen, "Effect of Flash Lamp Pulsed Tunable Dye Laser of Psoriasis", Abstract presented at the Hundred Twelfth Annual Meeting of the American Dermatological Association, Inc., Naples, Florida, 21–26 Feb. 1992.

J. Boulnois, "Photophysical Processes in Recent Medical Laser Developments: A Review", Lasers in Medical Science vol. 1 (1986) pp. 47–64.

E.K. Orenberg et al., "Comparison of heat delivery systems for hyperthermia treatment of psoriasis", Int. J. Hyperthermia, 1986 vol. 2, No. 3, pp. 231–241.

*Primary Examiner*—Jennifer Bahr
*Assistant Examiner*—Bryan K. Yarnell
*Attorney, Agent, or Firm*—Wolf, Greenfield & Sacks, P.C.

[57] ABSTRACT

The invention provides a method for selectively destroying blood vessels contained at a selected depth and in a selective area of a patients dermis by positioning a laser so that light from the laser will impinge on the selected area of the dermis and operating the laser to deliver pulse light to the area, which light has a wavelength between 700 nm and 1100 nm, with each pulse delivering a fluence at the surface above the area being treated of between 5 joules per square centimeter and 100 joules per square centimeter, and each pulse having a pulse duration of between 0.2 milliseconds and 100 milliseconds.

15 Claims, 3 Drawing Sheets

ID NO. 5,707,403

METHOD FOR THE LASER TREATMENT OF SUBSURFACE BLOOD VESSELS

RELATED APPLICATION

This application is a continuation in part of application Ser. No. 08/022,978 filed Feb. 24, 1993, now U.S. Pat. No. 5,527,350.

FIELD OF THE INVENTION

This invention relates to the field of laser dermatology and more particularly to a method for utilizing a laser to treat and selectively destroy blood vessels located at some depth below the surface of the skin.

BACKGROUND OF THE INVENTION

There are many conditions that dermatologists are called upon to treat which involve, either directly or indirectly, blood vessels located in the dermal skin layer at depths of up to several millimeters from the skin surface, which conditions can be relieved or cured by coagulating the blood in such vessels resulting in the destruction thereof. Such conditions include, but are by no means limited to, visible leg veins including varicose veins, telangiectasias (i.e., vascular lesions formed by dilation of small blood vessels which may appear in many parts of the body including the face; port wine stains, unwanted hair and psoriasis. In the case of unwanted hair, blood vessels in the base of the hair follicle (i.e., in the papillary bulb) feed the follicle, and if these blood vessels can be destroyed, there is a possibility that the follicle will also be destroyed resulting in the permanent removal of the hair growing therefrom. Similarly, there is evidence that the destruction of blood vessels underlying psoriatic plaque can alleviate the symptoms of psoriasis.

However, lasers which have heretofore been used for destruction of blood vessels have normally operated at wavelengths of slightly below 600 nm. This is because the absorption coefficient for blood drops off sharply at 600 nm, dropping by roughly two orders of magnitude between 580 and 700 nm. However, because of the high absorption of blood at, for example, 577 nm, the typical wavelength used for selective photothermolysis on dermal tissue, absorption of light by hemoglobin in blood, and also by melanin in the skin which also is highly absorbent at these wavelengths, causes much of the incident light to be absorbed within a few hundred microns of the skin surface, preventing such radiation from reaching deep vessels at a sufficient level to cause coagulation thereof. The scattering coefficient for tissue is also relatively large at these wavelengths further reducing light energy reaching deep vessels. If the fluence of the laser is increased in an effort to get sufficient energy to the deep vessels at wavelengths shorter than about 700 nm, the high fluence or energy can cause explosion of surface vessels and/or burning of the skin.

A need therefore exists for an improved method for treating dermatological conditions by destroying deep blood vessels, and in particular for an improved way of utilizing a laser to treat leg veins, telangiectasias and the like without resulting in significant injury to the skin surface.

SUMMARY OF THE INVENTION

In accordance with the above, this invention provides a method for selectively destroying blood vessels contained at a selected depth and in a selected area of a patient's dermis. The method involves the steps of aiming or positioning (hereinafter "positioning") a laser so that light from the laser will impinge upon the selected area of the dermis, and operating the laser to deliver pulsed light to the area, which light has a wavelength of between 700 nm and 1100 nm, with each pulse delivering a fluence at the surface above the area being treated of between 5 joules per square centimeter and 100 joules per square centimeter and each pulse having a pulse duration of between 0.2 milliseconds and 100 milliseconds. The surface area on which the light impinges may for example be between 0.1 square centimeters and 10 square centimeters. The laser may be operated to deliver a single pulse, or multiple pulses may be provided. The laser may also be a continuous-wave laser with pulse duration being controlled by gating the laser to provide the pulsed light, or the laser may be a high repetition rate laser with pulse duration again being controlled by gating the laser. The steps of positioning the laser and operating the laser may be repeated for additional areas of the dermis containing blood vessels to be destroyed until all such blood vessels have been destroyed. During the step of operating the laser, the depth to which vessels are destroyed may be controlled by controlling the fluence delivered by the laser; and the size of the blood vessels to be destroyed may be controlled by controlling the pulse durations.

The blood vessels to be destroyed, and at which the laser is positioned to impinge during the positioning step, may be leg veins, telangiectasias, part of a port wine stain, blood vessels at the base of a hair follicle, blood vessels underlying psoriatic plaque, or other subsurface blood vessels the destruction or elimination of which are desired, either for cosmetic reasons or to alleviate a health condition.

The foregoing and other objects, features and advantages of the invention will be apparent from the following more particular description of preferred embodiments of the invention as illustrated in the accompanying drawings.

IN THE DRAWINGS

DETAILED DESCRIPTION OF THE INVENTION

Figure 1:
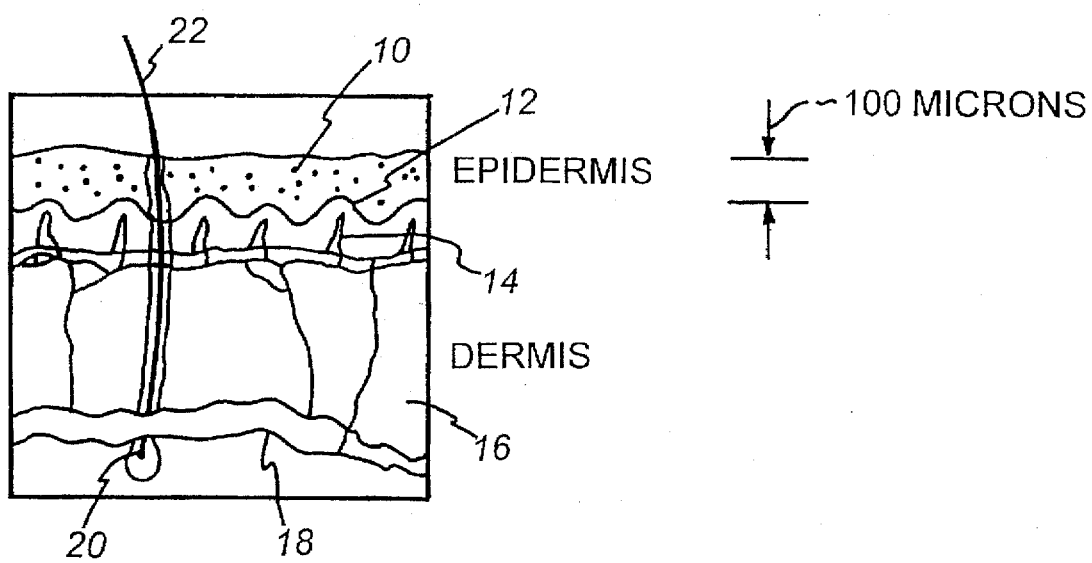
FIG. 1 is a sectional diagram of an illustrative skin area containing a hair follicle and blood vessels.

FIG. 1 illustrates the structure of the outer layers of a person's skin, with the surface epidermis layer 10 normally having a thickness of approximately 100 microns and the underlying dermis layer generally having a thickness of approximately 1.5 to 4 mm. Dermal papillae 12 are formed at the junction between these layers with capillary microvessels 14 being formed for the dermal papillae. Various veins or other blood vessels 18 pass through selected areas of the dermis at selected depths, which depths may vary from less than 1 mm to several mm. Hair follicles 20 may also be formed in the dermis and pass through the epidermis. Each hair follicle terminates in a bulb or papillae which among other things contains blood vessels which nourish the hair follicle.

For various reasons, it may be desirable to destroy the microvessels 14 or, more likely, the veins or other blood vessels 18. For example, the blood vessels 18 may become dilated to form telangiectasias or vascular lesions such as spider veins which, particularly if they occur in facial or leg areas can be cosmetically undesirable. Leg veins, particularly varicose veins, in addition to being cosmetically undesirable, can also be painful. Port wine stains are another cosmetic problem which can be alleviated by removing deep blood vessels. There is research to support the proposition that destruction of the elongated microvessels 14 which are formed under psoriatic plaque can result in alleviation of psoriatic symptoms and it has been suggested that destruction of the blood vessels in the papillary bulb of a hair follicle 20 can sufficiently damage or destroy the hair follicle so as to either prevent of significantly delay the regrowth of hair 22. There are also other conditions for which it may be desirable to destroy a blood vessel deep in the dermis 16.

Figure 2:
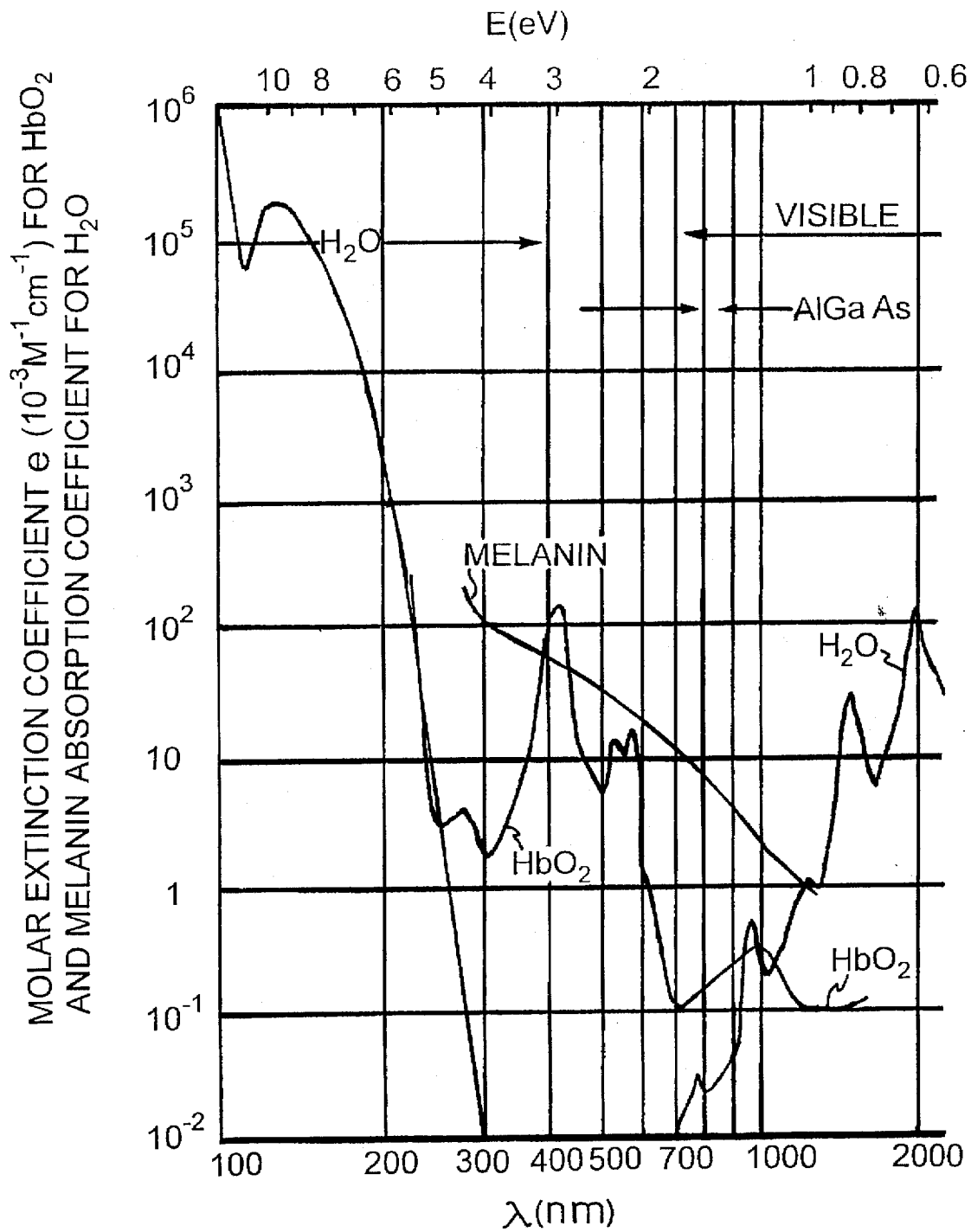
FIG. 2 is a diagram indicating absorption versus wavelength for various components of skin tissue.

However, to cause selective thermolysis or heating of blood vessels without collateral damage of surrounding tissues, substantial light energy must get through the epidermis and the dermis above the blood vessel without being excessively scattered or absorbed. However, transmission of light through human skin is largely determined by scattering and by the absorption of the various components within the tissue (e.g., hemoglobin, melanin and water). FIG. 2 is a plot indicating the absorption versus wavelength of tissue components, *Lasers in Medical Science* Vol. 1, (1986), pp. 47–66. Absorption varies over eight orders of magnitude for wavelengths ranging from 100 nm to 2000 nm. Because water is by far the largest single component of human tissue, the requirement for deep penetration through tissue (to depths of up to several millimeters) suggests wavelengths in the 300 nm to 1000 nm range, where water absorption is very low.

At wavelengths shorter that about 700 nm however, the absorption of light by melanin and by hemoglobin causes much of the incident light to be absorbed within a few hundred microns of skin surface. The effort to get sufficient energy to deep vessels at wavelengths shorter than about 700 nm can easily cause explosion of surface vessels and/or burning of the skin. Wavelengths in the 700 nm to 1100 nm range are preferred because skin tissue transmission at these wavelengths is high.

However, achievement of selective photothermolysis of blood in the near infrared region at wavelengths longer than 700 nm has been thought to be unachievable because of the very low absorption coefficient of blood in this wavelength band. At 800 nm, blood absorption is approximately 100 times less that at 577 nm, the typical wavelength used for selective photothermolysis on dermal tissue. Detailed analysis of remittance measurement on human skin however, reveals that absorption in the 700–1100 nm range due to other components of dermal tissue is extremely low. Detailed analysis of light propagation and absorption reveals that energy can be deposited into blood with remarkably high selectivity in the 700 to 1100 nm wavelength region, despite the fact that hemoglobin absorption is very low in this wavelength band. This results from the even lower absorption of other components in this region and also from the fact that the scattering coefficient of tissue in this region is often much lower than in the shorter wavelength visible region.

Therefore, in practicing this invention, a laser is selected which produces light in the 700–1100 nm wavelength region. Such a laser is preferably a diode laser, for example a commercially available AlGaAs semiconductor diode laser having an output wavelength of approximately 800 nm. However, other diode lasers or other lasers having outputs in the indicated range may also be utilized. Other lasers operating in the desired range include a ruby or other solid state laser or certain continuous wave lasers.

With a semiconductor diode array, a concentrator, which may be a solid or hollow rectangular light guide, may be utilized to direct the array output onto the treatment area, which area may be for example 0.5 $cm^2$ for certain applications. The treatment area will vary with application from approximately 0.1 $cm^2$ to 10 $cm^2$ and should normally be more than 0.4 $cm^2$ to avoid a significant reduction in local fluence in the tissue due to lateral beam spreading. Other suitable techniques known in the art, including the use of a fiber optic cable and/or applicator, may also be utilized to control the size of the treatment area depending on applications and the laser utilized.

While operating in the wavelength ranges indicated results in a significantly larger percentage of the light energy reaching the deep vessels, there is still some absorption and scattering of incident light so that there is still a decrease in available energy as the depth increases.

Figure 3A:
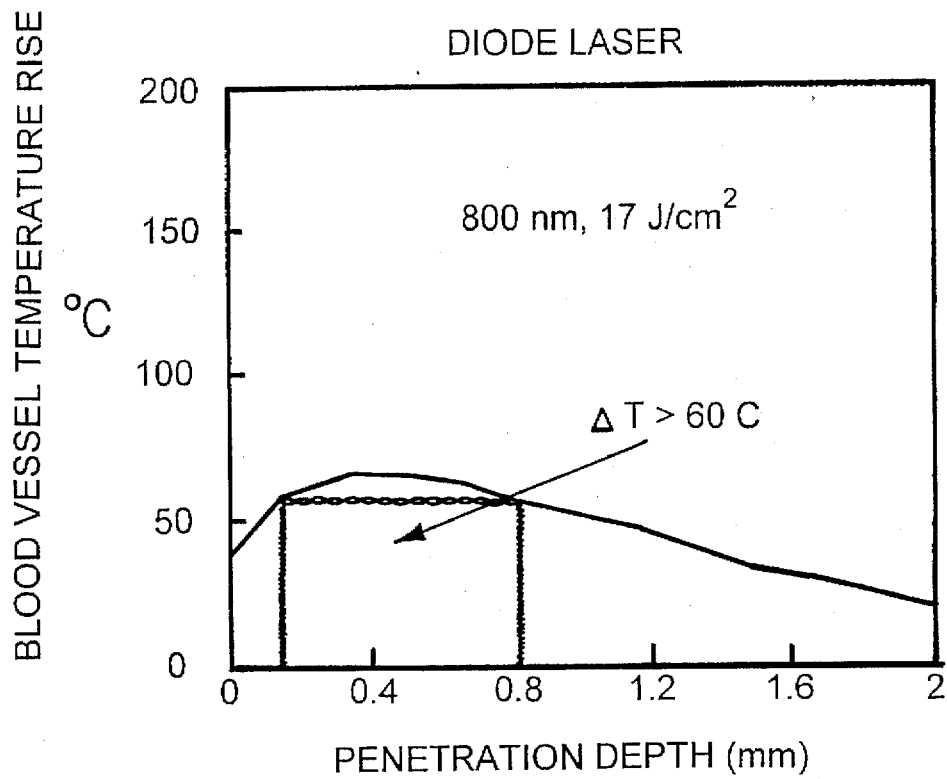
FIG. 3a is a diagram of blood vessel temperature rise as a function of vessel depth for a diode laser.
Figure 3B:
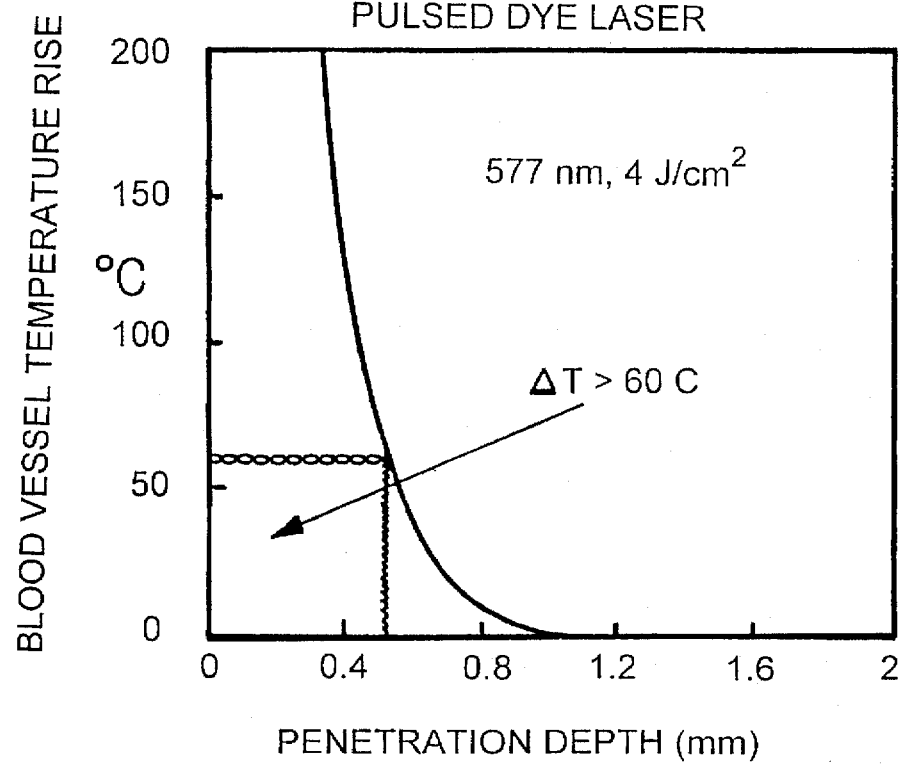
FIG. 3b is a diagram of blood vessel temperature rise as a function of vessel depth for a pulse dye laser.

This is illustrated in FIG. 3a which illustrates the blood vessel temperature rise as a function of increased depth for a diode laser operating at 800 nm with an incidence fluence of 17 $J/cm^2$ and a pulse duration of 5 ms. This can be contrasted with a temperature rise for a pulse dye laser operating at 577 nm and having a fluence of 4 $J/cm^2$ and a pulse duration of 360 μs, as shown in FIG. 3b. These are typical illumination conditions. The temperatures that are shown reflect the peak vessel temperature that is reached at the end of the laser illumination. Melanin and blood absorption being much lower at 800 nm permits much higher laser powers to be used without causing damage to the epidermis. From the figures the superiority of the longer wavelength for coagulating deep vessels can be seen, the 577 nm laser having an intensity characteristic of exponential absorption and providing high energy down to a depth of only approximately 0.5 mm, with little energy beyond 0.7 mm and essentially none beyond 1 mm. By contrast, at 800 nm light scattering can be much stronger than absorption (in the case illustrated, about a factor of 100×) and the illumination intensity is more characteristic of diffusion. The 800 nm diode laser therefore does not provide high heating at the surface, but continues to provide significant heating in this case, to a depth of approximately 1 mm., and is still providing reasonable heating out to 2 mm and beyond.

If it is assumed that a temperature rise to approximately 60° C. is required to coagulate blood, and therefore to destroy a blood vessel, then it can be seen from FIG. 3b that lasers operating in the conventional wavelength can only destroy blood vessels near the surface to a depth of approximately 0.5 mm, while a diode or other laser operating at the longer wavelength (i.e., approximately 800 nm) can, with the fluence shown, destroy blood vessels at approximately up to 1 mm for the case shown. However, if the fluence from the laser is increased, the light energy reaching the deeper vessels will also increase, permitting destruction of blood vessels at depths in excess of 1 mm to depths of 2 mm. In addition, in cases of somewhat lower scattering, heating at depths of several millimeters can be obtained with higher fluence. Such greater depths could for example be achieved with the application of energy of up to perhaps 50 $J/cm^2$ to the skin surface, with energies of up to 100 $J/cm^2$ and more being possible for some applications. The danger is that such high energy applied to the surface may cause damage to the skin. However, the low absorption of melanin to the radiation at 800 nm reduces epidermal damage and using a bleaching agent on the epidermis prior to treatment may further reduce the absorption of light by the epidermal layer, permitting higher energy to be utilized without surface damage. Surface damage may also be reduced by either pre-cooling the epidermis in the area to be treated and/or by cooling the epidermis during the application of laser energy thereto. Cooling during the application of the laser energy may for example be accomplished by applying the laser energy through an applicator in contact with the skin which applicator is cooled in suitable fashion. Where pressure is applied to the applicator, the distance between the surface and the blood vessel to be treated may be reduced and blood in the area between the surface and the vessels to be treated may be removed, permitting deeper blood vessels to be reached with sufficient energy to cause destruction thereof without resulting in significant damage to the epidermal layer.

Another factor which can be controlled is pulse duration. The time duration for illumination should be comparable to or shorter than the thermal relaxation time of the target. The objective is not to have the pulses so long as to cause excessive conduction of heat to tissues surrounding the target; however, since blood is more absorbent than surrounding tissues at the wavelengths being utilized, most of the energy should be absorbed by the blood vessels, permitting relatively long pulses to be utilized. If the pulse width is about equal to the thermal relaxation time of the target vessel, the laser energy may often be more easily generated. In addition, smaller vessels will experience less temperature rise than if a shorter pulse were used. For target blood vessels having a size of approximately 25 to 300 microns, corresponding pulse widths of between 1.0 milliseconds and 30 milliseconds (the pulse width increasing with the size of the vessels) have been found to be suitable. However, for larger blood vessels such as veins, a longer pulse duration, perhaps up to 100 milliseconds, may be desirable. Diode lasers can be operated for any desired pulse duration in the ranges indicated. For a CW laser or a high repetition rate laser, a gating technique, either electronic or optical, may be utilized to achieve the desired pulse width. For example, an optical shutter or mechanical shutter could be utilized to control the duration of the pulse applied to the target area.

While single pulse operation has been discussed above, it is apparent that multiple pulses could be applied to the same area, which pulses are spaced by, for example, one second to as little as 10 ms to assure destruction of the desired blood vessel. Further, since the treatment area is generally relatively small, it may be necessary to adjust the position of the laser, of the target area, of aiming optics for the laser or of an applicator fed by the laser so as to successively treat different relatively small areas until the entire area requiring treatment has been treated. Such repositioning may be done manually or may be accomplished under some type of automatic control.

A method has thus been provided for effectively destroying and eliminating blood vessels in the legs and other parts of the body to treat a variety of cosmetic and medical problems with minimal damage to the overlying epidermis. While specific lasers and techniques for the utilization thereof have been discussed above, specific parameters have been provided above and specific conditions which the method may be utilized to treat have been indicated above, these have been provided for purposes of illustration only and other changes in form and detail may be made in the invention by those skilled in the art while still remaining within the spirit and scope of the invention. The invention is therefore only to be limited only by the following claims.

What is claimed is:

1. A method for destroying blood vessels contained at a selected depth and in a selected area of the dermis comprising the steps of:

(a) positioning a laser so that light from said laser will impinge upon said selected area of the dermis; and (b) operating said laser to deliver at least one light pulse to said area having a wavelength between 700 nm and 1100 nm, with each pulse delivering a fluence at a skin surface above said area of between 5 joules per square centimeter and 100 joules per square centimeter and each pulse having a pulse duration of between 0.2 millisecond and 100 milliseconds.

2. The method of claim 1 wherein said light impinges upon an area at said surface of between 0.1 square centimeter and 10 square centimeters.

3. The method of claim 1 wherein, during step (b) said laser is operated to deliver a single pulse.

4. The method of claim 1 including the step of repeating steps (a) and (b) for additional areas of the dermis containing blood vessels to be destroyed.

5. The method of claim 1 wherein step (b) includes the step of controlling the fluence delivered by the laser to said surface to control said selected depth.

6. The method of claim 1 wherein step (b) includes the step of controlling the pulse duration depending on the size of the blood vessel to be destroyed.

7. The method of claim 1 wherein said pulse duration is between 1.0 milliseconds and 30 milliseconds.

8. The method of claim 1 wherein the laser is a continuous wave laser and wherein step (b) includes the step of gating the laser to provide the pulsed light.

9. The method of claim 1 wherein the laser is a high repetition laser and wherein step (b) includes the step of gating the laser to provide the pulsed light.

10. The method of claim 1 wherein said blood vessels are leg veins and wherein step (a) includes the step of positioning the laser at a portion of said leg vein which is to be treated and destroyed.

11. The method of claim 1 wherein said blood vessels are telangiectasias and wherein step (a) includes the step of positioning the laser at a portion of said telangiectasias which is to be treated and destroyed.

12. The method of claim 1 wherein said blood vessels are port wine stains and wherein step (a) includes the step of positioning the laser over a portion of said port wine stains which are to be treated and destroyed.

13. The method of claim 1 wherein said blood vessels are at the base of hair follicles and wherein step (a) includes the step of positioning the laser over a portion of said hair follicles which are to be treated and destroyed.

14. The method of claim 1 wherein said blood vessels underline psoriatic plaque and wherein step (a) includes the step of positioning the laser over a portion of said psoriatic plaque which are to be treated and destroyed.

15. A method for selectively destroying veins contained at a selected depth and in a selected area of the dermis of a person's leg comprising the steps of:

(a) positioning a laser so that light from said laser will impinge upon said dermis of a person's leg in said selected area; and (b) operating said laser to deliver at least one light pulse having a wavelength between 700 nm and 1100 nm, each pulse delivering a fluence at a skin surface above said area of between 5 joules per square centimeter and 100 joules per square centimeter and each pulse having a pulse duration of between 0.2 millisecond and 100 milliseconds.

* * * * *

(12) EX PARTE REEXAMINATION CERTIFICATE (6747th)
United States Patent
Grove et al.

(10) Number: US 5,707,403 C1
(45) Certificate Issued: Apr. 7, 2009

(54) METHOD FOR THE LASER TREATMENT OF SUBSURFACE BLOOD VESSELS

(75) Inventors: Robert E. Grove, Pleasanton, CA (US); James Z. Holtz, Livermore, CA (US)

(73) Assignee: ESC Medical Systems, Inc., Norwood, MA (US)

Reexamination Request:
No. 90/010,067, Dec. 5, 2007

Reexamination Certificate for:
Patent No.: 5,707,403
Issued: Jan. 13, 1998
Appl. No.: 08/636,286
Filed: Apr. 23, 1996

Related U.S. Application Data

(63) Continuation-in-part of application No. 08/022,978, filed on Feb. 24, 1993, now Pat. No. 5,527,350.

(51) Int. Cl.
*A61N 5/06* (2006.01)

(52) U.S. Cl. .................. 607/89; 606/3; 606/9
(58) Field of Classification Search .............. None
See application file for complete search history.

(56) References Cited

U.S. PATENT DOCUMENTS

| | | | |
|---|---|---|---|
| 2,716,698 A | 8/1955 | Brukner | 240/1 |
| 2,954,771 A | 10/1960 | Boyan | 128/396 |
| 3,327,712 A | 6/1967 | Kaufman et al. | 128/398 |
| 3,693,623 A | 9/1972 | Harte et al. | 128/303.1 |
| 3,834,391 A | 9/1974 | Block | 128/303.1 |
| 3,930,504 A | 1/1976 | de Laforcade | 128/303.1 |
| 4,229,658 A | 10/1980 | Gonser | 250/504 H |
| 4,233,493 A | 11/1980 | Nath | 219/354 |
| 4,283,661 A | 8/1981 | Doty | 315/360 |
| 4,321,930 A | 3/1982 | Jobsis et al. | 128/633 |
| 4,366,570 A | 12/1982 | Bees | 372/70 |
| 4,380,240 A | 4/1983 | Jobsis et al. | 128/633 |
| 4,388,924 A | 6/1983 | Weissman et al. | 128/303.1 |
| 4,444,190 A | 4/1984 | Mutzhas | 128/396 |
| 4,497,018 A | 1/1985 | Rice | 363/96 |
| 4,506,196 A | 3/1985 | Bees | 315/241 R |
| 4,539,987 A | 9/1985 | Nath et al. | 128/303.1 |
| 4,564,011 A | 1/1986 | Goldman | 128/303.1 |
| 4,645,980 A | 2/1987 | Yang | 315/159 |
| 4,647,830 A | 3/1987 | Bees | 320/1 |
| 4,653,495 A | 3/1987 | Nanaumi | 128/303.1 |
| 4,672,969 A | 6/1987 | Dew | 128/397 |
| 4,726,377 A | 2/1988 | Jegers et al. | 128/376 |
| 4,729,375 A | 3/1988 | Jegers et al. | 128/376 |
| 4,733,660 A | 3/1988 | Itzkan | 128/303.1 |
| 4,775,361 A | 10/1988 | Jacques et al. | 604/20 |
| 4,810,658 A | 3/1989 | Shanks et al. | 436/172 |
| 4,835,749 A | 5/1989 | Welton | 368/10 |

(Continued)

FOREIGN PATENT DOCUMENTS

| | | |
|---|---|---|
| DE | 27 17 421 A1 | 11/1978 |
| SE | 465 953 B | 11/1991 |
| WO | WO 89/00871 | 2/1989 |
| WO | WO 90/14836 | 12/1990 |
| WO | WO 91/15264 | 10/1991 |
| WO | WO 98/52645 | 11/1998 |

OTHER PUBLICATIONS

Achauer et al., "Argon Laser Treatment of Telangiectasia of the Face and Neck: 5 Years' Experience", *Lasers Surg. Med.*, 7:495–498 (1987).

(Continued)

*Primary Examiner*—Beverly M. Flanagan

(57) ABSTRACT

The invention provides a method for selectively destroying blood vessels contained at a selected depth and in a selective area of a patients dermis by positioning a laser so that light from the laser will impinge on the selected area of the dermis and operating the laser to deliver pulse light to the area, which light has a wavelength between 700 nm and 1100 nm, with each pulse delivering a fluence at the surface above the area being treated of between 5 joules per square centimeter and 100 joules per square centimeter, and each pulse having a pulse duration of between 0.2 milliseconds and 100 milliseconds.

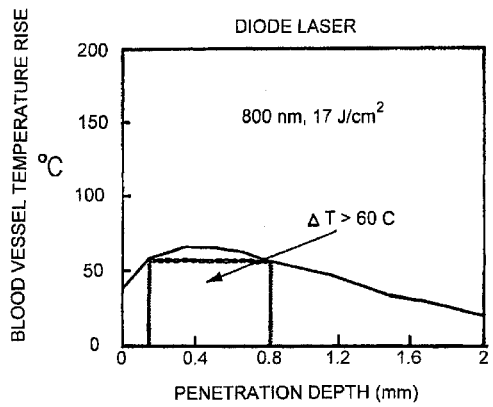

U.S. PATENT DOCUMENTS

| | | | | |
|---|---|---|---|---|
| 4,839,562 | A | 6/1989 | Francis et al. | 315/149 |
| 4,851,738 | A | 7/1989 | Yang | 315/159 |
| 4,871,559 | A | 10/1989 | Dunn et al. | 426/248 |
| 4,884,568 | A | 12/1989 | Hahn | 128/303.1 |
| 4,938,221 | A | 7/1990 | Tuffel | 128/401 |
| 4,947,859 | A | 8/1990 | Brewer et al. | 128/715 |
| 5,008,579 | A | 4/1991 | Conley et al. | 310/303 |
| 5,020,995 | A | 6/1991 | Levy | 433/215 |
| 5,034,235 | A | 7/1991 | Dunn et al. | 426/238 |
| 5,054,488 | A | 10/1991 | Muz | 128/633 |
| 5,059,192 | A | 10/1991 | Zaias | 606/9 |
| 5,066,293 | A | 11/1991 | Furumoto | 606/9 |
| 5,071,422 | A | 12/1991 | Watson et al. | 606/128 |
| 5,113,462 | A | 5/1992 | Clancy et al. | 385/53 |
| 5,125,922 | A | 6/1992 | Dwyer et al. | 606/3 |
| 5,126,621 | A | 6/1992 | Morton et al. | 313/237 |
| 5,194,723 | A | 3/1993 | Cates et al. | 250/205 |
| 5,204,517 | A | 4/1993 | Cates et al. | 250/205 |
| 5,226,107 | A | 7/1993 | Stern et al. | 392/416 |
| 5,269,778 | A | 12/1993 | Rink et al. | 606/12 |
| 5,281,798 | A | 1/1994 | Hamm et al. | 250/205 |
| 5,290,273 | A | 3/1994 | Tan | 606/9 |
| 5,290,274 | A | 3/1994 | Levy et al. | 606/13 |
| 5,312,395 | A | 5/1994 | Tan et al. | 606/9 |
| 5,320,618 | A | 6/1994 | Gustafsson | 606/9 |
| 5,328,488 | A | 7/1994 | Daikuzono | 606/16 |
| 5,328,517 | A | 7/1994 | Cates et al. | 134/7 |
| 5,337,741 | A | 8/1994 | Diamond | 600/8 |
| 5,344,418 | A | 9/1994 | Ghaffari | 606/9 |
| 5,344,433 | A | 9/1994 | Talmore | 607/88 |
| 5,374,265 | A | 12/1994 | Sand | 606/5 |
| 5,400,791 | A | 3/1995 | Schlier et al. | 128/664 |
| 5,423,803 | A | 6/1995 | Tankovich et al. | 606/9 |
| 5,445,146 | A | 8/1995 | Bellinger | 607/89 |
| D363,349 | S | 10/1995 | Dittert | D24/158 |
| 5,474,528 | A | 12/1995 | Meserol | 604/20 |
| 5,489,279 | A | 2/1996 | Meserol | 604/290 |
| 5,522,814 | A | 6/1996 | Bernaz | 606/36 |
| 5,546,214 | A | 8/1996 | Black et al. | 359/203 |
| 5,558,666 | A | 9/1996 | Dewey et al. | 606/9 |
| 5,595,568 | A | 1/1997 | Anderson et al. | 606/9 |
| 5,618,284 | A | 4/1997 | Sand | 606/5 |
| 5,725,565 | A | 3/1998 | Smith | 607/88 |
| 5,755,753 | A | 5/1998 | Knowlton | 607/98 |
| 5,814,040 | A | 9/1998 | Nelson et al. | 606/9 |
| 5,817,089 | A | 10/1998 | Tankovich et al. | 606/9 |
| 5,817,090 | A | 10/1998 | Abergel et al. | 606/9 |
| 5,843,143 | A | 12/1998 | Whitehurst | 607/88 |
| RE36,634 | E | 3/2000 | Ghaffari | 606/9 |
| 6,171,332 | B1 | 1/2001 | Whitehurst | 607/89 |

OTHER PUBLICATIONS

Alora et al., "Recent Developments in Cutaneous Lasers", *Lasers Surg. Med.,* 26:108–118 (2000).

Alster et al., "Treatment of Port–Wine Stains with the Flashlamp–pumped Pulsed Dye Laser: Extended Clinical Experience in Children and Adults", *Ann. Plast. Surg.,* 32(5):478–484 (1994).

Altshuler et al., "Extended Theory of Selective Photothermolysis", *Lasers Surg. Med.,* 29:416–432 (2001).

Ambrose et al., "Prospective randomized comparison of photocoagulation and rubber band ligation in treatment of haemorrhoids", *Br. Med. J.,* 286:1389–1391 (1983).

Anderson et al., "Mechanisms of Selective Vascular Changes Caused by Dye Lasers",*Lasers Surg. Med.,* 3:211–215 (1983).

Anderson et al., "Microvasculature Can Be Sensitively Damaged Using Dye Lasers: A Basic Theory and Experimental Evidence in Human Skin",*Lasers Surg. Med.,* 1:263–276 (1981).

Anderson et al., "Selective Photothermolysis: Precise Microsurgery by Selective Absorption of Pulsed Radiation", *Science,* 220:524–527 (1983).

Anderson, T.F., "Light Sources in Photomedicine", in *Clinical Photomedicine,* Chapter 3, pp. 37–58, Marcel Dekker, Inc., New York (1993).

Angermeier, M.C., "Treatment of facial vascular lesions with intense pulsed light",*J. Cutan. Laser Ther.,* 1:95–100 (1999).

Anvari et al., "Selective cooling of biological tissues: application for thermally mediated therapeutic procedures", *Phys. Med. Biol.,* 40:241–252 (1995).

Apfelberg et al., "Comparison of Argon and Carbon Dioxide Laser for Treatment of Decorative Tattoos Clinical and Pathological Observations", *Lasers Surg. Med.,* 3:183 (Abstract No. 294) (1983).

Apfelberg et al., Dot or Pointillistic Method for Improvement in Results of Hypertrophic Scarring in the Argon Laser Treatment of Portwine Hemangiomas,*Lasers Surg. Med.,* 6:552–558 (1987).

Apfelberg et al., "Investigation of YAG Laser Uses in Plastic Surgery", *Lasers Surg.,* 6:246 (Abstract No. 77) (1986).

Apfelberg et al., "Preliminary Investigation of KTP/532 Laser Light in the Treatment of Hemangiomas and Tattoos", *Lasers Surg. Med.,* 6:38–42 (1986).

Apfelberg et al., "Progress Report on Extended Clinical Use of the Argon Laser for Cutaneous Lesions", *Lasers Surg. Med.,* 1:71–83 (1980).

Apfelberg et al., "Progress Report on Multicenter Study of Laser–Assisted Liposuction", *Aesth. Plast. Surg.,* 18:259–264 (1994).

Apfelberg et al., "Results of Argon and CO2 Laser Exposure of Telangiectasia of the Lower Extremity: A Preliminary Report", *Lasers Surg. Med.,* 3:149 (Abstract No. 165) (1983).

Apfelberg et al., "Study of Three Laser Systems for Treatment of Superficial Varicosities of the Lower Extremity", *Lasers Surg. Med.,* 7:219–223 (1987).

Apfelberg et al., "Superpulse $CO_2$ Laser Treatment of Facial Syringomata", *Lasers Surg. Med.,* 7:533–537 (1987).

Apfelberg et al., "Update on Laser Usage in Treatment of Decorative Tattoos", *Lasers Surg. Med.,* 2:169–177 (1982).

Apfelberg, D.B., "Intralesional Laser Photocoagulation—Steroids as an Adjunct to Surgery for Massive Hemangiomas and Vascular Malformations",*Ann. Plast. Surg.,* 35:144–148 (1995).

Ara et al., "Irradiation of Pigmented Melanoma Cells with High Intensity Pulsed Radiation Generates Acoustic Waves and Kills Cells", *Lasers Surg. Med.,* 10:52–59 (1990).

Ashinoff et al., "Cappillary Hemangiomas and Treatment with the FlashLamp–Pumped Pulsed Dye Laser", *Arch. Dermatol.,* 127:202–205 (1991).

Ashinoff et al., "Flashlamp–pumped pulsed dye laser for port–wine stains in infancy: Earlier versus later treatment", *J. Am. Acad. Dermatol.,* 24:467–472 (1991).

Bell et al., "100 µsec pulsed $CO_2$ laser resurfacing of lower eyelids: Erythema and rhytides reduction", *SPIE,* 2970:360–366 (1997).

Broska et al., "Comparison of the Argon Tunable Dye Laser with the Flashlamp Pulsed Dye Laser in Treatment of Facial Telangiectasia", *J. Dermatol. Surg. Oncol.*, 20:749–753 (1994).

Brugmans et al., "Temperature Response of Biological Materials to Pulsed Non–Ablative $CO_2$ Laser Irradiation", *Lasers Surg. Med.*, 11:587–594 (1991).

Burson et al., "Gel de Transmission de Ultrasonidos: Estudio Comparitivo de Distintas Formulaciones", *Farm Hosp.*, pp. 394–399 (1991) (in Spanish, with English Abstract Only).

Cates, M.C., "A long pulse (5μs) e–beam pumped XeF laser", *SPIE*, 1225:34–43 (1990).

Cates, M.C., "Excimer laser produced plasma studies", *SPIE*, 1279:102–111 (1990).

Chess et al., "Cool Laser Optics Treatment of Large Telangiectasia of the Lower Extremities", *J. Dermatol. Surg. Oncol.*, 19:74–80 (1993).

Chissler et al., "Tanning Beds Are Not Without Drawbacks", *FDA Consumer*, pp. 21–22 (1984).

Cliff et al., "Treatment of mature port wine stains with the PhotoDerm VL", *J. Cutan. Laser Ther.*, 1:101–104 (1999).

Cole–Beuglet et al., "Ultrasound mammography for the Augumented Breast", *Radiology*, 146:737–742 (1983).

Colver et al., "Port Wine Stains", *J. Roy. Soc. Med.*, 80:603 (1987).

Colver et al., "Precise dermal damage with an infrared coagulator", *Br. J. Dermatol.*, 114:603–608 (1986).

Colver et al., "Tattoo removal using infra–red coagulation", *Br. J. Dermatol*, 112:481–485 (1985).

Colver G.B., "The Infrared Coagulator in Dermatology", *Dermatologic Clinics*, 7(1):155–167 (1989).

Daniell et al., "A History of Photodynamic Therapy", *Aust. N. Z. J. Surg.*, 61:340–348 (1991).

Denham et al., "Light Distribution in Laser Irradiated Tissue", *Lasers Surg. Med.*, 5:141 (Abstract No. 21) (1985).

Dzubow et al., "Leg Veins and Stretch Marks", *Am. Soc. Dermatol. Surg.*, 22:321 (1996).

Efthymiopoulos et al., "High–energy Short–pulse Flashlamps: Operating Characteristics", *Applied Optics*, 16:70–75 (1977).

Ell et al., "Laser Lithotripsy of Gallstone by Means of a Pulsed Neodymium YAG Laser—In Vitro and Animal Experments", *Endoscopy*, 18:92–94 (1986).

Englehardt et al., "Spectroscopy During Laser Induced Shock Wave Lithotripsy", *SPIE*, 906:200–204 (1988).

Fitzpatrick et al., "Flashlamp–pumped Pulsed Dye Laser Treatment of Port–Wine Stains", *J. Dermatol. Surg. Oncol.*, 20:743–748 (1994).

Fitzpatrick et al., "Treatment of Leg Veins: A Comparison of Laser Therapy with a Noncoherent, Multiwave Light Source", *Proc. Ann. Meeting IEEE Lasers & Electro–Optics Soc*, pp. 238–239 (1993).

Flock et al., "Er:YAG Laser–Induced Changes in Skin In Vivo And Transdermal Drug Delivery", *SPIE*, 2970:374–379 (1997).

Flock et al., "Thermal Damage of Blood Vessels in Rat Skin–flap Window Chamber Using Indocyanine Green and a Pulsed Alexandrite Laser: A Feasibility Study", *Lasers Med. Sci.*, 8:185–196 (1993).

Foster et al., "The Successful Use of the PhotoDerm VL in the Treatment of a Cavernous Hemangioma in a Dark–Skinned Infant", *Minimally Invasive Surgical Nursing*, 10:102–104 (1996).

Garden et al., "Effect of Dye Laser Pulse Duration on Selective Cutaneous Vascular Injury", *J. Invest. Dermatol.*, 87(5):653–657 (1986).

Garden et al., "The Treatment of Port–wine Stains by the Pulsed Dye Laser: Analysis of Pulse Duration and Long–term Therapy", *Arch. Dermatol.*, 124:889–896 (1988).

Geronemus et al., "The Medical Necessity of Evaluation and Treatment of Port–Wine Stains", *J. Dermatol. Surg. Oncol.*, 17:76–79 (1991).

Gijsbers et al., "CW Laser Ablation Velocities as a Function of Absorption in an Experimental One–Dimensional Tissue Model", *Laser Surg. Med.*, 11:287–296 (1991).

Gijsbers et al., "Effect of Force on Ablation Depth for a XeCl Excimer Laser Beam Delivered by an Optical Fiber in Contact with Arterial Tissue Under Saline", *Lasers Surg. Med.*, 12:576–584 (1992).

Gilbert, D.J., "Incorporating Photodynamic Therapy Into a Medical and Cosmetic Dermatology Practice", *Dermatol. Clin.*, 25:111–118 (2007).

Gold et al., "5–Aminolevulinic Acid Photodynamic Therapy: Where We Have Been and Where We Are Going", *Dermatol. Surg.*, 30:1077–1084 (2004).

Gold et al., "One–Year Follow–Up Using an Intense Pulsed Light Source for Long–Term Hair Removal", *J. Cutan. Laser Ther.*, 1:167–171 (1999).

Gold et al., "Treatment of Wrinkles and Skin Tightening Using Aluma™ Skin Renewal System with FACES™ (Functional Aspiration Controlled Electrothermal Stimulation) Technology", *Aesthetic Buyers Guide*, pp. 1–6 (2005).

Gold, M.H., "Aminolevulinic Acid Photodynamic Therapy: Medical Evidence for Its Expanded Use", *Expert Rev. Med. Devices*, 3:357–371 (2006).

Gold, M.H., "Introduction to Photodynamic Therapy: Early Experience", *Dermatol. Clin.*, 25:1–4 (2007).

Goldberg et al., "Nonablative Treatment of Rhytids With Intense Pulsed Light", *Lasers Surg. Med.*, 26:196–200 (2000).

Goldberg et al., "Q–switched Nd:YAG Laser: Rhytid Improvement by Non–Ablative Dermal Remodeling", *J. Cutan. Laser Ther.*, 2:157–160 (2000).

Goldberg, D.J., "Effect of Temperature–Controlled Cooling on Light–Based Skin Treatments", *J. Cos. Laser Ther.*, 8:155–156 (2006).

Goldberg, D.J., "Erbium: YAG Laser Resurfacing; What Is Its Role?", *Aesth. Surg. J.*, 18(4):255–260 (1998).

Goldberg, D.J., "New Collagen Formation After Dermal Remodeling with an Intense Pulsed Light Source", *J. Cutan. Laser Ther.*, 2:59–61 (2000).

Goldman et al., "600 nm Flash Pumped Dye Laser for Fragile Telangiectasia of the Elderly", *Lasers Surg. Med.*, 13:227–233 (1993).

Goldman et al., "Photothermal Sclerosis of Leg Veins", *Dermatol. Surg.*, 22:323–330 (1996).

Goldman et al., "Pulsed dye laser treatment of telangiectases with and without subtherapeutic sclerotherapy", *J. Am. Acad. Dermatol.*, 23(1):23–30 (1990).

Goldman et al., "Treatment of Cutaneous Vascular Lesions", in *Cutaneous Laser Surgery*, Chapter 2, pp. 19–105 (1994).

Goldman et al., "Treatment of port–wine stains (capillary malformation) with the flashlamp–pumped pulsed dye laser", *J. Pediatrics*, 122(1):71–77 (1993).

Goldman, M.P., "Laser and Noncoherent Pulsed Light Treatment of Leg Telangiectasia and Venules", *Cos. Dermatol.*, 8(10):43–44 (1995).

Goldman, M.P., "Sclerotherapy Treatment for Varicose and Telangiectatic Leg Veins", in *Vascular and Pigmented Abnormalities*, Chapter 17, pp. 256–271 (1997).

Gomer, H., "Military laser burns away skin flaws", *The London Sunday Times*, No. 8929 (Oct. 15, 1995).

Gonzalez et al., "Treatment of telangiectases and other benign vascular lesions with the 577 nm pulsed dye laser", *J. Am. Acad. Dermatol.*, 27(2):220–226 (1992).

Gregory et al., "Effect of Blood Upon the Selective Ablation of Atherosclerotic Plaque with a Pulsed Dye Laser", *Lasers Surg. Med.*, 10:533–543 (1990).

Grevelink et al., "Update on the Treatment of Benign Pigmented Lesions with the Q–Switched Ruby Laser", *Lasers Surg. Med.*, 4:73–74 (Abstract No. 326) (1992).

Groot et al., "Comparison of the infrared coagulator and the carbon dioxide laser in the removal of decorative tattoos", *J. Am. Acad. Dermatol.*, 15:518–522 (1986).

Gustafsson et al., "A Variable Pulsewidth Vascular System for Dermatology", *SPIE*, 2128:188–196 (1994).

Guttman, C., "Novel radiofrequency–based treatment achieves skin tightening with minimal discomfort", http://www.modernmedicine.com, pp. 1–3 (2005).

Harris et al., "Facial skin resurfacing with a very short pulsed $CO_2$ laser: Beam characterization and initial histological results", *SPIE*, 2671:211–218 (1996).

Henderson, B.W., "Photodynamic therapy—coming of age", *Photodermatology*, 6:200–211 (1989).

Henning et al., "Clinical and Histological Evaluation of Portwine Stain Treatment with a Microsecond pulsed Dye–laser at 577 NM", *Lasers Surg. Med.*, 4:375–380 (1984).

Henning et al., "Port Wine Stain Coagulation Experiments with a 540–nm Continuous Wave Dye–laser", *Lasers Surg. Med.*, 2:205–210 (1983).

Henning et al., "Rhinophyma Treated by Argon Laser", *Lasers Surg. Med.*, 2:211–215 (1983).

Henning et al., "Treatment of Keloids and Hypertrofic Scars with an Argon Laser", *Lasers Surg. Med.*, 6:72–75 (1986).

Hilsenrath, J.E., "Investing it; Unsightly Veins? Zap. Wall St. Woes? Zap.", *New York Times*, http://www.nytimes.com, pp. 1–3 (Jun. 23, 1996).

Hruza et al., "Laser Skin Resurfacing", *Arch. Dermatol.*, 132:451–455 (1996).

Hughes, P.S.H., "Multiple Miliary Osteomas of the Face Ablated With the Erbium: YAG Laser", *Arch. Dermatol.*, 135:378–380 (1999).

"Infrared–Coagulator", Lumatec product leaflet, pp. 1–4.

Ishimaru, A., "Diffusion of light in turbid material", *Applied Optics*, 28(12):2210–2215 (1989).

Jacques, S.L., "The Role of Skin Optics in Diagnostic and Therapeutic Uses of Lasers", *Lasers Dermatol.*, pp. 1–21 (1992).

Jaitly et al., "1 MV Long Pulse Generator with Low Ripple and Low Droop", *8th IEEE Int'l Pulsed Power Conf.*, pp. 161–165 (1991).

Jaitly et al., "Design and Testing of Multi–output 300kV Prototype Induction Cell Pulsed Power Supply for Darht", *10th IEEE Int'l Pulsed Power Conf.*, pp. 1412–1421 (1995).

Jay, H.H., "Victory Over Veins", http://www.nytimes.com, pp. 1–2 (Jul. 21, 1996).

Johannigmann et al., "Ein Neues Ultraschall–Kontaktgel", *Geburtsh. U. Frauenheilk*, p. 34 (1974) (in German, with English Abstract Only).

Kalka et al., "Photodynamic Therapy in Dermatology", *J. Am. Acad. Dermatol.*, 42:389–413 (2000).

Kaminester, L.H., "Suntanning Centers"; *JAMA*, 244(11):1258–1259 (1980).

Kaufmann et al., "Pulsed 2·94–μm erbium–YAG laser skin ablation—experimental results and first clinical application", *Clin. Exp. Dermatol.*, 15:389–393 (1990).

Keijzer et al., "Laser Beam Diameter for Port Wine Stain Treatment", *Lasers Surg. Med.*, 11:601–605 (1991).

Kennedy et al., "Photodynamic Therapy with Endogenous Protoporphyrin, IX: Basic Principles and Present Clinical Experience", *J. of Photochem. Photobio.*, 6:143–148 (1990).

Kilmer et al., "Pulse Dye Laser Treatment of Rhytids", *Lasers Surg. Med.*, p. 44 (Abstract No. 194) (1997).

Koechner, W., in *Solid State Laser Engineering*, Springer Series in Optical Sciences—vol. 1, Chapters 1–2, pp. 1–620, Springer–Verlag, New York (1976).

Lakmaker et al., "Modeling the Color Perception of Port Wine Stains and its Relation to the Depth of Laser Coagulated Blood vessels", *Lasers Surg. Med.*, 13:219–226 (1993).

Lash et al., "How We Got Here", *Lasers Surg. Med.*, 3:113 (Abstract No. 29) (1983).

Lask et al., "Laser Skin Resurfacing with the SikTouch Flashscanner for Facial Rhytides", *Dermatol. Surg.*, 21:1021–1024 (1995).

Lask et al., "Nonablative laser treatment of facial rhytides", *SPIE*, 2970:338–349 (1997).

Levins et al., "Q–Switched Ruby Laser Treatment of Tattoos", *Lasers Surg Med.*, Suppl. 3:63–64 (Abstract No. 255) (1991).

Lowe et al., "Skin Resurfacing with the Ultrapulse Carbon Dioxide Laser", *Dermatol. Surg.*, 21:1025–1029 (1995).

Magee et al., "Vein Marking Through Ultrasound Coupling Gel", *Eur. J. Vas. Surg.*, 4:491–492 (1990).

Majaron et al., "Deep Coagulation of Dermal Collagen with Repetitive Er:YAG Laser Irradiation", *Lasers Surg. Med.*, 26:215–222 (2000).

Majaron et al., "Er:YAG Laser Skin Resurfacing Using Repetitive Long–Pulse Exposure and Cryogen Spray Cooling: I. Histological Study", *Lasers Surg. Med.*, 28:121–130 (2001).

Majaron et al., "Er:YAG Laser Skin Resurfacing Using Repetitive Long–Pulse Exposure and Cryogen Spray Cooling: II. Theoretical Analysis", *Lasers Surg. Med.*, 28:131–137 (2001).

Margolis et al., "Visible Action Spectrum for Melanin–Specific Selective Photothermolysis", *Lasers Surg. Med.*, 9:389–397 (1989).

Marhic et al., "White–Light Flashlamp–pumped dye laser for photography through endoscopes", *Optics Communications*, 45(1):21–25 (1983).

McCaughan et al., "Photodynamic Therapy for Cutaneous and Subcutaneous Malignant Neoplasms", *Arch. Surg.*, 124:211–216 (1989).

McCaughan et al., "Photodynamic Therapy: An Eight–Year Experience", in *Photodynamic Therapy: Basic Principles and Clinical Applications*, pp. 323–331 (1992).

Meijering et al., "Limits of Radial Time Constants to Approximate Thermal Response of Tissue", *Lasers Surg. Med.*, 13:685–687 (1993).

Miller et al., "Optical Modelling of Light Distributions in Skin Tissue Following Laser Irradiation", *Lasers Surg. Med.*, 13:565–571 (1993).

Milner et al., "Analysis of nonablative skin resurfacing", *SPIE*, 2970:367–373 (1997).

Mordon et al., "Rationale for Automatic Scanners in Laser Treatment of Port wine Stains", *Lasers Surg. Med.*, 13:113–123 (1993).

Morelli et al., "Tunable Dye Laser (577 nm) Treatment of Port Wine Stains",*Lasers Surg. Med.*, 6:94–99 (1986).

Motamedi et al., "Thermal Response of Tissue During Laser Angioplasty", *Lasers Surg. Med.*, 5:172 (Abstract No. 114) (1985).

Mutzhas et al., "A New Apparatus with High Radiation Energy Between 320–460 nm: Physical Description and Dermatological Applications", *J. Invest. Dermatol.*, 76:42–47 (1981).

Nakagawa et al., "Ultrastructural Changes in Human Skin After Exposure to a Pulsed Laser",*J. Invest. Dermatol.*, 84(5):396–400 (1985).

Nestor et al., "New Perspectives on Photorejuvenation", *Skin & Aging*, 11:68–74 (2003).

Newman et al., "Variable Pulse Erbium: YAG Laser Skin Resurfacing of Perioral Rhytides and Side–by–side Comparison with Carbon Dioxide Laser", *Lasers Surg. Med.*, 26:208–214 (2000).

Parrish et al., "Exploring Mechanisms of Specificity in Laser–Tissue Interactions", *Lasers Surg. Med.*, 3:175 (Abstract No. 260) (1983).

Parrish et al., "Spatial Confinement of Thermal Effects of Pulsed Laser Irradiation of Tissue",*Lasers Surg. Med.*, 3:157 (Abstract No. 195) (1973).

Paul et al., "The Effect of Temperature and Other Factors on Selective Microvascular Damage Caused by Pulsed Dye Laser", *J. Invest. Dermatol.*, 81(4):333–336 (1983).

Pfefer et al., "Mechanisms of Laser–Induced Thermal Coagulation of Whole Blood in vitro", *SPIE*, 3590:20–31 (1999).

Philipp et al., "Treatment of Congenital Vascular Disorders: Classification, Step Programme and Therapeutical Procedures", *SPIE*, 2086:228–238 (1993).

Pickering et al., "585 nm for the Laser Treatment of Port Wine Stains: A Possible Mechanism",*Lasers Surg. Med.*, 11:616–618 (1991).

Plewig et al., "A new apparatus for the delivery of high intensity UVA and UVA + UVB irradiation, and some dermatological applications", *Br. J. Dermatol.*, 98:15–24 (1978).

Polla et al., "Tunable Pulsed Dye Laser for the Treatment of Benign Cutaneous Vascular Ectasia", *Dermatologica*, 174:11–17 (1987).

Pottier et al., "Assessment of Non–Coherent Light Sources for Photodynamic Therapy",*SPIE*, 2371:364–368 (1995).

Pratesi, R., "Potential Use of Incoherent and Coherent Light–Emitting–Diodes (LEDs) in Photomedicine", in *Photomedicine, Laser Photobiol. Photomed.*, 22:293–308 (1983).

Ramrus et al., "A Compact One–Half MV Rep–Rate Pulser", *20$^{th}$ IEEE Power Modulator Symposium*, pp. 68–71 (1992).

Ramrus et al., "Design and Performance of a One–Half MV Rep–Rate Pulser", *Proc. Of the 8$^{th}$ IEEE International Pulsed Power Conference*, pp. 982–985 (1991).

Ranganathan et al., "Promises for Ultrasonic Waves on Activity of Silica Gel and Some Supported Catalystes", *Ind. Eng. Chem. Prod. Res. Develop.*, 12:155–158 (1973).

Rassing et al., "Measurement of Ultrasonic Absorption in a Gel by Light Diffraction and Resonator Methods", *J. Mol. Liq.*, 26:97–108 (1983).

Rastegar et al., "Technique for Measurement of One–Dimensional Instantaneous Ablation Velocity", *Lasers Surg. Med.*, 8:533–535 (1988).

Raulin et al., "Treatment of a Nonresponding Port–Wine Stain With a New Pulsed Light Source (PhotoDerm® VL)", *Lasers Surg. Med.*, 21:203–208 (1997).

Raulin et al., "Treatment of Adult Port–Wine Stains Using Intense Pulsed Light Therapy (PhotoDerm VL): Brief Initial Clinical Report", *Dermatol. Surg.*, 23:594–601 (1997).

Raulin et al., "Treatment of benign venous malformations with an intense pulsed light source (PhotoDerm VL)", *Eur. J. Dermatol.*, 7:279–282 (1997).

Raulin et al., "Treatment of Essential Telangiectasias with an Intense Pulsed Light Source (PhotoDerm VL)", *Dermatol. Surg.*, 23:941–946 (1997).

Raulin et al., "Treatment of Port–wine Stains With a Noncoherent Pulsed Light Source", *Arch. Dermatol.*, 135:679–683 (1999).

Reyes et al., "Treatment of port–wine stains during childhood with the flashlamp–pumped pulsed dye laser", *J. Am. Acad. Dermatol.*, 23:1142–1148 (1990).

Ross et al., "Effects of $CO_2$ Laser Pulse Duration in Ablation and Residual Thermal Damage: Implications for Skin Resurfacing", *Lasers Surg. Med.*, 19:123–129 (1996).

Rowe, P.M., "Photodynamic therapy begins to shine",*Lancet*, 351:1496 (1998).

Sadick et al., "Photorejuvenation with Intense Pulsed Light: Results of a Multi–Center Study",*J. Drugs Dermatol.*, 3(1):41–49 (2004).

Sadick, N.S., "A Structural Approach to Nonablative Rejuvenation",*Cosmetic Dermatol.*, 15(12):39–43 (2002).

Sadick, N.S., "Update on Non–Ablative Light Therapy for Rejuvenation: A Review",*Lasers Surg. Med.*, 32:120–128 (2003).

Schamiloglu et al., "Modern Pulsed Power: Charlie Martin and Beyond", *Proceedings of the IEEE*, 92(7):1014–1020 (2004).

Schroeter et al., "An Intense Light Source: The Photoderm VL–Flashlamp as a New Treatment Possibility for Vascular Skin Lesions",*Dermatol. Surg.*, 24:743–748 (1998).

Schroeter et al., "Clinical significance of an intense, pulsed light source on leg telangiectasias of up to 1mm diameter", *Eur. J. Dermatol.*, 7:38–42 (1997).

Schroeter et al., "Photoderm VL treatment of leg telangiectasia",*JEADV*, 5(Suppl. 1):S49 (Abstract No. W76) (1995).

Schwimer et al., "The Effect of Ultrasound Coupling Gels on Sperm Motility in Vitro",*Fertil. Steril.*, 42:946–947 (1984).

Sheean et al., "Arrest of Embryo Development by Ultrasound Coupling Gels",*Fertil. Steril.*, 45:568–571 (1986).

Smith et al., "532–Nanometer Green Laser Beam Treatment of Superficial Varicosities of the Lower Extremities", *Lasers Surg. Med.*, 8:130–134 (1988).

Steiger et al., "Comparison of Different Pulsed and Q–switched Solid–state Laser Systems for Endoscopic Laser Induced Shock Wave Lithotripsy: Performance and Laser/Stone Interactions", *SPIE*, 2300:94–101 (1990).

Strickland et al., "A 5kV, 250 kA Rep–Rated Pulser Using Parallel Ignitrons", *7th IEEE Int'l Pulsed Conf.*, pp. 729–731 (1989).

Sunde et al., "Traumatic Tattoo Removal: Comparison of Four Treatment Methods in an Animal Model with Correlation to Clinical Experience", *Lasers Surg. Med.*, 10:158–164 (1990).

Svaasand et al., "Light and Drug Distribution with Topically Administered Photosensitizers", *Lasers Surg. Med.*, 11:261–265 (1996).

Szeimies et al., "A Possible New Incoherent Lamp for Photodynamic Treatment of Superficial Skin Lesions", *Acta Derm. Venereol (Stockh).*, 74:117–119 (1994).

Tan et al., "Action Spectrum of Vascular Specific Injury Using Pulsed Irradiation", *J. Invest. Dermatol.*, 92(6):868–871 (1989).

Tan et al., "EMLA for Laser Treatment of Portwine Stains in Children", *Lasers Surg. Med.*, 12:543–548 (1992).

Tan et al., "Histologic Responses of Port–wine Stains Treated by Argon, Carbon Dioxide, and Tunable Dye Lasers", *Arch. Dermatol.*, 122:1016–1022 (1986).

Tan et al., "Pulsed Dye Laser Treatment of Recalcitrant Verrucae: A Preliminary Report", *Lasers Surg. Med.*, 13:127–137 (1993).

Tan et al., "Treatment of Children with Port–Wine Stains Using the Flashlamp–Pulsed Tunable Dye Laser", *N. Engl. J. Med.*, 320(7):416–421 (1989).

Taub, A.F., "Photodynamic Therapy: Other Uses", *Dermtol. Clin.*, 25:101–109 (2007).

Taylor et al., "Q–Switched Ruby Laser (QSRL) Irradiation of Benign Pigmented Lesions: Dermal vs. Epidermal", *Lasers Surg. Med.*, 3:65 (Abstract No. 262) (1991).

Templeton et al., "Comparison of infrared coagulation and rubber band ligation for first and second degree haemorroids: a randomized prospective clinical trial", *Br. Med. J.*, 286:1387–1389 (1983).

Troccoli et al., "Multiple–Pulse Photocoagulation of Blood Vessels With A 585 Nm Tunable Laser", *Lasers Surg. Med.*, 4:3 (Abstract No. 2) (1992).

van Gemert et al., "Can Physical Modeling Lead to an Optimal Laser Treatment Strategy for Port–Wine Stains", in *Laser Applications in Medicine and Biology*, Chapter 5, pp. 199–247, Plenum Press, New York (1991).

van Germert et al., "Instantaneous Ablation Behavior of In–Vitro Rods During Laser Irradiation", *Lasers Surg. Med.*, 5:136 (Abstract No. 4) (1985).

van Germert et al., "Is There an Optimal Laser Treatment for Port Wine Stains?", *Lasers Surg. Med.*, 6:76–83 (1986).

van Germert et al., "Wavelengths for Laser Treatment of Port Wine Stains and Telangiectasia", *Lasers Surg. Med.*, 16:147–155 (1995).

"Varicose Vein Device Producer comes to U.S. Market", *Clinica*, 687:9 (Jan. 8, 1996).

Venning et al., "Tattoo removal using infra–red coagulation: a dose comparison", *Br. J. Dermatol.*, 117:99–105 (1987).

Wagner et al., "Percutalgine–Gel et Ultrasonotherapie en Pathologie du Sport", *La Revue de Medecine*, 32:1681–1683 (1982) (in French, with English Abstract Only).

Waldorf et al., "Skin Resurfacing of Fine to Deep Rhytides Using a Char–Free Carbon Dioxide Laser in 47 Patients", *Dermatol. Surg.*, 21:940–946 (1995).

Walsh et al., "Er:YAG Laser Ablation of Tissue: Measurement of Ablation Rates", *Lasers Surg. Med.*, 9:327–337 (1989).

Walsh et al., "Pulsed $CO_2$ Laser Tissue Ablation: Effect of Tissue Type and Pulse Duration On Thermal Damage", *Lasers Surg. Med.*, 8:108–118 (1988).

Walsh, J.T., "Er:YAG Laser Ablation of Tissue: Effect of Pulse Duration and Tissue Type on Thermal Damage", *Lasers Surg. Med.*, 9:314–326 (1989).

Walsh, J.T., "Pulsed Laser Ablation of Tissue: Analysis of the Removal Process and Tissue Healing", *Unpublished Ph.D. dissertation Massachusetts Institute of Technology, on file with Institute Archives and Hayden Library, Massachusetts Institute of Technology*, pp. 1–312 (1988).

Weiss et al., "Rejuvenation of Photoaged Skin: 5 Years Results with Intense Pulsed Light of the Face, Neck, and Chest", *Dermatol. Surg.*, 28:1115–1119 (2002).

Welch et al., "Practical Models for Light Distribution in Laser–Irradiated Tissue", *Lasers Surg. Med.*, 6:488–493 (1987).

Werner et al., "Die Hamangiombehandlung mit dem Neodym: Yttrium–Aluminium–Granat Laser (Nd:YAG–Laser)", *Laryngo–Rhino–Otol.*, 71:388–395 (1992), (in German, with English Abstract Only).

West, T., "How Laser Surgery Can Help Your Rosacea Patients", *Skin & Aging*, pp. 43–46 (1998).

Wilder, D., "Pulsed 1064–nm Nd:YAG Laser Therapy for Noninvasive Treatment of a Massive Hemangioma: Case Report", *J. Clin. Laser Med. Surg.*, 17(6):245–247 (1999).

Wilson et al., "The physics of photodynamic therapy", *Phys. Med. Biol.*, 31(4):327–360 (1986).

R. Rox Anderson et al., Microvasculature Can be Selectively Damaged Using Dye Lasers, Journal of Lasers in Surgery and Medicine, 1981.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–15 are cancelled.

New claims 16–33 are added and determined to be patentable.

*16. An apparatus for destroying blood vessels contained at a selected depth and in a selected area of the dermis, the apparatus comprising:*
  *a diode laser configured to emit at least one pulse of light to the skin surface above the selected area having a wavelength of about 800 nm, with each pulse delivering a fluence between about 5 Joules per square centimeter and 50 Joules per square centimeter, and each pulse having a pulse duration of between about 0.2 and 20 milliseconds; and*
  *a light guide having an area of between about 0.1 square centimeter to 10 square centimeters and configured to direct light to impinge upon an area of the skin and;*
  *wherein the diode laser and the light guide are configured to be positioned relative to the selected area of the dermis such that light from the diode laser can impinge upon the selected area of the dermis.*

*17. The apparatus of claim 16 wherein the diode laser is operated to deliver a single pulse.*

*18. The apparatus of claim 16 wherein the diode laser is a continuous wave laser.*

*19. The apparatus of claim 18 comprising an electrical gate configured to control the duration of the at least one pulse of light.*

*20. The apparatus of claim 18 comprising an optical gate configured to control the duration of the at least one pulse of light.*

*21. The apparatus of claim 16 wherein the diode laser is a AlGaAs semiconductor diode laser.*

*22. An apparatus for destroying blood vessels contained at a selected depth and in a selected area of the dermis, the apparatus comprising:*
  *a diode laser configured to emit at least one pulse of light to the skin surface above the selected area having a wavelength of about 800 nm, with each pulse delivering a fluence between about 5 joules per square centimeter and 50 joules per square centimeter, and each pulse having a pulse duration of between about 0.2 and 20 milliseconds; and*
  *a concentrator having an area of about between 0.4 and 1.5 square centimeters and configured to direct the diode laser light to a plurality of blood vessels,*
  *wherein the diode laser and the concentrator are configured to be positioned relative to the selected area of the dermis such that light from the diode laser will impinge upon the selected area of the dermis.*

*23. The apparatus of claim 22 wherein the diode laser is a continuous wave laser, and comprising a shutter configured to control the duration of the at least one pulse of light.*

*24. A method for destroying blood vessels contained at a selected depth and in a selected area of the dermis, the method comprising:*
  *positioning a diode laser so that light from the diode laser will impinge upon the selected area of the dermis, wherein the selected area of the dermis is at least 1 square centimeter; and*
  *operating the diode laser to deliver at least one light pulse to the skin surface of the selected area having a wavelength of about 810 nm, with each pulse delivering a fluence at a skin surface above the selected area of the dermis between about 5 joules per square centimeter and 50 joules per square centimeter, and each pulse having a pulse duration of between about 0.2 millisecond and 20 milliseconds.*

*25. The method of claim 24 wherein diode laser is operated to deliver a single pulse to the area.*

*26. The method of claim 24 comprising controlling the fluence delivered by the diode laser to the area to control the depth at which a blood vessel is destroyed within the dermis.*

*27. The method of claim 24 comprising controlling the pulse duration depending on the size of the blood vessel to be destroyed.*

*28. The method of claim 24 wherein the blood vessels are leg veins and the diode laser is positioned so that light will impinge a portion of the leg vein which is to be treated and destroyed.*

*29. The method of claim 24 wherein the blood vessels are telangiectasias and the diode laser is positioned so that light will impinge a portion of the telangiectasias which is to be treated and destroyed.*

*30. The method of claim 24 wherein the blood vessels are port wine stains and the diode laser is positioned so that light will impinge a portion of the port wine stains which are to be treated and destroyed.*

*31. The method of claim 24 wherein the blood vessels are disposed up to about 1 mm below the skin surface and the diode laser is positioned so that light will impinge the plurality of blood vessels which are to be treated and destroyed.*

*32. The method of claim 24 wherein the blood vessels underline psoriatic plaque and the diode laser is positioned so that light will impinge a portion of the psoriatic plaque which is to be treated and destroyed.*

*33. The apparatus of claim 16 wherein the light guide has an area of about 1 square centimeter.*

\* \* \* \* \*

(12) EX PARTE REEXAMINATION CERTIFICATE (7507th)
United States Patent
Grove et al.

(10) Number: US 5,707,403 C2
(45) Certificate Issued: May 11, 2010

(54) METHOD FOR THE LASER TREATMENT OF SUBSURFACE BLOOD VESSELS

(75) Inventors: Robert E. Grove, Pleasanton, CA (US); James Z. Holtz, Livermore, CA (US)

(73) Assignee: Bank Hapoalim B.M., Tel Aviv (IL)

Reexamination Request:
No. 90/010,444, Apr. 15, 2009

Reexamination Certificate for:
Patent No.: 5,707,403
Issued: Jan. 13, 1998
Appl. No.: 08/636,286
Filed: Apr. 23, 1996

Reexamination Certificate C1 5,707,403 issued Apr. 7, 2009

Related U.S. Application Data

(63) Continuation-in-part of application No. 08/022,978, filed on Feb. 24, 1993, now Pat. No. 5,527,350.

(51) Int. Cl.
*A61N 5/06* (2006.01)

(52) U.S. Cl. .................................. 607/89; 606/3; 606/9
(58) Field of Classification Search .................. None
See application file for complete search history.

(56) References Cited

U.S. PATENT DOCUMENTS

| | | | |
|---|---|---|---|
| 1,106,699 A | 8/1914 | Carroll | 600/200 |
| 1,651,385 A | 12/1927 | Goodrich | 392/409 |
| 2,699,771 A | 1/1955 | Ruttger-Pelli | 601/15 |
| 2,716,698 A | 8/1955 | Brukner | 240/1 |
| 2,888,917 A | 6/1959 | Fozard | 606/43 |
| 2,954,771 A | 10/1960 | Boyan | 128/396 |
| 3,126,295 A | 3/1964 | Young | 428/337 |
| 3,289,669 A | 12/1966 | Dwyer et al. | 600/565 |
| 3,307,553 A | 3/1967 | Liebner | 607/1 |
| 3,327,712 A | 6/1967 | Kaufman et al. | 128/398 |
| 3,538,919 A | 11/1970 | Meyer | 606/36 |
| 3,559,531 A | 2/1971 | Leibfritz et al. | 91/26 |
| 3,599,934 A | 8/1971 | Reed | 251/363 |
| 3,601,616 A | 8/1971 | Katsumata | 250/223 |
| 3,658,068 A | 4/1972 | McNall | 128/395 |

(Continued)

FOREIGN PATENT DOCUMENTS

| | | |
|---|---|---|
| AT | 355200 | 3/2006 |
| AU | 1851583 | 3/1984 |
| AU | 0691713 | 5/1988 |
| AU | 2940397 | 12/1997 |
| BE | 894290 | 3/1983 |
| CA | 1122156 | 4/1982 |
| CA | 1197563 | 12/1985 |
| CA | 1260116 | 9/1989 |
| CA | 2093055 | 10/1993 |
| CA | 2131750 | 1/1996 |

(Continued)

OTHER PUBLICATIONS

Achauer et al., "Argon Laser Treatment of Telangiectasia of the Face and Neck: 5 Years' Experience", *Lasers Surg. Med.*, 7:495–498 (1987).

Alora et al., "Recent Developments in Cutaneous Lasers", *Lasers Surg. Med.*, 26:108–118 (2000).

(Continued)

*Primary Examiner*—Beverly M. Flanagan

(57) ABSTRACT

The invention provides a method for selectively destroying blood vessels contained at a selected depth and in a selective area of a patients dermis by positioning a laser so that light from the laser will impinge on the selected area of the dermis and operating the laser to deliver pulse light to the area, which light has a wavelength between 700 nm and 1100 nm, with each pulse delivering a fluence at the surface above the area being treated of between 5 joules per square centimeter and 100 joules per square centimeter, and each pulse having a pulse duration of between 0.2 milliseconds and 100 milliseconds.

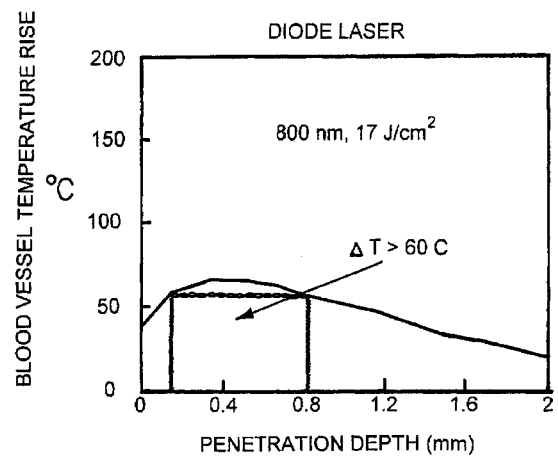

U.S. PATENT DOCUMENTS

| | | | |
|---|---|---|---|
| 3,680,000 A | 7/1972 | Chester et al. | 372/99 |
| 3,693,623 A | 9/1972 | Harte et al. | 128/303.1 |
| 3,710,798 A | 1/1973 | Bredemeier | 606/11 |
| 3,804,732 A | 4/1974 | Goodkin | 204/58 |
| 3,806,829 A | 4/1974 | Duston et al. | 372/38.01 |
| 3,818,914 A | 6/1974 | Bender | 607/90 |
| 3,821,510 A | 6/1974 | Muncheryan | 219/121 |
| 3,834,391 A | 9/1974 | Block | 128/303.1 |
| 3,884,236 A | 5/1975 | Krasnov | 606/3 |
| 3,916,143 A | 10/1975 | Farrell | 219/121.69 |
| 3,930,504 A | 1/1976 | de Laforcade | 128/303.1 |
| 3,967,627 A | 7/1976 | Brown | 128/400 |
| 3,999,552 A | 12/1976 | Huggins | 128/303.13 |
| 4,022,534 A | 5/1977 | Kishner | 356/446 |
| 4,058,752 A | 11/1977 | Woods et al. | 315/360 |
| 4,112,335 A | 9/1978 | Gonser | 315/241 R |
| 4,122,853 A | 10/1978 | Smith | 606/4 |
| 4,174,714 A | 11/1979 | Mehl | 128/303.13 |
| 4,213,462 A | 7/1980 | Sato | 128/634 |
| 4,229,658 A | 10/1980 | Gonser | 250/504 H |
| 4,232,678 A | 11/1980 | Skovajsa | |
| 4,233,493 A | 11/1980 | Nath | 219/354 |
| 4,241,382 A | 12/1980 | Daniel | 362/581 |
| 4,246,902 A | 1/1981 | Martinez | 604/22 |
| 4,266,548 A | 5/1981 | Davi | 606/14 |
| 4,283,661 A | 8/1981 | Doty | 315/360 |
| 4,298,005 A | 11/1981 | Mutzhas | 128/396 |
| 4,316,467 A | 2/1982 | Muckerheide | 606/9 |
| 4,321,930 A | 3/1982 | Jobsis et al. | 128/633 |
| 4,336,809 A | 6/1982 | Clark | 128/665 |
| 4,366,570 A | 12/1982 | Bees | 372/70 |
| 4,380,240 A | 4/1983 | Jobsis et al. | 128/633 |
| 4,381,007 A | 4/1983 | Doss | 128/303.1 |
| 4,387,952 A | 6/1983 | Slusher | 359/220.1 |
| 4,388,924 A | 6/1983 | Weissman et al. | 128/303.1 |
| 4,408,602 A | 10/1983 | Nakajima | 606/10 |
| 4,436,097 A | 3/1984 | Cunningham | 600/520 |
| 4,441,485 A | 4/1984 | Reynolds | 600/200 |
| 4,444,190 A | 4/1984 | Mutzhas | 128/396 |
| 4,454,882 A | 6/1984 | Takano | 607/89 |
| 4,469,098 A | 9/1984 | Davi | 606/7 |
| 4,497,018 A | 1/1985 | Rice | 363/96 |
| 4,503,854 A | 3/1985 | Jako | 606/11 |
| 4,506,196 A | 3/1985 | Bees | 315/241 R |
| 4,515,165 A | 5/1985 | Carroll | 600/475 |
| 4,516,195 A | 5/1985 | Gonser | 362/281 |
| 4,520,816 A | 6/1985 | Schachar et al. | 606/4 |
| 4,521,194 A | 6/1985 | Myers et al. | 433/215 |
| 4,539,987 A | 9/1985 | Nath et al. | 128/303.1 |
| 4,554,666 A | 11/1985 | Altman | 372/19 |
| 4,555,179 A | 11/1985 | Langerholc et al. | 356/342 |
| 4,559,942 A | 12/1985 | Eisenberg | 128/303 |
| 4,560,883 A | 12/1985 | Kerschgens | 250/504 |
| 4,564,011 A | 1/1986 | Goldman | 128/303.1 |
| 4,566,453 A | 1/1986 | Kumano et al. | 606/8 |
| 4,587,396 A | 5/1986 | Rubin | 219/121.78 |
| 4,608,978 A | 9/1986 | Rohr | 606/9 |
| 4,608,979 A | 9/1986 | Breidenthal et al. | 128/303.1 |
| 4,611,245 A | 9/1986 | Trias | 358/235 |
| 4,617,926 A | 10/1986 | Sutton | 606/9 |
| 4,619,887 A | 10/1986 | Hooper et al. | 430/313 |
| 4,620,547 A | 11/1986 | Boebel | 600/567 |
| 4,645,980 A | 2/1987 | Yang | 315/159 |
| 4,647,830 A | 3/1987 | Bees | 320/1 |
| 4,653,495 A | 3/1987 | Nanaumi | 128/303.1 |
| 4,657,018 A | 4/1987 | Hakky | 606/46 |
| 4,669,466 A | 6/1987 | L'Esperance | 606/3 |
| 4,672,969 A | 6/1987 | Dew | 128/397 |
| 4,686,986 A | 8/1987 | Fenyo et al. | 607/90 |
| 4,712,537 A | 12/1987 | Pender | 600/200 |
| 4,718,418 A | 1/1988 | L'Esperance, Jr. | 606/5 |
| 4,726,377 A | 2/1988 | Jegers et al. | 128/376 |
| 4,729,375 A | 3/1988 | Jegers et al. | 128/376 |
| 4,733,660 A | 3/1988 | Itzkan | 128/303.1 |
| 4,744,360 A | 5/1988 | Bath | 606/6 |
| 4,750,486 A | 6/1988 | Butler et al. | 606/18 |
| 4,754,381 A | 6/1988 | Downs | 362/297 |
| 4,757,431 A | 7/1988 | Cross et al. | 362/261 |
| 4,768,513 A | 9/1988 | Suzuki | 600/476 |
| 4,773,097 A | 9/1988 | Suzaki et al. | 382/128 |
| 4,775,361 A | 10/1988 | Jacques et al. | 604/20 |
| 4,784,135 A | 11/1988 | Blum et al. | 606/3 |
| 4,792,341 A | 12/1988 | Kozikowski et al. | 8/103 |
| 4,803,694 A | 2/1989 | Lee et al. | 372/98 |
| 4,810,658 A | 3/1989 | Shanks et al. | 436/172 |
| 4,818,230 A | 4/1989 | Myers et al. | 433/215 |
| 4,818,847 A | 4/1989 | Hara et al. | 235/455 |
| 4,829,262 A | 5/1989 | Furumoto | 330/4.3 |
| 4,835,749 A | 5/1989 | Welton | 368/10 |
| 4,839,562 A | 6/1989 | Francis et al. | 315/149 |
| 4,840,798 A | 6/1989 | Skaliotis | 424/488 |
| 4,846,172 A | 7/1989 | Berlin | 606/4 |
| 4,846,192 A | 7/1989 | MacDonald | 600/565 |
| 4,851,738 A | 7/1989 | Yang | 315/159 |
| 4,858,090 A | 8/1989 | Downs | 362/297 |
| 4,860,172 A | 8/1989 | Schlager et al. | 362/553 |
| 4,862,886 A | 9/1989 | Clarke et al. | 606/7 |
| 4,871,559 A | 10/1989 | Dunn et al. | 426/248 |
| 4,874,009 A | 10/1989 | Pickerrell et al. | 137/454.6 |
| 4,874,361 A | 10/1989 | Obagi | 606/3 |
| 4,875,214 A | 10/1989 | Denne | 372/5 |
| 4,883,333 A | 11/1989 | Yanez | 385/33 |
| 4,884,568 A | 12/1989 | Hahn | 128/303.1 |
| 4,894,547 A | 1/1990 | Leffell et al. | 250/461.2 |
| 4,897,771 A | 1/1990 | Parker | 362/298 |
| 4,907,235 A | 3/1990 | Kuizenga | 372/21 |
| 4,909,782 A | 3/1990 | Semm et al. | 606/171 |
| 4,910,942 A | 3/1990 | Dunn | 53/425 |
| 4,913,132 A | 4/1990 | Gabriel | 600/200 |
| 4,917,083 A | 4/1990 | Harrington et al. | 606/15 |
| 4,917,084 A | 4/1990 | Sinofsky | 606/7 |
| 4,917,486 A | 4/1990 | Raven et al. | 351/221 |
| 4,926,861 A | 5/1990 | Fenyo et al. | 607/88 |
| 4,930,504 A | 6/1990 | Diamantopoulos et al. | 128/395 |
| 4,938,221 A | 7/1990 | Tuffel | 128/401 |
| 4,940,922 A | 7/1990 | Schuda et al. | 315/246 |
| 4,941,082 A | 7/1990 | Pailthorp et al. | 700/57 |
| 4,945,914 A | 8/1990 | Allen | 600/426 |
| 4,947,305 A | 8/1990 | Gunter, Jr. | 362/297 |
| 4,947,859 A | 8/1990 | Brewer et al. | 128/715 |
| 4,950,880 A | 8/1990 | Hayner | 250/201.9 |
| 4,955,882 A | 9/1990 | Hakky | 606/14 |
| 4,973,848 A | 11/1990 | Kolobanov et al. | 250/458.1 |
| 4,974,138 A | 11/1990 | Negishi | 362/347 |
| 4,976,709 A | 12/1990 | Sand | 606/5 |
| 4,988,163 A | 1/1991 | Cohen et al. | 385/31 |
| 4,996,046 A | 2/1991 | Warshaw et al. | 424/445 |
| 5,000,752 A | 3/1991 | Hoskin et al. | 606/9 |
| 5,005,180 A | 4/1991 | Edelman et al. | 372/57 |
| 5,008,579 A | 4/1991 | Conley et al. | 310/303 |
| 5,011,793 A | 4/1991 | Obinata | 427/383.1 |
| 5,016,151 A | 5/1991 | Mula | 362/267 |
| 5,020,995 A | 6/1991 | Levy | 433/215 |
| 5,023,886 A | 6/1991 | Hobart et al. | 372/99 |
| 5,025,446 A | 6/1991 | Kuizenga | 372/21 |
| 5,034,235 A | 7/1991 | Dunn et al. | 426/238 |
| 5,039,867 A | 8/1991 | Nishihara et al. | 250/492.3 |
| 5,048,034 A | 9/1991 | Tulip | 372/41 |
| 5,049,147 A | 9/1991 | Danon | 606/10 |
| 5,054,488 A | 10/1991 | Muz | 128/633 |
| 5,057,100 A | 10/1991 | Lombardo | 606/17 |

| Patent No. | Date | Name | Class |
|---|---|---|---|
| 5,057,104 A | 10/1991 | Chess | 606/9 |
| 5,059,192 A | 10/1991 | Zaias | 606/9 |
| 5,063,961 A | 11/1991 | Brunner | 137/454.5 |
| 5,066,291 A | 11/1991 | Stewart | 606/3 |
| 5,066,293 A | 11/1991 | Furumoto | 606/9 |
| 5,071,417 A | 12/1991 | Sinofsky | 606/8 |
| 5,071,422 A | 12/1991 | Watson et al. | 606/128 |
| 5,074,861 A | 12/1991 | Schneider et al. | 606/17 |
| 5,077,099 A | 12/1991 | Kukanskis et al. | 427/437 |
| 5,078,711 A | 1/1992 | Kakami et al. | 606/16 |
| 5,083,093 A | 1/1992 | Adler et al. | 328/65 |
| 5,084,881 A | 1/1992 | Farries et al. | 372/6 |
| 5,089,945 A | 2/1992 | Mula | 362/261 |
| 5,097,471 A | 3/1992 | Negus et al. | 372/18 |
| 5,106,364 A | 4/1992 | Hayafuji et al. | 604/22 |
| 5,109,463 A | 4/1992 | Lee | 385/123 |
| 5,112,328 A | 5/1992 | Taboada et al. | 606/4 |
| 5,113,462 A | 5/1992 | Clancy et al. | 385/53 |
| 5,123,026 A | 6/1992 | Fan et al. | 372/75 |
| 5,125,922 A | 6/1992 | Dwyer et al. | 606/3 |
| 5,126,621 A | 6/1992 | Morton et al. | 313/237 |
| 5,130,997 A | 7/1992 | Ortiz et al. | 372/21 |
| 5,133,035 A | 7/1992 | Hicks | 385/117 |
| 5,137,539 A | 8/1992 | Bowling | 44/626 |
| 5,139,494 A | 8/1992 | Freiberg | 606/3 |
| 5,146,923 A | 9/1992 | Dhawan | 600/476 |
| 5,161,526 A | 11/1992 | Hellwing et al. | 607/89 |
| 5,178,617 A | 1/1993 | Kuizenga et al. | 606/17 |
| 5,194,723 A | 3/1993 | Cates et al. | 250/205 |
| 5,200,604 A | 4/1993 | Rudko et al. | 250/205 |
| 5,201,731 A | 4/1993 | Hakky | 606/15 |
| 5,204,517 A | 4/1993 | Cates et al. | 250/205 |
| 5,206,867 A | 4/1993 | Esterowitz et al. | 372/20 |
| 5,207,670 A | 5/1993 | Sinofsky | 606/8 |
| 5,207,671 A | 5/1993 | Franken et al. | 606/9 |
| 5,217,455 A | 6/1993 | Tan | 606/9 |
| 5,222,952 A | 6/1993 | Loertscher | 606/6 |
| 5,226,107 A | 7/1993 | Stern et al. | 392/416 |
| 5,226,430 A | 7/1993 | Spears et al. | 128/898 |
| 5,226,907 A | 7/1993 | Tankovich | 606/133 |
| 5,242,460 A | 9/1993 | Klein et al. | 606/159 |
| 5,243,615 A | 9/1993 | Ortiz et al. | 372/34 |
| 5,246,435 A | 9/1993 | Bille et al. | 606/6 |
| 5,246,436 A | 9/1993 | Rowe | 606/13 |
| 5,247,935 A | 9/1993 | Cline et al. | 128/653.2 |
| 5,249,190 A | 9/1993 | Kortz et al. | 372/22 |
| 5,257,274 A | 10/1993 | Barrett et al. | 372/20 |
| 5,259,380 A | 11/1993 | Mendes et al. | 607/115 |
| 5,263,038 A | 11/1993 | Lukas et al. | 372/22 |
| 5,263,950 A | 11/1993 | L'Esperance, Jr. | 606/6 |
| 5,265,598 A | 11/1993 | Searfoss et al. | 607/89 |
| 5,269,778 A | 12/1993 | Rink et al. | 606/12 |
| 5,272,518 A | 12/1993 | Vincent | 356/405 |
| 5,272,713 A | 12/1993 | Sobey et al. | 372/69 |
| 5,274,728 A | 12/1993 | Tran | 385/142 |
| 5,280,378 A | 1/1994 | Lombardo | 359/199.1 |
| 5,281,798 A | 1/1994 | Hamm et al. | 250/205 |
| 5,282,797 A | 2/1994 | Chess | 606/9 |
| 5,282,798 A | 2/1994 | Bruse et al. | 606/17 |
| 5,287,380 A | 2/1994 | Hsia | 372/69 |
| 5,289,479 A | 2/1994 | Oka et al. | 372/22 |
| 5,290,273 A | 3/1994 | Tan | 606/9 |
| 5,290,274 A | 3/1994 | Levy et al. | 606/13 |
| 5,293,872 A | 3/1994 | Alfano | 128/664 |
| 5,300,097 A | 4/1994 | Lerner et al. | 607/93 |
| 5,304,167 A | 4/1994 | Freiberg | 606/3 |
| 5,304,169 A | 4/1994 | Sand | 606/5 |
| 5,304,170 A | 4/1994 | Green | 606/9 |
| 5,312,395 A | 5/1994 | Tan et al. | 606/9 |
| 5,312,396 A | 5/1994 | Feld et al. | 606/11 |
| 5,312,399 A | 5/1994 | Hakky et al. | 606/15 |
| 5,320,618 A | 6/1994 | Gustafsson | 606/9 |
| 5,321,715 A | 6/1994 | Trost | 372/69 |
| 5,325,458 A | 6/1994 | Morrow et al. | 385/125 |
| 5,328,488 A | 7/1994 | Daikuzono | 606/16 |
| 5,328,517 A | 7/1994 | Cates et al. | 134/7 |
| 5,330,517 A | 7/1994 | Mordon et al. | 607/89 |
| 5,334,190 A | 8/1994 | Seiler | 606/5 |
| 5,336,216 A | 8/1994 | Dewey | 606/4 |
| 5,336,217 A | 8/1994 | Buys et al. | 606/9 |
| 5,337,741 A | 8/1994 | Diamond | 600/8 |
| 5,342,198 A | 8/1994 | Vassiliadis et al. | 433/215 |
| 5,344,418 A | 9/1994 | Ghaffari | 606/9 |
| 5,344,433 A | 9/1994 | Talmore | 607/88 |
| 5,344,434 A | 9/1994 | Talmore | 607/88 |
| 5,345,457 A | 9/1994 | Zenzie et al. | 372/22 |
| 5,349,590 A | 9/1994 | Amirkhanian et al. | 372/6 |
| 5,360,424 A | 11/1994 | Klopotek | 606/4 |
| 5,363,387 A | 11/1994 | Sinofsky | 372/15 |
| 5,363,854 A | 11/1994 | Martens et al. | 600/477 |
| 5,364,390 A | 11/1994 | Taboada et al. | 608/10 |
| 5,368,031 A | 11/1994 | Cline et al. | 600/411 |
| 5,368,634 A | 11/1994 | Hackett | 95/260 |
| 5,370,651 A | 12/1994 | Summers | 606/159 |
| 5,374,265 A | 12/1994 | Sand | 606/5 |
| 5,375,132 A | 12/1994 | Connors et al. | 372/34 |
| 5,382,013 A | 1/1995 | Walsh | 271/186 |
| 5,383,467 A | 1/1995 | Auer | 128/664 |
| 5,384,796 A | 1/1995 | Jee | 372/22 |
| 5,386,837 A | 2/1995 | Sterzer | 128/898 |
| 5,387,211 A | 2/1995 | Saadatmanesh et al. | 606/10 |
| 5,390,204 A | 2/1995 | Yessik | 372/38 |
| 5,394,307 A | 2/1995 | Matsuura | 362/16 |
| 5,395,362 A | 3/1995 | Sacharoff et al. | 606/17 |
| 5,397,327 A | 3/1995 | Koop et al. | 606/17 |
| 5,400,428 A | 3/1995 | Grace | 385/115 |
| 5,400,791 A | 3/1995 | Schlier et al. | 128/664 |
| 5,401,171 A | 3/1995 | Paghdiwala | 433/215 |
| 5,403,276 A | 4/1995 | Schechter et al. | 604/22 |
| 5,405,368 A | 4/1995 | Eckhouse | 607/88 |
| 5,405,726 A | 4/1995 | Abe et al. | 430/97 |
| 5,406,577 A | 4/1995 | Gagosz | 372/69 |
| 5,409,479 A | 4/1995 | Dew et al. | 606/9 |
| 5,409,483 A | 4/1995 | Campbell et al. | 606/15 |
| 5,411,502 A | 5/1995 | Zair | 606/10 |
| 5,414,600 A | 5/1995 | Strobl et al. | 362/551 |
| 5,422,899 A | 6/1995 | Freiberg et al. | 372/25 |
| 5,423,798 A | 6/1995 | Crow | 606/4 |
| 5,423,803 A | 6/1995 | Tankovich et al. | 606/9 |
| 5,425,728 A | 6/1995 | Tankovich | 606/9 |
| 5,431,646 A | 7/1995 | Vassiliadis et al. | 606/6 |
| 5,435,724 A | 7/1995 | Goodman et al. | 433/215 |
| 5,438,303 A | 8/1995 | Murakami et al. | 332/109 |
| 5,441,531 A | 8/1995 | Zarate et al. | |
| 5,445,146 A | 8/1995 | Bellinger | 607/89 |
| D363,349 S | 10/1995 | Dittert | D24/158 |
| 5,454,807 A | 10/1995 | Lennox et al. | 606/15 |
| 5,456,689 A | 10/1995 | Kresch et al. | 606/180 |
| 5,458,112 A | 10/1995 | Weaver | 600/566 |
| 5,474,528 A | 12/1995 | Meserol | 604/20 |
| 5,474,549 A | 12/1995 | Ortiz et al. | 606/9 |
| 5,476,461 A | 12/1995 | Cho et al. | 606/15 |
| 5,484,432 A | 1/1996 | Sand | 606/5 |
| 5,489,279 A | 2/1996 | Meserol | 604/290 |
| 5,490,860 A | 2/1996 | Middle et al. | 606/171 |
| 5,498,258 A | 3/1996 | Hakky et al. | 606/15 |
| 5,498,935 A | 3/1996 | McMahan et al. | 315/241 P |
| 5,501,680 A | 3/1996 | Kurtz et al. | 606/9 |
| 5,511,563 A | 4/1996 | Diamond | 128/898 |
| 5,520,679 A | 5/1996 | Lin | 606/5 |
| 5,522,814 A | 6/1996 | Bernaz | 606/36 |
| 5,527,332 A | 6/1996 | Clement | 606/171 |

| Patent No. | Date | Inventor | Class |
|---|---|---|---|
| 5,527,350 A | 6/1996 | Grove et al. | 607/89 |
| 5,529,954 A | 6/1996 | Iijima et al. | 438/653 |
| 5,531,739 A | 7/1996 | Trelles | 606/2.5 |
| 5,531,740 A | 7/1996 | Black | 606/9 |
| 5,540,676 A | 7/1996 | Freiberg | 606/3 |
| 5,544,651 A | 8/1996 | Wilk | 600/310 |
| 5,546,214 A | 8/1996 | Black et al. | 359/203 |
| 5,558,666 A | 9/1996 | Dewey et al. | 606/9 |
| 5,558,667 A | 9/1996 | Yarborough et al. | 606/9 |
| 5,560,699 A | 10/1996 | Davenport et al. | 362/558 |
| 5,569,284 A | 10/1996 | Young et al. | 606/180 |
| 5,572,311 A | 11/1996 | Abe | 399/127 |
| 5,578,029 A | 11/1996 | Trelles et al. | 606/25 |
| 5,586,981 A | 12/1996 | Hu | 606/9 |
| 5,588,428 A | 12/1996 | Smith et al. | 600/425 |
| 5,591,157 A | 1/1997 | Hennings et al. | 606/3 |
| 5,595,568 A | 1/1997 | Anderson et al. | 606/9 |
| 5,599,342 A | 2/1997 | Hsia et al. | 606/9 |
| 5,606,798 A | 3/1997 | Kelman | 30/41.5 |
| 5,608,520 A | 3/1997 | Fleming | 356/318 |
| 5,611,795 A | 3/1997 | Slatkine et al. | 606/9 |
| 5,618,284 A | 4/1997 | Sand | 606/5 |
| 5,618,285 A | 4/1997 | Zair | 606/10 |
| 5,620,478 A | 4/1997 | Eckhouse | 607/88 |
| 5,621,745 A | 4/1997 | Yessik et al. | 372/26 |
| 5,626,631 A | 5/1997 | Eckhouse | 607/88 |
| 5,628,744 A | 5/1997 | Coleman et al. | 606/12 |
| 5,630,811 A | 5/1997 | Miller | 606/9 |
| 5,642,370 A | 6/1997 | Mitchell et al. | 372/25 |
| 5,643,334 A | 7/1997 | Eckhouse et al. | 697/88 |
| 5,644,585 A | 7/1997 | Mitchell et al. | 372/25 |
| 5,649,972 A | 7/1997 | Hochstein | 607/100 |
| 5,655,547 A | 8/1997 | Karni | 128/898 |
| 5,658,323 A | 8/1997 | Miller | 607/89 |
| 5,660,836 A | 8/1997 | Knowlton | 424/400 |
| 5,662,644 A | 9/1997 | Swor | 606/9 |
| 5,683,380 A | 11/1997 | Eckhouse et al. | 606/9 |
| 5,707,413 A | 1/1998 | Inao | 65/78 |
| 5,710,626 A | 1/1998 | O'rourke et al. | 356/301 |
| 5,720,772 A | 2/1998 | Eckhouse | 607/88 |
| 5,722,970 A | 3/1998 | Colvard et al. | 606/3 |
| 5,725,565 A | 3/1998 | Smith | 607/88 |
| 5,733,277 A | 3/1998 | Pallarito | 606/7 |
| 5,733,297 A | 3/1998 | Wang | 606/167 |
| 5,735,844 A | 4/1998 | Anderson et al. | 606/9 |
| 5,738,677 A | 4/1998 | Colvard et al. | 606/4 |
| 5,741,245 A | 4/1998 | Cozean et al. | 606/5 |
| 5,743,902 A | 4/1998 | Trost | 606/18 |
| 5,748,655 A | 5/1998 | Yessik et al. | 372/22 |
| 5,749,868 A | 5/1998 | Furumoto | 606/9 |
| 5,754,573 A | 5/1998 | Yarborough et al. | 372/32 |
| 5,755,751 A | 5/1998 | Eckhouse | 607/88 |
| 5,755,753 A | 5/1998 | Knowlton | 607/98 |
| 5,769,844 A | 6/1998 | Ghaffari | 606/16 |
| 5,776,175 A | 7/1998 | Eckhouse et al. | 607/100 |
| 5,783,798 A | 7/1998 | Abraham | 219/121.73 |
| 5,786,929 A | 7/1998 | Nabors | 359/330 |
| 5,810,801 A | 9/1998 | Anderson et al. | 606/9 |
| 5,814,040 A | 9/1998 | Nelson et al. | 606/9 |
| 5,817,089 A | 10/1998 | Tankovich et al. | 606/9 |
| 5,817,090 A | 10/1998 | Abergel et al. | 606/9 |
| 5,828,803 A | 10/1998 | Eckhouse | 385/88 |
| 5,830,208 A | 11/1998 | Muller | 606/9 |
| 5,833,612 A | 11/1998 | Eckhouse et al. | 600/476 |
| 5,833,683 A | 11/1998 | Fuller et al. | 606/17 |
| 5,836,939 A | 11/1998 | Negus et al. | 606/11 |
| 5,836,999 A | 11/1998 | Eckhouse et al. | 607/88 |
| 5,843,143 A | 12/1998 | Whitehurst | 607/88 |
| 5,849,029 A | 12/1998 | Eckhouse et al. | 607/104 |
| 5,853,407 A | 12/1998 | Miller | 606/9 |
| 5,855,595 A | 1/1999 | Fujishima et al. | 607/90 |
| 5,860,967 A | 1/1999 | Zavislan et al. | 606/9 |
| 5,860,968 A | 1/1999 | Wojcik et al. | 606/10 |
| 5,865,830 A | 2/1999 | Parel et al. | 606/5 |
| 5,871,479 A | 2/1999 | Furumoto et al. | 606/9 |
| 5,879,346 A | 3/1999 | Waldman et al. | 606/9 |
| 5,879,376 A | 3/1999 | Miller | 607/89 |
| 5,885,273 A | 3/1999 | Eckhouse et al. | 606/9 |
| 5,885,274 A | 3/1999 | Fullmer | 606/9 |
| 5,900,211 A | 5/1999 | Dunn et al. | 422/24 |
| 5,906,609 A | 5/1999 | Assa et al. | 606/9 |
| 5,907,574 A | 5/1999 | Karni | 372/95 |
| 5,911,718 A | 6/1999 | Yarborough et al. | 606/9 |
| 5,912,457 A | 6/1999 | Mcquaid | 240/227.17 |
| 5,938,657 A | 8/1999 | Assa et al. | 606/9 |
| 5,957,915 A | 9/1999 | Trost | 606/13 |
| 5,970,983 A | 10/1999 | Karni et al. | 128/898 |
| 5,983,900 A | 11/1999 | Clement et al. | 128/898 |
| 6,024,751 A | 2/2000 | Lovato et al. | 606/170 |
| RE36,634 E | 3/2000 | Ghaffari | 606/9 |
| 6,045,548 A | 4/2000 | Furumoto et al. | 606/9 |
| 6,077,294 A | 6/2000 | Cho et al. | 607/89 |
| 6,090,101 A | 7/2000 | Quon et al. | 606/9 |
| 6,096,031 A | 8/2000 | Mitchell et al. | 606/15 |
| 6,130,900 A | 10/2000 | Black et al. | 372/25 |
| 6,139,712 A | 10/2000 | Patton et al. | 205/143 |
| 6,165,170 A | 12/2000 | Wynne et al. | 606/9 |
| 6,171,302 B1 | 1/2001 | Talpalriu et al. | 606/9 |
| 6,171,332 B1 | 1/2001 | Whitehurst | 607/89 |
| 6,190,376 B1 | 2/2001 | Asah et al. | 606/9 |
| 6,193,711 B1 | 2/2001 | Connors et al. | 606/12 |
| 6,235,016 B1 | 5/2001 | Stewart | 606/9 |
| 6,280,438 B1 | 8/2001 | Eckhouse et al. | 606/9 |
| 6,282,223 B1 | 8/2001 | Angeley | 372/92 |
| 6,289,236 B1 | 9/2001 | Koenig et al. | 600/477 |
| 6,379,376 B1 | 4/2002 | Lubart | 607/88 |
| 6,387,089 B1 | 5/2002 | Kreindel et al. | 606/9 |
| 6,451,010 B1 | 9/2002 | Angeley | 606/17 |
| 6,475,138 B1 | 11/2002 | Schechter et al. | 600/108 |
| 6,505,059 B1 | 1/2003 | Kollias et al. | 600/316 |
| 6,514,243 B1 | 2/2003 | Eckhouse et al. | 606/9 |
| 6,522,911 B1 | 2/2003 | Toida et al. | 600/473 |
| 6,544,585 B1 | 4/2003 | Hongo et al. | 216/18 |
| 6,702,838 B1 | 3/2004 | Andersen et al. | 607/89 |
| 6,766,187 B1 | 7/2004 | Black et al. | 600/473 |

FOREIGN PATENT DOCUMENTS

| Country | Number | Date |
|---|---|---|
| CA | 2168624 | 8/1996 |
| CH | 416861 | 7/1966 |
| DE | 565331 | 11/1932 |
| DE | 2308554 | 8/1974 |
| DE | 2740179 | 3/1978 |
| DE | 2717421 | 11/1978 |
| DE | 27 17 421 A1 | 11/1978 |
| DE | 2740969 | 3/1979 |
| DE | 7901050 | 5/1979 |
| DE | 2901534 | 7/1979 |
| DE | 2846471 | 5/1980 |
| DE | 2948580 | 6/1980 |
| DE | 3220218 | 3/1983 |
| DE | 3330293 | 3/1985 |
| DE | 3804732 | 8/1989 |
| DE | 3906860 | 9/1989 |
| DE | 4031320 A | 4/1992 |
| DE | 9304869 | 9/1993 |
| DE | 9321497 | 8/1998 |
| EP | 0003312 | 8/1979 |
| EP | 0052765 | 6/1982 |
| EP | 0075860 | 4/1983 |
| EP | 0172490 | 2/1986 |
| EP | 0185810 | 7/1986 |
| EP | 0198257 | 10/1986 |

| | | |
|---|---|---|
| EP | 0240990 | 10/1987 |
| EP | 0310285 | 4/1989 |
| EP | 0324490 | 7/1989 |
| EP | 0335714 | 10/1989 |
| EP | 0429297 | 5/1991 |
| EP | 0480995 | 4/1992 |
| EP | 0527050 | 2/1993 |
| EP | 0565331 A2 | 10/1993 |
| EP | 0575274 | 12/1993 |
| EP | 0626229 | 11/1994 |
| EP | 0724292 | 7/1996 |
| EP | 0724894 | 8/1996 |
| EP | 0736308 | 10/1996 |
| EP | 0753285 A1 | 1/1997 |
| EP | 0763371 | 3/1997 |
| EP | 0807418 | 11/1997 |
| EP | 0880168 | 11/1998 |
| EP | 0885629 | 12/1998 |
| EP | 1078604 | 2/2001 |
| EP | 1078605 | 2/2001 |
| ES | 8306601 | 9/1983 |
| FI | 822940 | 3/1983 |
| FI | 0931608 | 10/1993 |
| FR | 2193628 | 2/1974 |
| FR | 2342745 | 9/1977 |
| FR | 2364038 | 4/1978 |
| FR | 2389229 | 11/1978 |
| FR | 2571264 | 4/1986 |
| GB | 1116465 | 6/1968 |
| GB | 2012939 | 8/1979 |
| GB | 2105195 | 3/1983 |
| GB | 2218660 | 11/1989 |
| HU | 181836 | 11/1983 |
| HU | 186081 | 5/1985 |
| IL | 101547 | 12/1996 |
| JP | 52109387 | 9/1977 |
| JP | 53105083 | 9/1978 |
| JP | 55117166 | 9/1980 |
| JP | 56109654 | 8/1981 |
| JP | 56124451 | 9/1981 |
| JP | 56137140 | 10/1981 |
| JP | 58086178 | 5/1983 |
| JP | 60006871 | 1/1985 |
| JP | 60132571 | 7/1985 |
| JP | 62114543 | 5/1987 |
| JP | 63277771 | 11/1988 |
| JP | 1034378 | 2/1989 |
| JP | 64012402 | 2/1989 |
| JP | 1240694 | 9/1989 |
| JP | 2154753 | 6/1990 |
| JP | 3016956 | 1/1991 |
| JP | H3-128069 | 5/1991 |
| JP | 3211287 | 9/1991 |
| JP | 3233986 | 10/1991 |
| JP | HE1-4-53569 | 2/1992 |
| JP | 4067860 | 3/1992 |
| JP | 4079966 | 3/1992 |
| JP | 4-90360 | 8/1992 |
| JP | 5001559 | 1/1993 |
| JP | 5029089 | 2/1993 |
| JP | 5111539 | 5/1993 |
| JP | 6063165 | 3/1994 |
| JP | 6198945 | 7/1994 |
| JP | 7008281 | 1/1995 |
| JP | 7275380 | 10/1995 |
| JP | 7308300 | 11/1995 |
| JP | 86266326 | 10/1996 |
| LU | 84349 | 6/1983 |
| SE | 416861 | 2/1981 |
| SE | 452852 | 12/1987 |
| SE | 465 953 B | 11/1991 |
| SE | 515325 | 7/2001 |
| SU | 1347142 | 10/1987 |
| WO | WO 80/02640 | 12/1980 |
| WO | WO 84/03049 | 8/1984 |
| WO | WO 84/04463 | 11/1984 |
| WO | WO 89/00871 | 2/1989 |
| WO | WO 89/11261 | 11/1989 |
| WO | WO 90/12545 | 11/1990 |
| WO | WO 90/14836 | 12/1990 |
| WO | WO 91/000063 | 1/1991 |
| WO | WO 91/12766 | 9/1991 |
| WO | WO 91/13652 | 9/1991 |
| WO | WO 91/15264 | 10/1991 |
| WO | WO 91/015264 | 10/1991 |
| WO | WO 92/019165 | 11/1992 |
| WO | WO 93/008715 | 5/1993 |
| WO | WO 95/15725 | 6/1995 |
| WO | WO 96/021490 | 7/1996 |
| WO | WO 66/33538 | 10/1996 |
| WO | WO 96/32895 | 10/1996 |
| WO | WO 96/41577 | 12/1996 |
| WO | WO 97/37602 | 10/1997 |
| WO | WO 98/52645 | 11/1998 |
| WO | WO 99/25905 | 5/1999 |
| WO | WO 99/055243 | 11/1999 |
| WO | WO 00/32835 | 6/2000 |

OTHER PUBLICATIONS

Alster et al., "Treatment of Port–Wine Stains with the Flashlamp–pumped Pulsed Dye Laser: Extended Clinical Experience in Children and Adults",*Ann. Plast. Surg.,* 32(5):478–484 (1994).

Altshuler et al., "Extended Theory of Selective Photothermolysis",*Lasers Surg. Med.,* 29:416–432 (2001).

Ambrose et al., "Prospective randomized comparison of photocoagulation and rubber band ligation in treatment of haemorrhoids", *Br. Med. J.,* 286:1389–1391 (1983).

Anderson et al., "Mechanisms of Selective Vascular Changes Caused by Dye Lasers",*Lasers Surg. Med.,* 3:211–215 (1983).

Anderson et al., "Microvasculature Can Be Selectively Damaged Using Dye Lasers: A Basic Theory and Experimental Evidence in Human Skin",*Lasers Surg. Med.,* 1:263–276 (1981).

Anderson et al., "Selective Photothermolysis: Precise Microsurgery by Selective Absorption of Pulsed Radiation", *Science,* 220:524–527 (1983).

Anderson, T.F., "Light Sources in Photomedicine", in *Clinical Photomedicine,* Chapter 3, pp. 37–58, Marcel Dekker, Inc., New York (1993).

Angermeier, M.C., "Treatment of facial vascular lesions with intense pulsed light",*J. Cutan. Laser Ther.,* 1:95–100 (1999).

Anvari et al., "Selective cooling of biological tissues: application for thermally mediated therapeutic procedures", *Phys. Med. Biol.,* 40:241–252 (1995).

Apfelberg et al., "Comparison of Argon and Carbon Dioxide Laser for Treatment of Decorative Tattoos Clinical and Pathological Observations", *Lasers Surg. Med.,* 3:183 (Abstract No. 294) (1983).

Apfelberg et al., Dot or Pointillistic Method for Improvement in Results of Hypertrophic Scarringin the Argon Laser Treatment of Portwine Hemangiomas,*Lasers Surg. Med.,* 6:552–558 (1987).

Apfelberg et al., "Investigation of YAG Laser Uses in Plastic Surgery",*Lasers Surg.,* 6:246 (Abstract No. 77) (1986).

Apfelberg et al., "Preliminary Investigation of KTP/532 Laser Light in the Treatment of Hemangiomas and Tattoos", *Lasers Surg. Med.*, 6:38–42 (1986).

Apfelberg et al., "Progress Report on Extended Clinical Use of the Argon Laser for Cutaneous Lesions", *Lasers Surg. Med.*, 1:71–83 (1980).

Apfelberg et al., "Progress Report on Multicenter Study of Laser–Assisted Liposuction", *Aesth. Plast. Surg.*, 18:259–264 (1994).

Apfelberg et al., "Results of Argon and CO2 Laser Exposure of Telangiectasia of the Lower Extremity: A Preliminary Report", *Lasers Surg. Med.*, 3:149 (Abstract No. 165) (1983).

Apfelberg et al., "Study of Three Laser Systems for Treatment of Superficial Varicosities of the Lower Extremity", *Lasers Surg. Med.*, 7:219–223 (1987).

Apfelberg et al., "Superpulse $CO_2$ Laser Treatment of Facial Syringomata", *Lasers Surg. Med.*, 7:533–537 (1987).

Apfelberg et al., "Update on Laser Usage in Treatment of Decorative Tattoos", *Lasers Surg. Med.*, 2:169–177 (1982).

Apfelberg, D.B., "Intralesional Laser Photocoagulation—Steroids as an Adjunct to Surgery for Massive Hemangiomas and Vascular Malformations",*Ann. Plast. Surg.*, 35:144–148 (1995).

Ara et al., "Irradiation of Pigmented Melanoma Cells with High Intensity Pulsed Radiation Generates Acoustic Waves and Kills Cells", *Lasers Surg. Med.*, 10:52–59 (1990).

Ashinoff et al., "Cappillary Hemangiomas and Treatment with the Flash LampPumped Pulsed Dye Laser", *Arch. Dermatol.*, 127:202–205 (1991).

Ashinoff et al., "Flashlamp–pumped pulsed dye laser for port–wine stains in infancy: Earlier versus later treatment", *J. Am. Acad. Dermatol.*, 24:467–472 (1991).

Bell et al., "100 μsec pulsed $CO_2$ laser resurfacing of lower eyelids: Erythema and rhytides reduction", *SPIE*, 2970:360–366 (1997).

Broska et al., "Comparison of the Argon Tunable Dye Laser with the Flashlamp Pulsed Dye Laser in Treatment of Facial Telangiectasia",*J. Dermatol. Surg. Oncol.*, 20:749–753 (1994).

Brugmans et al., "Temperature Response of Biological Materials to Pulsed Non–Ablative $CO_2$ Laser Irradiation", *Lasers Surg. Med.*, 11:587–594 (1991).

Burson et al., "Gel de Transmision de Ultrasonidos: Estudio Comparitivo de Distintas Formulaciones", *Farm Hosp.*, pp. 394–399 (1991) (in Spanish, with English Abstract Only).

Cates, M.C., "A long pulse (5μs) e–beam pumped XeF laser", *SPIE*, 1225:34–43 (1990).

Cates, M.C., "Excimer laser produced plasma studies", *SPIE*, 1279:102–111 (1990).

Chess et al., "Cool Laser Optics Treatment of Large Telangiectasia of the Lower Extremities",*J. Dermatol. Surg. Oncol.*, 19:74–80 (1993).

Chissler et al., "Tanning Beds Are Not Without Drawbacks", *FDA Consumer*, pp. 21–22 (1984).

Cliff et al., "Treatment of mature port wine stains with the PhotoDerm VL",*J. Cutan. Laser Ther.*, 1:101–104 (1999).

Cole–Beuglet et al., "Ultrasound mammography for the Augmented Breast",*Radiology*, 146:737–742 (1983).

Colver et al., "Port Wine Stains", *J. Roy. Soc. Med.*, 80:603 (1987).

Colver et al., "Precise dermal damage with an infrared coagulator", *Br. J. Dermatol.*, 114:603–608 (1986).

Colver et al., "Tattoo removal using infra–red coagulation", *Br. J. Dermatol*, 112:481–485 (1985).

Colver G.B., "The Infrared Coagulator in Dermatology", *Dermatologic Clinics*, 7(1):155–167 (1989).

Daniell et al., "A History of Photodynamic Therapy",*Aust. N. Z. J. Surg.*, 61:340–348 (1991).

Denham et al., "Light Distribution in Laser Irradiated Tissue", *Lasers Surg. Med.*, 5:141 (Abstract No. 21) (1985).

Dzubow et al., "Leg Veins and Stretch Marks", *Am. Soc. Dermatol. Surg.*, 22:321 (1996).

Efthymiopoulos et al., "High–energy Short–pulse Flashlamps: Operating Characteristics", *Applied Optics*, 16:70–75 (1977).

Ell et al., "Laser Lithotripsy of Gallstone by Means of a Pulsed Neodymium YAG Laser—In Vitro and Animal Experments", *Endoscopy*, 18:92–94 (1986).

Englehardt et al., "Spectroscopy During Laser Induced Shock Wave Lithotripsy",*SPIE*, 906:200–204 (1988).

Fitzpatrick et al., "Flashlamp–pumped Pulsed Dye Laser Treatment of Port–Wine Stains", *J. Dermatol. Surg. Oncol.*, 20:743–748 (1994).

Fitzpatrick et al., "Treatment of Leg Veins: A Comparison of Laser Therapy with a Noncoherent, Multiwave Light Source", *Proc. Ann. Meeting IEEE Lasers & Electro–Optics Soc*, pp. 238–239 (1993).

Flock et al., "Er:YAG Laser–Induced Changes in Skin In Vivo And Transdermal Drug Delivery", *SPIE*, 2970:374–379 (1997).

Flock et al., "Thermal Damage of Blood Vessels in Rat Skin–flap Window Chamber Using Indocyanine Green and a Pulsed Alexandrite Laser: A Feasibility Study", *Lasers Med. Sci.*, 8:185–196 (1993).

Foster et al., "The Successful Use of the PhotoDerm VL in the Treatment of a Cavernous Hemangioma in a Dark–Skinned Infant", *Minimally Invasive Surgical Nursing*, 10:102–104 (1996).

Garden et al., "Effect of Dye Laser Pulse Duration on Selective Cutaneous Vascular Injury",*J. Invest. Dermatol.*, 87(5):653–657 (1986).

Garden et al., "The Treatment of Port–wine Stains by the Pulsed Dye Laser: Analysis of Pulse Duration and Long–term Therapy", *Arch. Dermatol.*, 124:889–896 (1988).

Geronemus et al., "The Medical Necessity of Evaluation and Treatment of Port–Wine Stains", *J. Dermatol. Surg. Oncol.*, 17:76–79 (1991).

Gijsbers et al., "CW Laser Ablation Velocities as a Function of Absorption in an Experimental One–Dimensional Tissue Model", *Lasers Surg. Med.*, 11:287–296 (1991).

Gijsbers et al., "Effect of Force on Ablation Depth for a XeCl Excimer Laser Beam Delivered by an Optical Fiber in Contact with Arterial Tissue Under Saline", *Lasers Surg. Med.*, 12:576–584 (1992).

Gilbert, D.J., "Incorporating Photodynamic Therapy Into a Medical and Cosmetic Dermatology Practice", *Dermatol. Clin.*, 25:111–118 (2007).

Gold et al., "5–Aminolevulinic Acid Photodynamic Therapy: Where We Have Been and Where We Are Going", *Dermatol. Surg.*, 30:1077–1084 (2004).

Gold et al., "One–Year Follow–Up Using an Intense Pulsed Light Source for Long–Term Hair Removal", *J. Cutan. Laser Ther.*, 1:167–171 (1999).

Gold et al., "Treatment of Wrinkles and Skin Tightening Using Aluma™ Skin Renewal System with FACES™ (Functional Aspiration Controlled Electrothermal Stimulation) Technology",*Aesthetic Buyers Guide,* pp. 1–6 (2005).

Gold, M.H., "Aminolevulinic Acid Photodynamic Therapy: Medical Evidence for Its Expanded Use", *Expert Rev. Med. Devices,* 3:357–371 (2006).

Gold, M.H., "Introduction to Photodynamic Therapy: Early Experience",*Dermatol. Clin.,* 25:1–4 (2007).

Goldberg et al., "Nonablative Treatment of Rhytids With Intense Pulsed Light", *Lasers Surg. Med.,* 26:196–200 (2000).

Goldberg et al., "Q–switched Nd:YAG Laser: Rhytid Improvement by Non–Ablative Dermal Remodeling", *J. Cutan. Laser Ther.,* 2:157–160 (2000).

Goldberg, D.J., "Effect of Temperature–Controlled Cooling on Light–Based Skin Treatments", *J. Cos. Laser Ther.,* 8:155–156 (2006).

Goldberg, D.J., "Erbium: YAG Laser Resurfacing: What Is Its Role?",*Aesth. Surg. J.,* 18(4);255–260 (1998).

Goldberg, D.J., "New Collagen Formation After Dermal Remodeling with an Intense Pulsed Light Source", *J. Cutan. Laser Ther.,* 2:59–61 (2000).

Goldman et al., "600 nm Flash Pumped Dye Laser for Fragile Telangiectasia of the Elderly",*Lasers Surg. Med.,* 13:227–233 (1993).

Goldman et al., "Photothermal Sclerosis of Leg Veins", *Dermatol. Surg.,* 22:323–330 (1996).

Goldman et al., "Pulsed dye laser treatment of telangiectases with and without subtherapeutic sclerotherapy", *J. Am. Acad. Dermatol.,* 23(1):23–30 (1990).

Goldman et al., "Treatment of Cutaneous Vascular Lesions", in *Cutaneous Laser Surgery,* Chapter 2, pp. 19–105 (1994).

Goldman et al., "Treatment of port–wine stains (capillary malformation) with the flashlamp–pumped pulsed dye laser", *J. Pediatrics,* 122(1):71–77 (1993).

Goldman, M.P., "Laser and Noncoherent Pulsed Light Treatment of Leg Telangiectasia and Venules", *Cos. Dermatol.,* 8(10):43–44 (1995).

Goldman, M.P., "Sclerotherapy Treatment for Varicose and Telangiectatic Leg Veins", in *Vascular and Pigmented Abnormalities,* Chapter 17, pp. 256–271 (1997).

Gomer, H., "Military laser burns away skin flaws",*The London Sunday Times,* No. 8929 (Oct. 15, 1995).

Gonzalez et al., "Treatment of telangiectases and other benign vascular lesions with the 577 nm pulsed dye laser", *J. Am. Acad. Dermatol.,* 27(2);220–226 (1992).

Gregory et al., "Effect of Blood Upon the Selective Ablation of Atherosclerotic Plaque with a Pulsed Dye Laser", *Lasers Surg. Med.,* 10:533–543 (1990).

Grevelink et al., "Update on the Treatment of Benign Pigmented Lesions with the Q–Switched Ruby Laser", *Lasers Surg. Med.,* 4:73–74 (Abstract No. 326) (1992).

Groot et al., "Comparison of the infrared coagulator and the carbon dioxide laser in the removal of decorative tattoos", *J. Am. Acad. Dermatol.,* 15:518–522 (1986).

Gustafsson et al., "A Variable Pulsewidth Vascular System for Dermatology",*SPIE,* 2128:188–196 (1994).

Guttman, C., "Novel radiofrequency–based treatment achieves skin tightening with minimal discomfort", http://www.modernmedicine.com, pp. 1–3 (2005).

Harris et al., "Facial skin resurfacing with a very short pulsed $CO_2$ laser: Beam characterization and initial histological results", *SPIE,* 2671:211–218 (1996).

Henderson, B.W., "Photodynamic therapy—coming of age", *Photodermatology,* 6:200–211 (1989).

Henning et al., "Clinical and Histological Evaluation of Portwine Stain Treatment with a Microsecond pulsed Dye–laser at 577 NM", *Lasers Surg. Med.,* 4:375–380 (1984).

Henning et al., "Port Wine Stain Coagulation Experiments with a 540–nm Continuous Wave Dye–laser", *Lasers Surg. Med.,* 2:205–210 (1983).

Henning et al., "Rhinophyma Treated by Argon Laser",*Lasers Surg. Med.,* 2:211–215 (1983).

Henning et al., "Treatment of Keloids and Hypertrofic Scars with an Argon Laser",*Lasers Surg. Med.,* 6:72–75 (1986).

Hilsenrath, J.E., "Investingit; Unsightly Veins? Zap. Wall St. Woes? Zap.",*New York Times,* http://www.nytimes.com, pp. 1–3 (Jun. 23, 1996).

Hruza et al., "Laser Skin Resurfacing",*Arch. Dermatol.,* 132:451–455 (1996).

Hughes, P.S.H., "Multiple Miliary Osteomas of the Face Ablated With the Erbium: YAG Laser",*Arch. Dermatol.,* 135:378–380 (1999).

"Infrared–Coagulator", Lumatec product leaflet, pp. 1–4.

Ishimaru, A., "Diffusion of light in turbid material",*Applied Optics,* 28(12):2210–2215 (1989).

Jacques, S.L., "The Role of Skin Optics in Diagnostic and Therapeutic Uses of Lasers", *Lasers Dermatol.,* pp. 1–21 (1992).

Jaitly et al., "1 MV Long Pulse Generator with Low Ripple and Low Droop",*8$^{th}$ IEEE Int'l Pulsed Power Conf.,* pp. 161–165 (1991).

Jaitly et al., "Design and Testing of Multi–output 300kV Prototype Induction Cell Pulsed Power Supply for Darht", *10$^{th}$ IEEE Int'l Pulsed Power Conf.,* pp. 1412–1421 (1995).

Jay, H.H., "Victory Over Veins", http://www.nytimes.com, pp. 1–2 (Jul. 21, 1996).

Johannigmann et al., "Ein Neues Ultraschall–Kontaktgel", *Geburtsh. U. Frauenheilk,* p. 34 (1974) (in German, with English Abstract Only).

Kalka et al., "Photodynamic Therapy in Dermatology",*J. Am. Acad. Dermatol.,* 42:389–413 (2000).

Kaminester, L.H., "Suntanning Centers",*JAMA,* 244(11):1258–1259 (1980).

Kaufmann et al., "Pulsed 2·94–µm erbium–YAG laser skin ablation—experimental results and first clinical application", *Clin. Exp. Dermatol.,* 15:389–393 (1990).

Keijzer et al., "Laser Beam Diameter for Port Wine Stain Treatment", *Lasers Surg. Med.,* 11:601–605 (1991).

Kennedy et al., "Photodynamic Therapy with Endogenous Protoporphyrin, IX: Basic Principles and Present Clinical Experience",*J. of Photochem. Photobio.,* 6:143–148 (1990).

Kilmer et al., "Pulse Dey Laser Treatment of Rhytids",*Lasers Surg. Med.,* p. 44 (Abstract No. 194) (1997).

Koechner, W., in *Solid State Laser Engineering,* Springer Series in Optical Sciences—vol. 1, Chapters 1–2, pp. 1–620, Springer–Verlag, New York (1976).

Lakmaker et al., "Modeling the Color Perception of Port Wine Stains and its Relation to the Depth of Laser Coagulated Blood vessels", *Lasers Surg. Med.,* 13:219–226 (1993).

Lash et al., "How We Got Here", *Lasers Surg. Med.,* 3:113 (Abstract No. 29) (1983).

Lask et al., "Laser Skin Resurfacing with the SikTouch Flashscanner for Facial Rhytides", *Dermatol. Surg.,* 21:1021–1024 (1995).

Lask et al., "Nonablative laser treatment of facial rhytides", *SPIE*, 2970:338–349 (1997).

Levins et al., "Q–Switched Ruby Laser Treatment of Tattoos", *Lasers Surg. Med.,* Suppl. 3:63–64 (Abstract No. 255) (1991).

Lowe et al., "Skin Resurfacing with the Ultrapulse Carbon Dioxide Laser",*Dermatol. Surg.*, 21:1025–1029 (1995).

Magee et al., "Vein Marking Through Ultrasound Coupling Gel",*Eur. J. Vasc. Surg.*, 4:491–492 (1990).

Majaron et al., "Deep Coagulation of Dermal Collagen with Repetitive Er:YAG Laser Irradiation", *Lasers Surg. Med.,* 26:215–222 (2000).

Majaron et al., "Er:YAG Laser Skin Resurfacing Using Repetitive Long–Pulse Exposure and Cryogen Spray Cooling: 1. Histological Study", *Lasers Surg. Med.,* 28:121–130 (2001).

Majaron et al., "Er:YAG Laser Skin Resurfacing Using Repetitive Long–Pulse Exposure and Cryogen Spray Cooling: II. Theoretical Analysis", *Lasers Surg. Med.,* 28:131–137 (2001).

Margolis et al., "Visible Action Spectrum for Melanin–Specific Selective Photothermolysis", *Lasers Surg. Med.,* 9:389–397 (1989).

Marhic et al., "White–Light Flashlamp–pumped dye laser for photography through endoscopes", *Optics Communications,* 45(1):21–25 (1983).

McCaughan et al., "Photodynamic Therapy for Cutaneous and Subcutaneous Malignant Neoplasms", *Arch. Surg.,* 124:211–216 (1989).

McCaughan et al., "Photodynamic Therapy: An Eight–Year Experience", in *Photodynamic Therapy: Basic Principles and Clinical Applications,* pp. 323–331 (1992).

Meijering et al., "Limits of Radial Time Constants to Approximate Thermal Response of Tissue", *Lasers Surg. Med.,* 13:685–687 (1993).

Miller et al., "Optical Modelling of Light Distributions in Skin Tissue Following Laser Irradiation", *Lasers Surg. Med.,* 13:565–571 (1993).

Milner et al., "Analysis of nonablative skin resurfacing", *SPIE,* 2970:367–373 (1997).

Mordon et al., "Rationale for Automatic Scanners in Laser Treatment of Port wine Stains", *Lasers Surg. Med.,* 13:113–123 (1993).

Morelli et al., "Tunable Dye Laser (577 nm) Treatment of Port Wine Stains",*Lasers Surg. Med.,* 6:94–99 (1986).

Motamedi et al., "Thermal Response of Tissue During Laser Angioplasty", *Lasers Surg. Med.,* 5:172 (Abstract No. 114) (1985).

Mutzhas et al., "A New Apparatus with High Radiation Energy Between 320–460 nm: Physical Description and Dermatological Applications",*J. Invest. Dermatol.,* 76:42–47 (1981).

Nakagawa et al., "Ultrastructural Changes in Human Skin After Exposure to a Pulsed Laser",*J. Invest. Dermatol.,* 84(5):396–400 (1985).

Nestor et al., "New Perspectives on Photorejuvenation", *Skin & Aging,* 11:68–74 (2003).

Newman et al., "Variable Pulse Erbium: YAG Laser Skin Resurfacing of Perioral Rhytides and Side–by–side Comparison with Carbon Dioxide Laser", *Lasers Surg. Med.,* 26:208–214 (2000).

Parrish et al., "Exploring Mechanisms of Specificity in Laser–Tissue Interactions", *Lasers Surg. Med.,* 3:175 (Abstract No. 260) (1983).

Parrish et al., "Spatial Confinement of Thermal Effects of Pulsed Laser Irradiation of Tissue",*Lasers Surg. Med.,* 3:157 (Abstract No. 195) (1973).

Paul et al., "The Effect of Temperature and Other Factors on Selective Microvascular Damage Caused by Pulsed Dye Laser", *J. Invest. Dermatol.,* 81(4):333–336 (1983).

Pfefer et al., "Mechanisms of Laser–Induced Thermal Coagulation of Whole Blood in vitro", *SPIE,* 3590:20–31 (1999).

Philipp et al., "Treatment of Congenital Vascular Disorders: Classification, Step Programme and Therapeutical Procedures", *SPIE,* 2086:228–238 (1993).

Pickering et al., "585 nm for the Laser Treatment of Port Wine Stains: A Possible Mechanism",*Lasers Surg. Med.,* 11:616–618 (1991).

Plewig et al., "A new apparatus for the delivery of high intensity UVA and UVA + UVB irradiation, and some dermatological applications", *Br. J. Dermatol.,* 98:15–24 (1978).

Polla et al., "Tunable Pulsed Dye Laser for the Treatment of Benign Cutaneous Vascular Ectasia", *Dermatologica,* 174:11–17 (1987).

Pottier et al., "Assessment of Non–Coherent Light Sources for Photodynamic Therapy",*SPIE,* 2371:364–368 (1995).

Pratesi, R., "Potential Use of Incoherent and Coherent Light–Emitting–Diodes (LEDs) in Photomedicine", in *Photomedicine, Laser Photobiol. Photomed.,* 22:293–308 (1983).

Ramrus et al., "A Compact One–Half MV Rep–Rate Pulser",*20$^{th}$ IEEE Power Modulator Symposium,* pp. 68–71 (1992).

Ramrus et al., "Design and Performance of a One–half MV Rep–Rate Pulser", Proc. Of the 8$^{th}$ IEEE International Pulsed Power Conference, pp. 982–985 (1991).

Ranganathan et al., "Promises for Ultrasonic Waves on Activity of Silica Gel and Some Supported Catalystes", *Ind. Eng. Chem. Prod. Res. Develop.,* 12:155–158 (1973).

Rassing et al., "Measurement of Ultrasonic Absorption in a Gel by Light Diffraction and Resonator Methods", *J. Mol. Liq.,* 26:97–108 (1983).

Rastegar et al., "Technique for Measurement of One–Dimensional Instantaneous Ablation Velocity", *Lasers Surg. Med.,* 8:533–535 (1988).

Raulin et al., "Treatment of a Nonresponding Port–Wine Stain With a New Pulsed Light Source (PhotoDerm® VL)", *Lasers Surg. Med.,* 21:203–208 (1997).

Raulin et al., "Treatment of Adult Port–Wine Stains Using Intense Pulsed Light Therapy (PhotoDerm VL): Brief Initial Clinical Report", *Dermatol. Surg.,* 23:594–601 (1997).

Raulin et al., "Treatment of benign venous malformations with an intense pulsed light source (PhotoDerm VL)", *Eur. J. Dermatol.,* 7:279–282 (1997).

Raulin et al., "Treatment of Essential Telangiectasias with an Intense Pulsed Light Source (PhotoDerm VL)", *Dermatol. Surg.,* 23:941–946 (1997).

Raulin et al., "Treatment of Port–wine Stains With a Noncoherent Pulsed Light Source", *Arch. Dermatol.,* 135:679–683 (1999).

Reyes et al., "Treatment of port–wine stains during childhood with the flashlamp–pumped pulsed dye laser", *J. Am. Acad. Dermatol.,* 23:1142–1148 (1990).

Ross et al., "Effects of $CO_2$ Laser Pulse Duration in Ablation and Residual Thermal Damage: Implications for Skin Resurfacing",*Lasers Surg. Med.,* 19:123–129 (1996).

Rowe, P.M., "Photodynamic therapy begins to shine",*Lancet*, 351:1496 (1998).

Sadick et al., "Photorejuvenation with Intense Pulsed Light: Results of a Multi–Center Study",*J. Drugs Dermatol.*, 3(1):41–49 (2004).

Sadick, N.S., "A Structural Approach to Nonablative Rejuvenation", *Cosmetic Dermatol.*, 15(12):39–43 (2002).

Sadick, N.S., "Update on Non–Ablative Light Therapy for Rejuvenation: A Review",*Lasers Surg. Med.*, 32:120–128 (2003).

Schamiloglu et al., "Modern Pulsed Power: Charlie Martin and Beyond", *Proceedings of the IEEE*, 92(7):1014–1020 (2004).

Schroeter et al., "An Intense Light Source: The Photoderm VL–Flashlamp as a New Treatment Possibility for Vascular Skin Lesions", *Dermatol. Surg.*, 24:743–748 (1998).

Schroeter et al., "Photoderm VL treatment of leg teleangiectasia",*JEADV*, 5(Suppl. 1):S49 (Abstract No. W76) (1995).

Schwimer et al., "The Effect of Ultrasound Coupling Gels on Sperm Motility In Vitro",*Fertil. Steril.*, 42:946–947 (1984).

Sheean et al., "Arrest of Embryo Development by Ultrasound Coupling Gels",*Fertil. Steril.*, 45:568–571 (1986).

Smith et al., "532–Nanometer Green Laser Beam Treatment of Superficial Varicosities of the Lower Extremities", *Lasers Surg. Med.*, 8:130–134 (1988).

Steiger et al., "Comparison of Different Pulsed and Q–switched Solid–state Laser Systems for Endoscopic Laser Induced Shock Wave Lithotripsy: Performance and Laser/Stone Interactions", *SPIE*, 2300:94–101 (1990).

Strickland et al., "A 5kV, 250 kA Rep–Rated Pulser Using Parallel Ignitrons", *7th IEEE Int'l Pulsed Conf.*, pp. 729–731 (1989).

Sunde et al., "Traumatic Tattoo Removal: Comparison of Four Treatment Methods in an Animal Model with Correlation to Clinical Experience", *Lasers Surg. Med.*, 10:158–164 (1990).

Svaasand et al., "Light and Drug Distribution with Topically Administered Photosensitizers",*Lasers Surg. Med.*, 11:261–265 (1996).

Szeimies et al., "A Possible New Incoherent Lamp for Photodynamic Treatment of Superficial Skin Lesions", *Acta Derm. Venereol (Stockh).*, 74:117–119 (1994).

Tan et al., "Action Spectrum of Vascular Specific Injury Using Pulsed Irradiation", *J. Invest. Dermatol.*, 92(6):868–871 (1989).

Tan et al., "EMLA for Laser Treatment of Portwine Stains in Children",*Lasers Surg. Med.*, 12:543–548 (1992).

Tan et al., "Histologic Responses of Port–wine Stains Treated by Argon, Carbon Dioxide, and Tunable Dye Lasers", *Arch. Dermatol.*, 122:1016–1022 (1986).

Tan et al., "Pulsed Dye Laser Treatment of Recalcitrant Verrucae: A Preliminary Report",*Lasers Surg. Med.*, 13:127–137 (1993).

Tan et al., "Treatment of Children with Port–Wine Stains Using the Flashlamp–Pulsed Tunable Dye Laser", *N. Engl. J. Med.*, 320(7):416–421 (1989).

Taub, A.F., "Photodynamic Therapy: Other Uses", *Dermtol. Clin.*, 25:101–109 (2007).

Taylor et al., "Q–Switched Ruby Laser (QSRL) Irradiation of Benign Pigmented Lesions: Dermal vs. Epidermal", *Lasers Surg. Med.*, 3:65 (Abstract No. 262) (1991).

Templeton et al., "Comparison of infrared coagulation and rubber band ligation for first and second degree haemorrhoids: a randomized prospective clinical trial", *Br. Med. J.*, 286:1387–1389 (1983).

Troccoli et al., "Multiple–Pulse Photocoagulation of Blood Vessels With A 585 Nm Tunable Laser", *Lasers Surg. Med.*, 4:3 (Abstract No. 2) (1992).

van Gemert et al., "Can Physical Modeling Lead to an Optimal Laser Treatment Strategy for Port–Wine Stains", in *Laser Applications in Medicine and Biology*, Chapter 5, pp. 199–247, Plenum Press, New York (1991).

van Germert et al., "Instantaneous Ablation Behavior of In–Vitro Rods During Laser Irradiation", *Lasers Surg. Med.*, 5:136 (Abstract No. 4) (1985).

van Germert et al., "Is There an Optimal Laser Treatment for Port Wine Stains?", *Lasers Surg. Med.*, 6:76–83 (1986).

van Germert et al., "Wavelengths for Laser Treatment of Port Wine Stains and Telangiectasia", *Lasers Surg. Med.*, 16:147–155 (1995).

"Varicose Vein Device Producer comes to U.S. Market", *Clinica*, 687:9 (Jan. 8, 1996).

Venning et al., "Tattoo removal using infra–red coagulation: a dose comparison", *Br. J. Dermatol.*, 117:99–105 (1987).

Wagner et al., "Percutalgine–Gel et Ultrasonotherapie en Pathologie du Sport", *La Revue de Medecine*, 32:1681–1683 (1982) (in French, with English Abstract Only).

Waldorf et al., "Skin Resurfacing of Fine to Deep Rhytides Using a Char–free Carbon Dioxide Laser in 47 Patients", *Dermatol. Surg.*, 21:940–946 (1995).

Walsh et al., "Er:YAG Laser Ablation of Tissue: Measurement of Ablation Rates", *Lasers Surg. Med.*, 9:327–337 (1989).

Walsh et al., "Pulsed $CO_2$ Laser Tissue Ablation: Effect of Tissue Type and Pulse Duration On Thermal Damage", *Lasers Surg. Med.*, 8:108–118 (1988).

Walsh, J.T., "Er:YAG Laser Ablation of Tissue: Effect of Pulse Duration and Tissue Type on Thermal Damage", *Lasers Surg. Med.*, 9:314–326 (1989).

Walsh, J.T., "Pulsed Laser Ablation of Tissue: Analysis of the Removal Process and Tissue Healing", *Unpublished Ph.D. dissertation Massachusetts Institute of Technology, on file with Institute Archives and Hayden Library, Massachusetts Institute of Technology*, pp. 1–312 (1988).

Weiss et al., "Rejuvenation fo Photoaged Skin: 5 Years Results with Intense Pulsed Light of the Face, Neck, and Chest", *Dermatol. Surg.*, 28:1115–1119 (2002).

Welch et al., "Practical Models for Light Distribution in Laser–Irradiated Tissue", *Lasers Surg. Med.*, 6:488–493 (1987).

Werner et al., "Die Hamangiombehandlung mit dem Neodym: Yttrium–Aluminium–Granat Laser (Nd:YAG–Laser)", *Laryngo–Rhino–Otol.*, 71:388–395 (1992), (in German, with English Abstract Only).

West, T., "How Laser Surgery Can Help Your Rosacea Patients", *Skin & Aging*, pp. 43–46 (1998).

Wilder, D., "Pulsed 1064–nm Nd:YAG Laser Therapy for Noninvasive Treatment of a Massive Hemangioma: Case Report", *J. Clin. Laser Med. Surg.*, 17(6):245–247 (1999).

Wilson et al., "The physics of photodynamic therapy", *Phys. Med. Biol.*, 31(4):327–360 (1986).

"Sharplan 771 Microscan Data Sheet", Mar. 28, 1985.

Alster et al., "Improvement of facial acne scars by the 585 nm flashlamp–pumped pulsed dye laser", *Journal of the American Academy of Dermatology*, 35(1):79–81 (Jul, 1996).

Alster et al., "Treatment of Scars: A Review", *Annuals of Plastic Surgery*, 39(4):418–432 (Oct. 1997).

Anderson et al., "Selective Photothermolysis: Precise Microsurgery by Selective Absorption of Pulsed Radiation", *Science*, 220:524–527 (Apr. 1993).

Anderson et al., "Pulsed photothermal radiometry in turbid media: internal reflection of backscattered radiation strongly influences optical dosimetry", *Applied Optics*, 28(12):2256–2262 (1989).

Anderson et al., "Microvasculature can be selectively damaged using dye lasers: basic theories and experimental evidence in human skin", *Laser in Surg. Med.*, 1:263–276 (1981).

Arthrex, Inc., "Single Use Shaver Blades and Burs", (1996).

Birngruber et al., "Fundus Reflectometry: A Step towards Optimization of the Retina Photocoagulation", *Mod. Probl. Ophthal.*, 18:383–390 (1977).

Blitzer, "Laser Photocoagulation in the Care of Patients with Osler–Weber–Rendu Disease", *Operative Techniques in Otolaryngology—Head and Neck Surgery*, 5(4):274–277 (Dec. 1994).

Boutnois, "Photophysical Processes in Recent Medical Laser Developments: A Review", *Lasers in Medical Science*, 1:47–64 (1986).

Brauner et al., "Treatment of Pigmented Lesions with the Flashlamp Pumped PL DL ("Brown Spot") Laser", *Laser Med. And Surgery Abstracts*, 4:73 (Sep. 1992).

Cisneros et al., "The Q–switched Neodymium (Nd): YAG Laser with Quadruple Frequency", *Dermatol. Surg.*, 24:345–350 (1998).

Dagan et al., "Microprocessor–Controlled Scanning Micromanipulator for Carbon–Dioxide Laser Surgery", *J. Neurosurgery*, 59:1098–1099 (Dec. 1983).

Fitzpatrick et al., "Treatment of Benign Cutaneous Pigmented Lesions with the Candela 510 NM Pulsed Laser", *Laser Med. and Surgery Abstracts*, 4S:73 (Sep. 1992).

Frauchiger et al., "Laser properties of selectively excited YA1O$_3$:Er", *Optic Letters*, 13(11):964–966 (1988).

Gabay et al., "Modelling the Assessment of Port Wine Stain Parameters From Skin Surface Temperature Following a Diagnostic Laser Pulse", *Lasers in Surgery and Medicine*, 20(2):179–187 (1997).

Geeraets et al., "Light Reflectance of the Ocular Fundus", *Archives of Ophthalmology*, 69:612–617 (May 1963).

Gustafsson et al., "A Variable Pulsewidth Vascular System for Dermatology", *SPIE*, 2128:186–196 (1994).

Hacker et al., "The Effect of Flash Lamp–Pulsed Dye Laser on Psoriasis", *Archives of Dermatology*, 128:853–855 (Jun. 1992).

Herloski et al., "Gaussian beam ray–equivalent modeling and optical design", *Applied Optics*, 22(8):1168–1174 (1983).

International Search Report, dated Jul. 24, 1996, for International Application No. PCT/US96/04515, 4 pages.

Ishimaru, "Diffusion of Light in Turbid Material", *Applied Optics*, 28(12):2210–2215 (1989).

Jacques et al., "The Role of Skin Optics in Diagnostic and Therapeutic Uses of Lasers", *Lasers in Dermatology*, 1–21 (1991).

Jerath et al., "Calibrated real–time control for lesion size based on reflectance images", *Applied Optics*, 32(7):1200–1209 (Mar. 1993).

Jerath et al., "Reflectance Feedback Control of Photocoagulation In Vivo", *Arch Ophthalmol*, 111:531–534 (Apr. 1993).

Jeys et al., "Sum frequency generation of sodium resonance radiation", *Applied Optics*, 28(13):2588–2591 (1989).

Kaufman et al., "Clinical Evaluation of Pulsed Erbium: YAG Laser Ablation in Cutaneous Surgery", (Abstract), Partly Presented at 15th Annual Mtg of the American Society for LaserMedicine and Surgery, (1995).

Kauvar et al., "Laser Therapy for Cutaneous Vascular Lesions", *Operative Techniques in Otolaryngology—Head and Neck Surgery*, 5(4):250–258 (Dec. 1994).

Kienle et al., "Why do veins appear blue? A new look at an old question", *Applied Optics*, 35(7):1151–1160 (1996).

Lahaye et al., "Optimal laser parameters for port wine stain therapy: a theoretical approach", *Phys. Med. Biol.*, 30(6):573–587 (1985).

LaserSight Centers brochure, "CENTAURI.TM. Ophthalmic Erbium:Yag Laser", (Nov. 1993).

Lesinski et al., "Carbon Dioxide Lasers for Otosclerosis", *Otolaryngologic Clinics of North America*, 26(3)417–441 (Jun. 1993).

Lewis et al., "Backscattering target detection in a turbid medium by polarization discrimination", *Applied Optics*, 38(18):3937–3944 (Jun. 1999).

Lytle et al., "Improved Efficacy of SnET2 Mediated PDT With the Simultaneous Application of Selective Laser–Indused Hyperthermia", *SPIE Proceedings*, 2392–6:15–22.

Maloney et al., "Laser Otology", *Operative Techniques in Otolaryngology—Head and Neck Surgery*, 3(2):74–83 (Jun. 1992).

Milner et al., "Depth determination of chromophores in human skin by pulsed photothermal radiometry," *Applied Optics*, 35(19):3379–3385 (Jul. 1996).

Milner et al., "Depth profiling of laser–heated chromophores in biological tissues by pulsed photothermal radiometry", *Journal of the Optical Society of America A*, 12(7):1479–1488 (Jul. 1995).

Minamihaba et al., "Double–Level CU Inlaid Interconnects with Simultaneously Filled Viaplugs" *Japanese Journal of Applied Physics*, 35(2B):1107–1110 (Feb. 1996).

Mordon et al., "Relation Betwen Skin Surface Temperature and Minimal Blanching During Argon, Nd–YAG 532, and CW Dye 585 Laser Therapy of Port–Wine Stains," *Lasers in Surgery and Medicine*, 13(1):124–126 (1993).

Morrell et al., "Tunable Dye Lasers (577 nm) Treatment of Port Wine Stains", *Lasers Surg. Med.*, 6(1):94–99 (1986).

Orenberg et al., "Comparison of heat delivery systems for hyperthermia treatment of psoriasis", *Int. J. Hyperthermia*, 2(3):231–241 (1986).

Pai et al., "Selective Electroless Copper for FLSI Interconnection", *IEEE Electron Device Letters*, 10(9):423–425 (1989).

Patent Abstracts of Japan, vol. 012, No. 337 (E–657), Sep. 12, 1988 & JP 63 100749 A (Hitachi Ltd.), May 2, 1988.

Patent Abstracts of Japan, vol. 016, No. 264 (D–1216), Jun. 15, 1992 & JP 04 61125 A (Kanegafuchi Chem. Ind. Co. Ltd.), Feb. 27, 1992.

Patent Abstracts of Japan, vol. 018, No. 480 (E–1603), Sep. 8, 1994 & JP 06 164140 A (Ibiden Co. Ltd.), Jun. 10, 1994.

Patent Abstracts of Japan, vol. 4, No. 172 (P–038), Sep. 9, 1980.

Petrovich et al., "Relationship of Response to Transurethral Hyperthermia and Prostate Volume in BPH Patients", *Urology*, 40(4):317–321 (Oct. 1992).

Pomerantzeff et al., "A Method to Predetermine the Correct Photocoagulation Dosage", *Arch Ophthalmol*, 101:949–953 (1983).

Pomerantzeff et al., "Time and Location Analysis of Lesion Formation in Photocoagulation", *Arch Ophthalmol*, 101:954–957 (1983).

Sausville et al., "Blue Lamps in Phototherapy of Hyperbilirubinemia", *Journal of IES*, 112–118 (1972).

Semm et al., "Tissue Morcellation In Endoscopic Surgery", *Surgical Technology International V, International Developments In Surgery & Surgical Research*, 175–178. (1996).

Slatkin et al., "Instrumentation for Office Laser Surgery", *Operative Techniques in Otolaryngology—Head and Neck Surgery*, 5(4);211–217 (Dec. 1994).

Smith & Naphew, Inc., "Shaver Systems–Endoscopic Powered Instrument System", Mar. 1997.

Smith et al., "The Design of Optical Systems", *Modern Optical Engineering*, 273–278 (1990).

Smithies et al., "The Effect of the Illumination Time When Treating Port–wine Stains", *Lasers in Medical Science*, 10(2):93–104 (1995).

Taylor et al., "Light & Electron Microscopic Analysis of Tattoos Treated by O–Switched Ruby Laser", *J. of Investigative Dermatology*, 97:131–136 (1991).

Van–Gemert et al. "Treatment of Port–Wine Stains: Analysis", *Medical Instrumentation*, 21:213–217 (1987).

Waldow et al., "Nd: YAG Laser–Induced Hyperthermia in a Mouse Tumor Model", *Lasers in Surgery and Medicine*, 8(5):510–514 (1988).

Weinberg et al., "The Change in Light Reflection of the Retina During Therapeutic Laser–Photocoagulation," *IEEE J. Quantum Electronics*, QE–20(12):1481–1489 (1984).

Wright et al., "Initial in vivo results of hybrid retinal photocoagulation system", *Journal of Biomedical Optics*, 5(1);56–61 (Jan. 2000).

Yang et al., "Automatic Control of Lesion Size in a Simulated Model of the Eye", *IEEE Journal of Quantum Electronics*, 26(12);2232–2239 (1990).

Yang et al., "Reflectance as an Indirect Measurement of the Extent of Laser–Induced Coagulation," *IEEE Transactions on Biomedical Engineering*, 37(5):466–473 (1990).

Zee et al., "Whole–Body Hyperthermia in Cancer Therapy: A Report of A Phase I–II Study" *Eur. J., Cancer Clinical Oncology*, 19(9):1189–1200 (1983).

Zimmer information brochure, "Arthroscopic Blades and Burrs", (1996).

File history for EP0565331, Various Dates.

Deposition transcript of Lars Ake Morgan Gustavsson (Dec. 10, 2007).

*Lumenis Ltd., et al. v. Alma Ltd., et al.*, 07–CV3622, N.D.Ill.—Complaint (Jun. 28, 2007).

*Lumenis Ltd., et al. v. Alma Ltd., et al.*, 07–CV3622, N.D.Ill.—Joint Claim Construction Statement (Jan. 4, 2008.

*Lumenis Ltd., et al. v. Alma Ltd., et al.*, 07–CV3622, N.D.Ill.—Plaintiffs' Opening Claim Construction Brief) (Jan. 7, 2008).

*Lumenis Ltd., et al. v. Alma Ltd., et al.*, 07–CV3622, N.D.Ill.—Plaintiffs' Reply to Defendants' Responsive Claim Construction Brief (Jan. 22, 2008).

*Lumenis Ltd., et al. v. Alma Ltd., et al.*, 07–CV3622, N.D.Ill.—Plaintiffs' Demonstratives for Markman Hearing (Jan. 23, 2008).

*Lumenis Ltd., et al. v. Alma Ltd., et al.*, 07–CV3622, N.D.Ill.—Defendants' Amended Answer, Affirmative Defenses, and Counterclaims (Jan. 25, 2008).

*Lumenis Ltd., et al. v. Alma Ltd., et al.*, 07–CV3622, N.D.Ill.—Plaintiffs' Reply to Defendants' Counterclaim (Feb. 14, 2008).

*Lumenis Ltd., et al. v. Alma Ltd., et al.*, 07–CV3622, N.D.Ill.—Plaintiffs' Further Supplemental Answers to Defendants' First Set of Interrogatories to Plaintiffs (Nos. 3 an 11) (Feb. 1, 2008).

*Lumenis Ltd., et al. v. Alma Ltd., et al.*, 07–CV3622, N.D.Ill.—Plaintiffs' Rule 26(a)(1) Initial Disclosures to Defendants (Oct. 29, 2007).

*Lumenis Ltd., et al. v. Alma Ltd., et al.*, 07–CV3622, N.D.Ill.—Defendants' Initial Disclosures Pursuant to Fed. R. Civ. P. 26(a) (Oct. 29, 2007).

*Lumenis Ltd., et al. v. Alma Ltd., et al.*, 07–CV3622, N.D.Ill.—Plaintiffs' Answers to Defendants' First Set of Interrogatories to Plaintiffs (Nov. 19, 2007).

*Lumenis Ltd., et al. v. Alma Ltd., et al.*, 07–CV3622, N.D.Ill.—Plaintiffs' Supplemental Answers to Defendants' First Set of Interrogatories to Plaintiffs (Nos. 2, 5, 8 & 15) (Dec. 14, 2007).

*Lumenis Ltd., et al. v. Alma Ltd., et al.*, 07–CV3622, N.D.Ill.—Plaintiffs' Further Supplemental Answers to Defendants' First Set of Interrogatories to Plaintiffs (Nos. 7, 11, and 12) (Dec. 21, 2007).

*Lumenis Ltd., et al. v. Alma Ltd., et al.*, 07–CV3622, N.D.Ill.—Plaintiffs' Further Supplemental Answers to Defendants' First Set of Interrogatories to Plaintiffs (No. 3) (Dec. 27, 2007).

*Lumenis Ltd., et al. v. Alma Ltd., et al.*, 07–CV3622, N.D.Ill.—Plaintiffs' Answers to Defendants' Second Set of Interrogatories to Plaintiffs (Nos. 16–18) (Dec. 28, 2007).

*Lumenis Ltd., et al. v. Alma Ltd., et al.*, 07–CV3622, N.D.Ill.—Plaintiffs' Supplemental Answers to Defendants' Second Set of Interrogatories to Plaintiffs (No. 18) (Jan. 14, 2008).

"Aesthetic CO2 Laser System", literature, 2 pages, (Aug. 1994).

"New Laser for Microlaryngeal Surgery", *I.L.. Med. Newsletter*, 1(1) (Spring 1991).

"The Er:YAG Laser System for ophthalmic microsurgery", *Aesculap Meditec brochure*, 2 pages, (Oct. 1994).

"The Proven Solution for Disk, Spinal Cord and Brain Microsurgery", *I. L. Med. Unilase product info. Brochure* (1993).

"The Proven Solution for Otologic and Microlaryngeal Surgery", *I. L. Med. Unilase product info. Brochure* (1993).

"Using a CO2 Laser During Conventional Microdiskectomy Shows Promise of Faster Recovery", *I.L. Med. Newsletter*, 1(4) (Spring 1991).

"Control of Pulse Duration and Pulse Sequence Delays for Effective Photo–Epilation", *EpiLight™ Application Notes*, 3(2) (1997).

Adrian, "LightSheer™ 800 NM Pulsed. High–Power Diode Laser Hair Removal System", (2002).

Adrian, "Tissue Effects of a New Long Pulse Frequency Doubled 532 nm Neodymium: YAG Laser on Vascular Lesions", (2001).

Adrian, "Treatment of Facial Telangiectasia Using the VersaPulse® Variable Pulse Width Frequency Doubled Neodymium:YAG Laser: A Case Report", (2001).

Anderson et al., "Microvasculature Can Be Selectively Damaged Using Dye Lasers: A Basic Theory and Experimental Evidence in Human Skin", *Laser in Surgery and Medicine,* 1:263–276 (1981).

Anderson et al., "The Optics of Human Skin", *The Journal of Investigative Dermatology,* 77(1);13–19 (Jul. 1981).

Anderson, "Laser Hair Removal—A Lecture Presented to the 77*th* Congress of the Japan Society of Aesthetic Surgery", (Nov. 1999).

Bandel, "Effective Resolution of a Mature Port–Wine Stain Using PhotoDerm®VL", *Clinical Application Notes,* 1(2) (1998).

Bartley et al., "An Experimental Study to Compare Methods of Eyelash Ablation", *Ophthalmology,* 94(10);1286–1289 (Oct. 1987).

Battle et al., "Study of Very Long–Pulsed (100 ms) High–Powered Diode Laser for Hair Reduction on All Skin Types", (2002).

Beasley et al., "New Parameters for Intense Pulsed Light Rejuvenation With a Thermoelectrically Chilled Crystal Delivery System", *Cosmetic Dermatology,* 15(7):14–16 (Jul. 2002).

Bitter, "Noninvasive Rejuvenation of Photodamaged Skin Using Serial, Full–Face Intense Pulsed Light Treatments", *Dermatol Surg.,* 26(9):835–43 (Sep. 2000).

Campos et al., "Use of an 800 nm High–power Diode Laser for the Treatment of Leg Vein Telangiectasia", (2002).

Campos, "Safe and Effective Long–Term Hair Reduction in Tanned Patients Using an 800 nm Diode Laser", (2002).

Del Giglio, "Hair Removal Using a Combination of Electrical and Optical Energies—3–Month Clinical Study", 1–4 (Not Dated).

Del Giglio, "Hair Removal Using a combination of Electrical and Optical Energies: Multiple Treatments Clinical Study—Six–Month Follow up", 1–4 (Not Dated).

Dierickx et al., "Effective, Permanent Hair Reduction Using Pulsed, High–Power Diode Laser", (2002).

Dierickx, "Laser Hair Removal: Scientific Principles and Practical Aspects", (2002).

Dover et al., "Pigmented Guinea Pig Skin Irradiated with Q–Switched Ruby Laser Pulses", *Arch Dermatol,* 125(1);43–44 (Jan. 1989).

Dréno et al., "The Benefit of Chilling in Argon–Laser Treatment of Port–Wine Stains", *Plast Reconstr Surg.,* 75(1);42–45 (Jan. 1985).

Dzubow, "Leg Veins and Stretch Marks—Have They Seen the Light?", *Dermatol Surg.,* 22(4):321 (Apr. 1996).

Eckhouse et al., "The Application of Selective Photothermolysis in Treating Leg Veins and Other Benign Vascular Lesions", (Apr. 1996).

ESC Medical Systems, "Eliminating Multicolored Tattoos with PhotoDerm® PL", *PhotoDerm® PL Application Notes,* 2(2) (1997).

ESC Medical Systems, "Facial and truncal angiomas—treating patients quickly and effectively", *PhotoDerm® Application Notes,* 1(2) (1996).

ESC Medical Systems, "How does it look in theory?", (1996).

ESC Medical Systems, "Significance of Wavelength Range for Effective Hair Photo–Epilation", *EpiLight Hair Removal System Application Notes,* 3(1) (1997).

ESC Medical Systems, "Superior Treatment of Benign Pigmented Lesions with PhotoDerm® PL", *PhotoDerm® PL Application Notes,* 2(1) (1997).

ESC Medical Systems, "Why are leg veins so difficult to treat?", *PhotoDerm®VL Application Notes,* 1(1) (1996).

Gilchrest et al., "Chilling Port Wine Stains Improves the Response to Argon Laser Therapy", *Plast Reconstr Surg.,* 69(2):278–83 (Feb. 1982).

Gold et al., "Intense Pulsed Light (IPL™) System Enables Successful Treatment of Skin Type VI", *Clinical Application Notes,* 2(5) (2000).

Gold et al., "Long–term epilation using the EpiLight broad band, intense pulsed light hair removal system", *Dermatol Surg.,* 23(10):909–913 (Oct. 1997).

Gold, "Treatment of Larger and Deeper Varicosities Utilizing a 1064 nm Laser System", *Cosmetic Dermatology,* (Nov. 2000).

Goldman, "Effects of New Laser Systems on the Skin" *Arch. Dermatol.,* 108:385–390 (Sep. 1973).

Goldman et al., "Impact of the Laser on Nevi and Melanomas", *Arch Dermatol,* 90:71–75 (Jul. 1964).

Goldman et al., "Laser Treatment of Tattoos—A Preliminary Survey of Three Year's Clinical Experience", *JAMA,* 201(11):163–166 (Sep. 1967).

Goldman et al., "Long–Term Laser Exposure of a Senile Freckle", *Arch. Environ. Health,* 22:401–403 (Mar. 1971).

Goldman et al., "Pathology of the Effect of the Laser Beam on the Skin", *Nature,* 197:912–914 (Mar. 1963).

Goldman et al., "Photothermal Sclerosis of Leg Veins", *Dermatol Surg.,* 22(4):323–30 (Apr. 1996).

Goldman et al., "Preliminary Investigation of Fat Embolization from Pulsed Ruby Laser Impacts of Bone", *Nature,* 221:361–363 (Jan. 1969).

Goldman et al., "Radiation from a Q–Switched Ruby Laser, Effect of Repeated Impacts of Power Output of 10 Megawatts on a Tattoo of Man", *The Journal of Investigative Dermatology,* 44:69–71 (Jan. 1965).

Goldman et al., "Replica Microscopy and Scanning Electron Microscopy of Laser Impacts on the Skin", *The Journal of Investigative Dermatology,* 52(1):18–24 (Jan. 1969).

Goldman et al., "The Biomedical Aspects of Lasers", *JAMA,* 188(3);230–234 (Apr. 1964).

Goldman et al., "The Effect of Repeated Exposures to Laser Beams", *Acta derm.–venereol,* 44:264–268 (1964).

Goldman et al., "Treating Varicose and Telangiectatic Leg Veins", *Federal Practitioner,* (Mar. 1997).

Goldman et al., "Treatment of Basal Cell Epithelioma by Laser Radiation", *JAMA,* 189:773–5 (Sep. 1964).

Goldman, "Dermatologic manifestations of laser radiation", S92–S93 (Not Dated).

Goldman, "Laser Surgery for Skin Cancer", *New York State Journal of Medicine,* (Oct. 1977).

Goldman, "One Laser For A Cosmetic Dermatologic Practice", *Cosmetic Dermatology,* 15(7):49–50 (Jul. 2002).

Goldman, "Surgery by Laser for Malignant Melanoma", *J. Dermatol. Surg. Oncol.,* 5(2) (Feb. 1979).

Goldman, "The Skin", *Arch Environ Health,* 18:434–436 (Mar. 1969).

Herloski et al., "Gaussian beam ray–equivalent modeling and optical design", *Applied Optics,* 22(8):1168–1174 (Apr. 1983).

Huang et al., "Intense Pulsed Light for the Treatment of Facial Freckles in Asian Skin", *Dermatol Surg.,* 29(11);1008–1012 (Nov. 2002).

Hunt et al., "Treatment of Large Body Areas with EpiLight® Hair Removal System: Multi–Center Back Epilation", *Clinical Application Notes*, 2(2):1–4 (1998).

Inderfurth et al., "Dynamic Reflectometer for Control of Laser Photocoagulation on the Retina", *Lasers in Surgery and Medicine*, 15(1)54–61 (May 1994).

Jay, "Photo–Epilation with the EpiLight™ Hair Removal System: Multi–case Study", *Clinical Application Notes*, 2(3) (1998).

Johnson et al., "Intense pulsed light treatment of hirsutism: case reports of skin phototypes V and VI", *Journal of Cutaneous Laser Therapy*, 1:233–237 (1999).

Karpen, "Treating Benign Vascular Lesions of the Lower Extremities: Past, Present, and Future", *Journal of Clinical Laser Medicine & Surgery*, 12(2):111–112 (1994).

Kautz et al., "Early Intervention in Pediatric Hemangiomas with the VascuLight™ Intense Pulsed Light/Laser Source", *Clinical Application Notes*, 8(4) (2000).

Kazmi, "Laser Hair Removal with an 800nm Diode Laser—A Retrospective Study of 1000 Women with Skin Types II to VI", (Jun. 2002).

Klavuhn, "Coverage Rate: The Influence of Laser Parameters on Treatment Time", *Laser Hair Removal Note No. 3*, (Mar. 2000).

Klavuhn, "Epidermal Protection: A Comparative Analysis of Sapphire Contact and Cryogen Spray Cooling", *Laser Hair Removal Technical Note No. 1*, (Jan. 2000).

Klavuhn, "Illumination Geometry: The Importance of Laser Beam Spatial Characteristics", *Laser Hair Removal Technical Note No. 2*, (Feb. 2000).

Kono et al., "Diode Laser–Assisted Hair Removal in Asians: A Study of 101 Japanese Patients", (2000).

Kreindel et al., "Electro–Optical Synergy (ELOS™) Technology for Aesthetic Medicine—Light Triggering Effect on FR Selectivity", 1–4, (Not Dated).

Kreindel et al., "Electro–Optical Synergy (ELOS™) Technology for Aesthetic Medicine Advantages and limitations of various forms of electromagnetic energy for safe and effective hair removal", 1–4 (Not Dated).

Kuriloff et al., "Pharyngoesophageal hair growth: The role of laser epilation", *Otolaryngol Head Neck Surg.*, 98(4):342–5 (Apr. 1988).

Lask et al., "The role of laser and intense light sources in photo–epilation: a comparative evaluation", *Journal of Cutaneous Laser Therapy*, 1:3–13 (1999).

Laughlin, "Effective Epilation of a white hair using combined radio–frequency and optical energy", (Not Dated).

Laughlin, "Epilation in dark skin (types V and VI) with integrated radio–frequency and optical energy", 23–26 (Not Dated).

Levy, "Intense pulsed light treatment for chronic facial erythema of systemic lupus erythematosus: a case report", *Journal of Cutaneous Laser Therapy*, 2(4):195–198 (Dec. 2000).

Lou et al., "Prospective Study of Hair Reduction by Diode Laser (800nm) with Long–Term Follow–Up", *Dermatol Surg.*, 26(5):428–432 (May 2000).

Lumenis Inc., "IPL Skin Treatments using Photorejuvenation: helps restore the skin's youthful look", (2002).

Lumenis Inc., "VascuLight: Intense Pulsed Light and Laser Technology", (2002).

Lumenis Inc. "VascuLight Elite: Intense Pulsed Light and Laser Technology", (2002).

McCoy et al., "An Evaluation of the Copper–Bromide Laser for Treating Telangiectasia", *Dermatol. Surg.*, 22:551–557 (1996).

Moraga, "European Multi–Center Study: VascuLight® for the Treatment of Varicose Veins and Leg Telangiectasias, as well as Other Vascular Lesions", *Clinical Application Notes*, 8(1) (2001).

Moretti, "IPL Photorejuvenation Popularity Spreads Rapidly", *Aesthetic Buyers Guide*, (Mar. 2001).

Moretti, "Laser–Based Technology Expands Treatment Options", *Medical Laser Insight*, (Apr. 1997).

Negishi et al., "Full–Face Photorejuvenation of Photodamged Skin by Intense Pulsed Light with Integrated Contact Cooling: Initial Experiences in Asian Patients", *Lasers in Surgery and Medicine*, 30(4):298–305 (2002).

Negishi et al., "Photorejuvenation for Asian Skin by Intense Pulsed Light", *Dermatol Surg*, 27:7:627–32 (Jul. 2001).

Nestor et al., "Photorejuvenation Non–Ablative Skin Rejuvenation Using Intense Pulse Light"(Not dated).

Pardo et al., "Use of the LightSheer™ Diode Laser System for Hair Reduction: Safety and Efficacy in a Large Series of Treatments", (Feb. 2001).

Parrish et al., "Selective Thermal Effects with Pulsed Irradiation from Lasers: From Organ to Organelle", *The Journal of Investigative Dermatology*, 80(6): 75s–80s (Jun. 1963).

Pervaiz et al., "A New Method of Quantitating Damage to the Hair Shaft: Its Application to Ultraviolet– and Radio Frequency–Treated Hair", *Annals New York Academy of Sciences*, 642:491–2 (Dec. 1991).

Polla et al., "Melanosomes Are a Primary Target of Q–Switched Ruby Laser Irradiation in Guinae Pig Skin", *The Journal of Investigative Dermatology*, 89(3):281–6 (Sep. 1987).

Raulin et al., "Treatment of a Nonresponding Port–Wine Stain With a New Pulsed Light Source (PhotoDerm®VL)", *Lasers Surg Med.*, 21(2);203–8 (1997).

Raulin et al., "Effective Treatment of Hypertrichosis with Pulsed Light: A Report of Two Cases", *Annals of Plastic Surgery*, 39(2):169–173 (Aug. 1997).

Raulin et al., "Photoderm VL®—efficiency and limitations of an intense pulsed light source", *Australasian Journal of Dermatology*, 38(2) (Jun. 1997) (Abstract Only).

Raulin et al., "Treatment of Adult Port–Wine Stains Using Intense Pulsed Light Therapy (PhotoDerm®VL): Brief Initial Clinical Report", *Dermatol Surg.* 23(7):594–7 (Jul. 1997).

Raulin et al., "Treatment of benign venous malformation with an intense pulsed source (PhotDerm®VL)", Europena Journal of Dermatology 7(4):279–285 (Jun. 1997).

Riggle et al., "Laser Effects on Normal and Tumor Tissue", 35–63 (Not Dated).

Sadick et al., "Advances in Laser Surgery for Leg Veins: Bimodal Wavelength Approach to Lower Extremity Vessels, New Cooling Techniques, and Longer Pulse Durations", *Dermatol Surg.*, 28:1:16–20 (Jan. 2002).

Sadick et al., "Long–term Photoepilation Using a Broad–spectrum Intense Pulsed Light Source", *Arch Dermatol*, 136:1336–1340 (Nov. 2000).

Sadick, "A dual wavelength approach for laser/intense pulsed light source treatment of lower extremity veins", *J Am Acad Dermatol*, 46(1):66–72 (Jan. 2002).

Sadick, "The Role of Combined Intense Pulsed Light/Radiofrequency Technology in the Management of Blond and White Hair Photoepilation", (Feb. 8, 2003, ISHR, Aspen, Colorado).

Schroeter et al., "An Intense Light Source", *Dermatol Surg.*, 24:743–748 (1998).

Shimbashi et al., "Ruby Laser Treatment of Pigmented Skin Lesions", *Aesth. Plast. Surg.*, 19(3):225–9 (1995).

Svaasand et al., "On the physical rationale of laser induced hyperthermia", 65–81 (Not Dated).

Taylor et al., "Treatment of Tattoos by Q–Switched Ruby Laser", *Arch Dermatol*, 126(7): 893–9 (Jul. 1990).

Troxler, "One Clinic's Experience in the Treatment of Varicose Veins and Leg Telangiectasias with the VascuLight™ Intense Pulsed Light / Nd:YAG Laser Source", *Clinical Application Notes*, 8(3) (2001).

Waldman et al., "Cutaneous inflammation: Effects of hydroxy acids and eicosand inhibitors on vascular permeability", *The Journal of Investigative Dermatology*, 88:523 (1987) (Abstract Only).

Warren, "Pigmentation induction by melanocyte stimulating hormone in human skin culture", *The Journal of Investigative Dermatology*, 88:523 (1987) (Abstract Only).

Wastek et al., "Characterization of H–substance P (SP) binding to a mouse monoclonal mast cell line", *The Journal of Investigative Dermatology*, 88:523 (1987) (Abstract Only).

Watanabe et al., "The effect of pulse duration on selective pigmented cell injury by dye lasers", *The Journal of Investigative Dermatology*, 88:523 (1987) (Abstract Only).

Weir et al., "Photo–assisted epilation—review and personal observations", *Journal of Cutaneous Laser Therapy*, 1:135–143 (1999).

Weiss et al., "Intense pulsed light: newer perspective", *Dermatol. Surg.*, 23(10):941–945 (1997).

Weiss et al., "New Treatment for Telangiecases and Venulactases: Status of Intense Pulsed Light Therapy", (Not Dated).

Weiss et al., "Sclerotherapy in the U.S.", *Dermatol. Surg.*, 21:393–396 (1995).

Weissman et al., "Growth, collagen and glycosaminoglycan synthesis by dermal fribroblasts derived from puva treated and psoriatic patients", *The Journal of Investigative Dermatology*, 88:523 (1987) (Abstract Only).

Welsh et al., "Evaluation of Cooling Techniques for the Protection of the Epidermis During ND–YAG Laser Irradiation of the Skin", *Neodymium–YAG Laser in Medicine and Surgery*, (1983).

Werner et al., "New possibilities of epilation with a high energy flash lamp", (Not Dated).

Wertz et al., "Effects of essential fatty acid deficiency on the structure and function of epidermal lipids", *The Journal of Investigative Dermatology*, 88:523 (1987) (Abstract Only).

Wheeland, "Laser–Assisted Hair Removal", *Dermatol Clin.*, 15(3):469–477 (Jul. 1997).

Woo, "Using EpiLight® for Hair Removal Treatment of Fitzpatrick Skin Types IV and V", *Clinical Application Notes*, 2(3);1–4 (1998).

Yanai et al., "Argon Laser Therapy of Port–Wine Stains: Effects and Limitations", *Plastic and Reconstructive Surgery*, 75(4):520–525 (Apr. 1985).

Yules et al., "The Effect of Q–Switched Ruby Laser Radiation on Dermal Tattoo Pigment in Man", *Arch Surg*, 95 (Aug. 1967).

Zeitler et al., "Laser Characteristics that Might be Useful in Biology", Chapter 1, 1–18 (Not Dated).

Zelickson et al., "EpiLight® Treatment of Hair Removal Using the Circulating Cutaneous Cooling Device: Preliminary Study Report" (Not Dated).

Goldman et al., "Effect of the Laser Beam on the Skin", *The Journal of Investigative Dermatology*, 40:121–122 (Mar. 1963).

Westinghouse Engineer, "Special Blue Lamp Helps Treat Jaundice in Newborn Infants", 31(1) (Jan. 1971).

*Lumenis Ltd., et al. v. Syneron Medical Ltd., et al.*, 2:02–cv–08269–ABC–PLA, C.D. CA.—Syneron Inc's Answer to Plaintiffs' Complaint (Nov. 19, 2002).

*Lumenis Ltd., et al. v. Syneron Medical Ltd., et al.*, 2:02–cv–08269–ABC–PLA, C.D. CA.—Syneron Medical Ltd.'s Answer to Plaintiffs' Complaint (Dec. 9, 2002).

*Lumenis Ltd., et al. v. Syneron Medical Ltd., et al.*, 2:02–cv–08269–ABC–PLA, C.D. CA.—Appendix of Dictionary References in Support of Plaintiffs' Report to Court–Appointed Expert (Jan. 19, 2003).

*Lumenis Ltd., et al. v. Syneron Medical Ltd., et al.*, 2:02–cv–08269–ABC–PLA, C.D. CA.—Syneron's Appendix of Prior Art References Discussed in Declaration of Dr. Warren S. Grundfest (May 8, 2003).

*Lumenis Ltd., et al. v. Syneron Medical Ltd., et al.*, 2:02–cv–08269–ABC–PLA, C.D. CA.—Plaintiffs' Report to Court–Appointed Expert Dr. Bahram (Dec. 30, 2002).

*Lumenis Ltd., et al. v. Syneron Medical Ltd., et al.*, 2:02–cv–08269–ABC–PLA, C.D. CA.—Complaint for Patent Infringement (Oct. 30, 2002).

*Lumenis Ltd., et al., v. Syneron Medical Ltd., et al.*, 2:02–cv–08269–ABC–PLA, C.D. CA.—Declaration of Alon Maor in Support of Plaintiffs' Motion for Preliminary Injunction (Apr. 25, 2003).

*Lumenis Ltd., et al. v. Syneron Medical Ltd., et al.*, 2:02–cv–08269–ABC–PLA, C.D. CA.—Declaration of Alon Maor in Support of Plaintiffs' Ex Parte Application for Temporary Retraining Order and Order to Show Cause Re Preliminary Injunction (Oct. 30, 2002).

*Lumenis Ltd., et al. v. Syneron Medical Ltd., et al.*, 2:02–cv–08269–ABC–PLA, C.D. CA.—Declaration of Benjamin J. Fox in Opposition to Plaintiffs' Motion for a Preliminary Injunction (May 8, 2003).

*Lumenis Ltd., et al. v. Syneron Medical Ltd., et al.*, 2:02–cv–08269–ABC–PLA, C.D. CA.—Declaration of Domenic Serafino Re: Plaintiffs' Motion for Preliminary Injunction and Posting of Bond (Jul. 25, 2003).

*Lumenis Ltd., et al. v. Syneron Medical Ltd., et al.*, 2:02–cv–08269–ABC–PLA, C.D. CA.—Declaration of Dr. Michael Kreindel in Opposition to Motion for Preliminary Injunction (May 8, 2003).

*Lumenis Ltd., et al. v. Syneron Medical Ltd., et al.*, 2:02–cv–08269–ABC–PLA, C.D. CA.—Declaration of Dr. Warren S. Grundfest in Support of Syneron's Opposition to Plaintiffs' Motion for Preliminary Injunction (May 8, 2003).

*Lumenis Ltd., et al. v. Syneron Medical Ltd., et al.*, 2:02–cv–08269–ABC–PLA, C.D. CA.—Declaration of of Felix T. Woo in Support of Plaintoffs' Motion for Preliminary Injunction (May 20, 2003).

*Lumenis Ltd., et al. v. Syneron Medical Ltd., et al.*, 2:02–cv–08269–ABC–PLA, C.D. CA.—Declaration of Felix T. Woo in Support of Plaintiffs Ex Parte Application for Temporary Restraining Order and order to Show Cause Re Preliminary Injunction (Oct. 30, 2002).

*Lumenis Ltd., et al. v. Syneron Medical Ltd., et al.,* 2:02–cv–08269–ABC–PLA, C.D. CA.—Declaration of Harry F. Manbeck, Jr. in Response to Expert Report of Gerald J. Mossinghoff (May 27, 2003).

*Lumenis Ltd., et al. v. Syneron Medical Ltd., et al.,* 2:02–cv–08269–ABC–PLA, C.D. CA.—Declaration of John M. May in Support of Opposition to Plaintiffs' Ex Parte Application for Temporary Restraining Order and Order to Show Cause Regarding Preliminary Injunction (Nov. 1, 2002).

*Lumenis Ltd., et al. v. Syneron Medical Ltd., et al.,* 2:02–cv–08269–ABC–PLA, c.D. CA.—Declaration of Jordan A. Sigale in Support of Lumenis' Response to Syneron's Objections to Lumenis' Proposed Order Re: Preliminary Injunction and Posting of Bond (Jul. 31, 2003).

*Lumenis Ltd., et al. v. Syneron Medical Ltd., et al.,* 2:02–cv–08269–ABC–PLA, c.D. CA.—Declaration of Laura A. Wytsma in support of Plaintiffs' Ex Parte Application for Temporary Restraining Order and order to Show Cause Re Preliminary Injunction (Oct. 30, 2002).

*Lumenis Ltd., et al. v. Syneron Medical Ltd., et al.,* 2:02–cv–08269–ABC–PLA, C.D. CA.—Declaration of Moshe Mizrahy in Opposition to Plaintiffs' Motion for a Preliminary Injunction (May 8, 2003).

*Lumenis Ltd., et al. v. Syneron Medical Ltd., et al.,* 2:02–cv–08269–ABC–PLA, C.D. CA.—Declaration of Moshe Mizrahy in support of Oppositon to Plaintiffs Ex Parte Application for Temporary Restraining Order and Order to Show Cause Re Preliminary Injunction(Nov. 1, 2002).

*Lumenis Ltd., et al. v. Syneron Medical Ltd., et al.,* 2:02–cv–08269–ABC–PLA, C.D. CA.—Declaration of Robert Anderson in Support of Plaintiffs' Ex Parte Application for Temporary Restraining order and Order to show Cause re Preliminary Injunction (Nov. 1, 2002).

*Lumenis Ltd., et al. v. Syneron Medical Ltd., et al.,* 2:02–cv–08269–ABC–PLA, C.D. CA.—Declaration of Sarit Moussayoff in Support of Plaintiffs' Motion for Preliminary Injunction (May 20, 2003).

*Lumenis Ltd., et al. v. Syneron Medical Ltd., et al.,* 2:02–cv–08269–ABC–PLA, C.D. CA.—Declaration of Shimon Eckhouse in Support of Opposition to Plaintiffs' Ex Parte Application for Temporary Restraining Order to Show Cause Re Preliminary Injuction (Nov. 1, 2002).

*Lumenis Ltd., et al. v. Syneron Medical Ltd., et al.,* 2:02–cv–08269–ABC–PLA, C.D. CA.—Plaintiff Lumenis Ltd. And Lumenis Inc.'s Ex Parte Appliction for Temporary Restraining Order to Show Cause Re Preliminary Injunction; Memorandum of Points and Authorities; Declarations of Alon Maor, Robert Anderson and Felix T. Woo; [Proposed] Order (Oct. 28, 2000).

*Lumenis Ltd., et al. v. Syneron Medical Ltd., et al.,* 2:02–cv–08269–ABC–PLA, C.D. CA.—Expert Report of Hon. Gerald J. Mossinghoff in support of Plaintiffs' Motion for Preliminary Injunction (May 20, 2003).

*Lumenis Ltd., et al. v. Syneron Medical Ltd., et al.,* 2:02–cv–08269–ABC–PLA, C.D. CA.—Syneron Medical Ltd.'s First Amended Answer to Plaintiffs' Complaint (Apr. 23, 2003).

*Lumenis Ltd., et al. v. Syneron Medical Ltd., et al.,* 2:02–cv–08269–ABC–PLA, C.D. CA.—Syneron Inc.'s First Amended Answer to Plaintiffs' Complaint (Apr. 23, 2003).

*Lumenis Ltd., et al. v. Syneron Medical Ltd., et al.,* 2:02–cv–08269–ABC–PLA, C.D. CA.—Plaintiffs' Memorandum of Points and Authorities in Support of Motion for Preliminary Injunction (Apr. 25, 2003).

*Lumenis Ltd., et al. v. Syneron Medical Ltd., et al.,* 2:02–cv–08269–ABC–PLA, C.D. CA.—Synerons' Memorandum of Points and Authorities in Opposition to Plaintiffs' Motion for a Preliminary Injunction (May 8, 2003).

*Lumenis Ltd., et al. v. Syneron Medical Ltd., et al.,* 2:02–cv–08269–ABC–PLA, C.D. CA.—Plaintiffs' Ex Parte Application for Temporary Restraining Order and Order to Show Cause Re Preliminary Injunction (Nov. 4, 2002).

*Lumenis Ltd., et al. v. Syneron Medical Ltd., et al.,* 2:02–cv–08269–ABC–PLA, C.D. CA.—Notice of Errata Re Plaintiffs' Ex Parte Application for Temporary Restraining Order to Show Cause Re Preliminary Injunction (Oct. 30, 2002).

*Lumenis Ltd., et al. v. Syneron Medical Ltd., et al.,* 2:02–cv–08269–ABC–PLA, C.D. CA.—Notice of Errata (Jan. 8, 2003).

*Lumenis Ltd., et al. v. Syneron Medical Ltd., et al.,* 2:02–cv–08269–ABC–PLA, C.D. CA.—Plaintiff's Notice of Lodging Opinion and Tutorial of Court Appointed Expert Dr. Oscar M. Stafsudd (Apr. 25, 2003).

*Lumenis Ltd., et al. v. Syneron Medical Ltd., et al.,* 2:02–cv–08269–ABC–PLA, C.D. CA.—Notice of Response of Court Appointed Expert to Order Seeking Clarification (Jun. 16, 2003).

*Lumenis Ltd., et al. v. Syneron Medical Ltd., et al.,* 2:02–cv–08269–ABC–PLA, C.D. CA.—Syneron Inc.'s Objection to Declaration of Robert Anderson Submitted in Support of Plaintiffs' Ex Parte Application for Temporary Restraining order and Order to Show Cause Re Preliminary Injunction (Nov. 1, 2002).

*Lumenis Ltd., et al. v. Syneron Medical Ltd., et al.,* 2:02–cv–08269–ABC–PLA, C.D. CA.—Defendant Syneron, Inc.'s Opposition to Plaintiffs' Ex Parte Application for Termporary Restraining Order and Order to Show Cause Re Preliminary Injunction (Nov. 1, 2002).

*Lumenis Ltd., et al. v. Syneron Medical Ltd., et al.,* 2:02–cv–08269–ABC–PLA, C.D. CA.—Plaintiffs' Motion for Preliminary Injunction (Jul. 11, 2003).

*Lumenis Ltd., et al. v. Syneron Medical Ltd., et al.,* 2:02–cv–08269–ABC–PLA, C.D. CA.—Plaintiffs' Motion for Preliminary Injunction (Aug. 5, 2003).

*Lumenis Ltd., et al. v. Syneron Medical Ltd., et al.,* 2:02–cv–08269–ABC–PLA, C.D. CA.—Reply of Plaintiffs Lumenis Ltd. And Lumenis Inc. in Support of Motion for Preliminary Injunction (May 22, 2003).

*Lumenis Ltd., et al. v. Syneron Medical Ltd., et al.,* 2:02–cv–08269–ABC–PLA, C.D. CA.—Reply Opinion of Joseph T. Walsh, Jr. in support of Plaintiffs' Motion for Preliminary Injunction (May 20, 2003).

*Lumenis Ltd., et al. v. Syneron Medical Ltd., et al.,* 2:02–cv–08269–ABC–PLA, C.D. CA.—Syneron's Response Brief for Court–Appointed Expert Re: Claim Construction (Jan. 17, 2003).

*Lumenis Ltd., et al. v. Syneron Medical Ltd., et al.,* 2:02–cv–08269–ABC–PLA, C.D. CA.—Plaintiffs' Response Brief to Court–Appointed Expert (Jan. 9, 2003).

*Lumenis Ltd., et al., v. Syneron Medical Ltd., et al.,* 2:02–cv–08269–ABC–PLA, C.D. CA.—Submission of Materials for Court Appointed Expert Pursuant to the Parties' Joint Stipulation (Dec. 19, 2002).

*Lumenis Ltd., et al. v. Syneron Medical Ltd., et al.,* 2:02–cv–08269–ABC–PLA, C.D. CA.—Supplemental Declaration Of Alon Moar in Support of Plaintiff Lumenis, Inc.'s Motion for Preliminary Injunction (May 23, 2003).
*Lumenis Ltd., et al. v. Syneron Medical Ltd., et al.,* 2:02–cv–08269–ABC–PLA, C.D. CA.—Supplemental Declaration of Felix T. Woo in Support of Plaintiffs' Ex Parte Application for Temporary Restraining Order and Order to Show Cause Re Preliminary Injunction (Nov. 4, 2002).
*Lumenis Ltd., et al. v. Syneron Medical Ltd., et al.,* 2:02–cv–08269–ABC–PLA, C.D. CA.—Plaintiffs' Disclosures Persuant to Fed.R.Civ.P.26 (Jan. 14, 2003).
*Lumenis Ltd., et al. v. Syneron Medical Ltd., et al.,* 2:02–cv–08269–ABC–PLA, C.D. CA.—Plaintiffs' Response to Synerons' First Set of Interrogatories (Jan. 13, 2003).
*Lumenis Ltd., et al. v. Alma Ltd., et al.,* 07:CV3622, N.D.Ill.—Videotaped Deposition of Richard R. Anderson, M.D. (Dec. 13, 2007).
Aculight HR, *Operator Manual*, PB 3581110 Revision B (Jul. 2001).
AestiLight™ Millennium, *Operator Manual*, PB 3381110 Revision A (Aug. 2003).
AestiLight™ Photo Epilation System, *AestiLight Service Manual*, PB 3380120 Revision B (Mar. 2000).
AestiLight™ Photo Epilation System, *Operator Manual*, PB 3380110 Revision A (May 1999).
EpiLight® Hair Removal System, *Operator Manual*, PB 400–9001 Revision 9 (Aug. 2000).
EpiLight™ Hair Removal System, *Operator Manual*, PB 400–9001 Revision 2 (Jul. 1996).
EpiLight™ Hair Removal System, Operator Manual, PB 400–9001 Revision 5 (Aug. 1997).
EpiLight™ Hair Removal System, Operator Manual, PB 400–9001 Revision 2 (Jul. 1996).
EpiLight™ Hair Removal System, Operator Manual, PB 400–9001 Revision 4 (Jul. 1997).
EpiLight™ Hair Removal System, Operator Manual, PB400–9001 Revision 1 (Jun. 1996).
EpiLight™ Hair Removal System, Operator's Manual, PB 400–9001 Revision 7 (Jan. 1998).
EpiLight™ Hair Removal System, Operator's Manual, PB 400–9001 Revision 6 (Dec. 1997).
EpiLight™ Hair Removal, Operator Manual, PB 400–9001 Revision 3 (Feb. 1997).
IPL Quantum HR, Operator's Manual, PB 3580110 Revision B (Jun. 2001).
IPL Quantum SR, Operator's Manual, PB 3680010 Revision A (Sep. 2000).
IPL™ Quantum DL, Operator's Manual, PB 3780110 Revision B (Jul. 2002).
IPL™ Quantum HR, Operator's Manual , PB 3580110 Revision D, (Jul. 2002).
IPL™ Quantum HR, Operator's Manual, PB 3580110 Revision C (Dec. 2001).
IPL™ Quantum SR, Operator Manual, PB 3680110 Revision D (Oct. 2002).
Lumenis IPL™ Quantum, *Service Manual*, (Mar. 2002).
PhotoDerm®, *Operator Manual*, PB 200–9001 Revision 1 (Jun. 1996).
PhotoDerm PL, *Operator Manual*, PB 200–9012 Revision A (May 1997).
PhotoDerm VL, *Operator Manual*, PB 100–9033 Revision A (May 1997).

PhotoDerm® VL, *Operator Manual*, (Jul. 1997).
PhotoDerm® VL, *Operator Manual*, PB 100–9001 Revision 2B (Oct. 1995).
PhotoDerm® VL, *Operator Manual*, PB 100–9001–1 Revision 1 (Apr. 1995).
PhotoDerm® VL/PL, *Operator's Manual*, PB 2180150 Revision B (May 1998).
PhotoDerm® VL/PL, *Service Manual*, PB 100–9022 Revision 2 (Nov. 1996).
PhotoDerm® VL/PL/HR, *Operator Manual*, PB 2280150 Revision B (May 1998).
TwoHead PhotoDerm®, *Service Manual*, (Apr. 2000).
VascuLight EPI Mode, *Operating Instructions*, PB 2300410 Revision C (Dec. 2001).
VascuLight™ Elite, *Operator's Manual*, PB 2780110 Revision A (Oct. 2002).
VascuLight™, *Operator Manual*, PB 2380150 Revision B (2001).
Epilight® Hair Removal System, *Service Manual*, PB4009007 Revision B (Jan. 1999).
Aculight™ *Operator's Manual*, PB3581110 Revision 0 (Feb. 2001).
IPL Quantum HR, *Operator Manual*, PB3580110 Revision A (Jun. 2000).
Epilight® Hair Removal System, *Operator Manual*, PB 4009001Revision (Nov. 1998).
ESC Medical, "New Photo–Epilation Technique for Hair Removal", *Medco Forum*, 4(13) (Sep. 1997).
Reliant Technologies, Inc. Product News,Accu–Scan, Multi–Wavelength Laser Scanning System for CO2, Jan. 25, 1995, 3 pages.
Sharplan Swiftlase Flashscan, Jun. 1993.
Unilase A new CO2 Laser for Microsurgery, I.L. Med. Newsletter, vol. 1, No. 3, Spring 1991.
I. L. Med. Unilase System Brochure (1993).
R. Rox Anderson et al., *Microvasculature Can be Selectively Damaged Using Dye Lasers,* Journal of Lasers in Surgery and Medicine, 1981.
Gros, et al, Diaphanologie Mammaire, Memoires Originaux, *J. Radiol. Electrol.,* 53(4):297–306 (1972), in French, with English translation.
Brochure for an Infrared Coagulator by Redfield Corporation (1968).
Groot & Johnson, "Lasers and Advanced Dermatological Instrumentation", *Australas J. Dermatol.,* 28:77–85 (1987).
Kaufmann et al., "Pulsed Er: YAG– and 308 nm UV–Excimer Laser: An In Vitro and In Vivo Study of Skin–Ablative Effects", Laser Surg. Med., 9:132–140 (1989).
Goldman, *Biomedical Aspects of the Laser—An Introduction of Laser Applications Into Biology and Medicine,* chapters 1, 2, 23 and index (1967).
Gossman et al., "Experimental Comparison of Laser and Cryosurgical Cilia Destruction", *Ophthalmic Surgery,* 23(3):179–182 (Mar. 1992).
Gossman et al., "Prospective Evaluation of the Argon Laser in the Treatment of Trichiasis", *Ophthalmic Surgery,* 23(3):183–187 (Mar. 1992).
"The Spectrum RD—1200 Q–Switched Ruby Laser", (Not Dated).
ESC Medical Systems, "Control of Pulse Duration and Pulse Secuence Delays for Effective Photo–Epilation", *EpiLight Hair Removal System Application Notes,* 3(2) (1997).

Geronemus, "Laser and Pulsed Light Source Treatment of Leg Vessels", (Sep. 1995).

Goldman, "Effects of New Laser Systems on the Skin", *Arch Dermatol,* 108(3):385–90 (Sep. 1973).

Goldman, "Treating Varicose and Telangiectatic Leg Veins", *Federal Practitioner* (Mar. 1997).

Kincade, "New Procedures push tissue studies beneath the surface", *Laser Focus World,* pp. 57–63, (Aug. 1995).

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 16-23 is confirmed.

Claims 1-15 were previously cancelled.

Claims 24 and 26 are determined to be patentable as amended.

Claims 25 and 27-33, dependent on an amended claim, are determined to be patentable.

New claims 34-46 are added and determined to be patentable.

24. A method for destroying blood vessels contained at a selected depth and in a selected area of the dermis, the method comprising:
 positioning a diode laser so that light from the diode laser will impinge upon the selected area of the dermis, wherein the selected area of the dermis is at least 1 square centimeter; and
 *directing the light from the diode laser to the selected area of the dermis using a light guide;*
 operating the diode laser to deliver at least one light pulse to the skin surface of the selected area having a wavelength of about 810 nm, with each pulse delivering a fluence at a skin surface above the selected area of the dermis between about 5 joules per square centimeter and 50 joules per square centimeter, and each pulse having a pulse duration of between about 0.2 millisecond and 20 milliseconds*; and*
 *destroying blood vessels in the selected area of the dermis.*

26. The method of claim 24 comprising controlling the fluence delivered by the diode laser to the area to control the depth at which [a] *the* blood vessel is destroyed within the dermis.

*34. The apparatus of any one of claims 16-17 or 21 or 33 further comprising an electrical gate configured to control the duration of the at least one pulse of light.*

*35. The apparatus of any one of claims 16-17 or 21 or 33 further comprising an optical gate configured to control the duration of the at least one pulse of light.*

*36. The apparatus of any one of claims 16-18 or 21 or 33 further comprising a shutter configured to control the duration of the at least one pulse of light.*

*37. The apparatus of claim 22 further comprising an electrical gate configured to control the duration of the at least one pulse of light.*

*38. The apparatus of claim 22 further comprising an optical gate configured to control the duration of the at least one pulse of light.*

*39. The apparatus of claim 22 further comprising a shutter configured to control the duration of the at least one pulse of light.*

*40. The method of any one of claims 24-32 further comprising controlling the duration of the at least one light pulse using an electrical gate.*

*41. The method of any one of claims 24-32 further comprising controlling the duration of the at least one light pulse using an optical gate.*

*42. The method of any one of claims 24-32 further comprising controlling the duration of the at least one light pulse using a shutter.*

*43. An apparatus for destroying blood vessels contained at a selected depth and in a selected area of the dermis, the apparatus comprising:*
 *a diode laser configured to emit at least one pulse of light to the skin surface above the selected area having a wavelength of about 940 nm, with each pulse delivering a fluence between about 5 Joules per square centimeter and 50 Joules per square centimeter, and each pulse having a pulse duration of between about 0.2 and 20 milliseconds; and*
 *a light guide having an area of between about 0.1 square centimeter to 10 square centimeters and configured to direct light to impinge upon an area of the skin,*
 *wherein the diode laser and the light guide are configured to be positioned relative to the selected area of the dermis such that light from the diode laser can impinge upon the selected area of the dermis.*

*44. An apparatus for destroying blood vessels contained at a selected depth and in a selected area of the dermis, the apparatus comprising:*
 *a diode laser configured to emit at least one pulse of light to the skin surface above the selected area having a wavelength of about 980 nm, with each pulse delivering a fluence between about 5 Joules per square centimeter and 50 Joules per square centimeter, and each pulse having a pulse duration of between about 0.2 and 20 milliseconds; and*
 *a light guide having an area of between about 0.1 square centimeter to 10 square centimeters and configured to direct light to impinge upon an area of the skin,*
 *wherein the diode laser and the light guide are configured to be positioned relative to the selected area of the dermis such that light from the diode laser can impinge upon the selected area of the dermis.*

*45. An apparatus for destroying blood vessels contained at a selected depth and in a selected area of the dermis, the apparatus comprising:*
 *a diode laser configured to emit at least one pulse of light to the skin surface above the selected area having a wavelength of about 800 nm, with each pulse delivering a fluence between about 5 Joules per square centimeter and 50 Joules per square centimeter, and each pulse having a pulse duration of between about 0.2 and 20 milliseconds; and*
 *a light guide having an area of between about 0.1 square centimeter to 10 square centimeters and configured to direct light to impinge upon an area of the skin, wherein the light guide is solid,*
 *wherein the diode laser and the light guide are configured to be positioned relative to the selected area of the dermis such that light from the diode laser can impinge upon the selected area of the dermis.*

*46. The method of claim 24 further comprising at least one of preventing and significantly delaying regrowth of hair contained in the selected area of the dermis.*

\* \* \* \* \*